US008710429B2

(12) United States Patent
Hanas et al.

(10) Patent No.: US 8,710,429 B2
(45) Date of Patent: Apr. 29, 2014

(54) IDENTIFICATION OF BIOMARKERS IN BIOLOGICAL SAMPLES AND METHODS OF USING SAME

(75) Inventors: Jay S. Hanas, Edmond, OK (US); James R. Hocker, Edmond, OK (US); Daniel J. Brackett, Seminole, OK (US); Russell G. Postier, Edmond, OK (US); Marvin D. Peyton, Oklahoma City, OK (US); John Y. Cheung, Bellingham, WA (US)

(73) Assignee: The Board of Regents of the University of OK, Normal, OK (US)

( * ) Notice: Subject to any disclaimer, the term of this patent is extended or adjusted under 35 U.S.C. 154(b) by 298 days.

(21) Appl. No.: 12/341,252

(22) Filed: Dec. 22, 2008

(65) Prior Publication Data

US 2009/0159793 A1 Jun. 25, 2009

Related U.S. Application Data

(60) Provisional application No. 61/008,750, filed on Dec. 21, 2007.

(51) Int. Cl.
*B01D 59/44* (2006.01)

(52) U.S. Cl.
USPC .............................. 250/282; 435/23; 436/173

(58) Field of Classification Search
USPC .............................................................. 250/282
See application file for complete search history.

(56) References Cited

U.S. PATENT DOCUMENTS

| | | | | |
|---|---|---|---|---|
| 6,906,320 | B2 * | 6/2005 | Sachs et al. | 250/282 |
| 7,109,038 | B2 * | 9/2006 | Scholl et al. | 436/66 |
| 2005/0048547 | A1 | 3/2005 | Zhao et al. | |
| 2005/0170352 | A1 * | 8/2005 | Chan et al. | 435/6 |
| 2006/0121539 | A1 * | 6/2006 | Debinski et al. | 435/7.23 |
| 2009/0127454 | A1 * | 5/2009 | Ritchie et al. | 250/282 |

FOREIGN PATENT DOCUMENTS

WO WO 2007030928 A2 * 3/2007

OTHER PUBLICATIONS

Petricoin et al. , "Use of proteomic patterns in serum to identify ovarian cancer", Lancet 359: 572-577, 2002.*

Koomen, J.M. et al.; "Diagnostic protein discovery using liquid chromatograph/mass spectrometry for proteolytic peptide targeting"; Rapid Communications in Mass Spectrometry; 19(12); p. 1624-1636; 2005.

Chen, J. et al.; "Characterization of apolipoprotein and apolipoprotein precusors in pancreatic cancer serum samples via two-dimensional liquid chromatography and mass spectrometry"; J Chromatogr A; 1162(2); p. 4-8; Aug. 31, 2007.

* cited by examiner

*Primary Examiner* — Phillip A Johnston
(74) *Attorney, Agent, or Firm* — Dunlap Codding, P.C.

(57) ABSTRACT

The present invention is directed to methods of identifying biomarkers in liquid biological samples obtained from cancer patients or patients exhibiting a disease state. Such methods may include the use of electrospray ionization-time of flight mass spectrometry (ESI-TOF MS).

29 Claims, 13 Drawing Sheets
(2 of 13 Drawing Sheet(s) Filed in Color)

Alpha-2-macroglobulin, precursor

MGKNKLLHPSLV..FKKRTTVMVKNEDSLVFVQTDKSIYKPGQTVKFRVVSMDENFHPLNELIPLVYIQDPKGNRIAQWQSFQLE
GGLKQFSFPLSSEPFQGSYKVVVQKKSGGRTEHPFTVEEFVLPKFEVQVTVPKIITILEEEMNVSVCGLYT...VRLVDGKGVPIP
NKVIFIRGNEANYYSNATTDEHGLVQFSINTTNVMGTSLTVRVNYKDRSPCYGYQWVSEEHEEAHHTAYLVFSPSKSFVHLEPMS
HELPCGHTQTVQAHYILNGGTLLGLKKLSFYYLIMAKGGIVRTGTHGLLVKQEDMKGHFSISIPVKSDIAPVARLLIYAVLPTGD
VIGDSAKYDVENCLANKVDLSFSPSQSLPASHAHLRVTAAPQSVCALRAVDQSVLLMKPDAELSASSVYNLLPEKDLTGFPGPLN
DQDDEDCINRHNVYINGITYTPVSSTNEKDMYSFLEDMGLKAFTNSKIRKPKMCPQLQQYEMHGPEGLRVGFYESDVMGRGHA
RLVHVEEPHTETVRKYFPETWIWDLV..LGISSTASLRAFQPFFVELTMPYSVIRGEAFTLKATVLNYLPKCIRVSVQLEASPA
FLAVPVEKEQAPHCICANGRQTVSWAVTPKSL..PSGGEVSEELSLKLPPNVVEESARASVSVLGDILGSAMQN..LNTGYQRQ
LNYKHYDGSYSTFGERYGRNQGNTWLTAFVLKTFAQARAYIFIDEAHIT..KWITKQQNAQGGFSSTQDTVVALHALSKYGAAT
FTRTGKAAQVTIQSSGTFSSKFQVDNNNR...DEPKAHTSFQISLSVSYTGSRSASNMAIVDVKMVSGFIPLKPTVKMLE..DVPVR
DLKPAIVKVYDYYETDEFAIAEYNAPCSKDLGNA Mass (average): 163278.0 Identifier: gi|25303946 Protein Coverage: 13.7%

B

| Sequence | # | b | y | (+1) |
|---|---|---|---|---|
| V | 1 | 100.1 | 1885.2 | 18 |
| S | 2 | 187.2 | 1786.1 | 17 |
| V | 3 | 286.4 | 1699.0 | 16 |
| Q | 4 | 414.5 | 1599.9 | 15 |
| L | 5 | 527.6 | 1471.7 | 14 |
| E | 6 | 656.8 | 1358.6 | 13 |
| A | 7 | 727.8 | 1229.5 | 12 |
| S | 8 | 814.9 | 1158.4 | 11 |
| P | 9 | 912.0 | 1071.3 | 10 |
| A | 10 | 983.1 | 974.2 | 9 |
| F | 11 | 1130.3 | 903.1 | 8 |
| L | 12 | 1243.4 | 755.9 | 7 |
| A | 13 | 1314.5 | 642.8 | 6 |
| V | 14 | 147.2 | [illegible] | 5 |
| P | 15 | 1510.8 | 472.6 | 4 |
| V | 16 | 1609.9 | 375.4 | 3 |
| E | 17 | 1739.0 | 276.3 | 2 |
| K | 18 | 1867.2 | 147.2 | 1 |

C

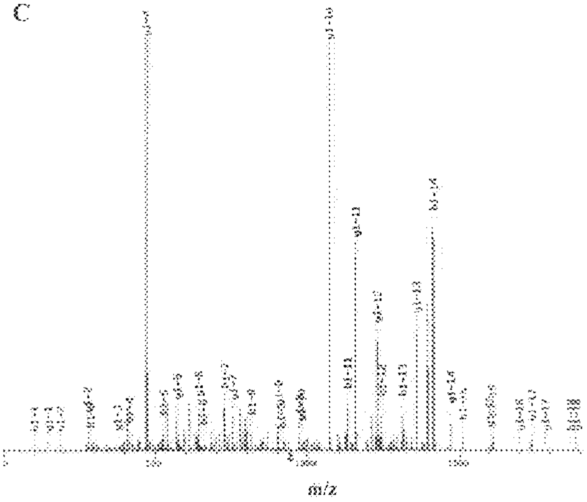

Ceruloplasmin, precursor

MKILILGIFLFLCSTPAWAKEKHYYIGIIETTWDYASDHGEKKLISVDTEHSNIYLQNGPDRIGRLYKKALYLQYTDETFRTTIEKP
VWLGFLGPIIKAETGDKVYVHLKNLASRPYTFHSHGITYYKEHEGAIYPDNTTDFQRADDKVYPGEQYTYMLLATEEQSPGEG
DGNCVTRIYHSHIDAPKDIASGLIGPLIICKKDSLDKEKEKHIDREFVVMFSVVDENFSWYLEDNIKTYCSEPEKVDKDNEDFQES
NRMYSVNGYTFGSLPGLSMCAEDRVKWYLFGMGNEVDVHAAFFHGQALTNKNYRIDTINLFPATLFDAYMVAQNPGEWMLSC
QNLNHLKAGLQAFFQVQECNKSSSKDNIRGKHVRHYYIAAEEIIWNYAPSGIDIFTKENLTAPGSDSAVFFEQGTTRIGGSYKKLV
YREYTDASFTNRKERGPEEEHLGILGPVIWAEVGDTIRVTFHNKGAYPLSIEPIGVRFNKNNEGTYYSPNYNPQSRSVPP
SASHVAPTETFTYEWTVPKEVGPTNADPVCLAKMYYSAVDPTKDIFTGLIGPMKICKKGSLHANGRQKDVDKEFYLFP
TVFDENESLLLEDNIRMFTTAPDQVDKEDEDFQESNKMHSMNGFMYGNQPGLTMCKGDSVVWYLFSAGNEADVHGIYFSGNT
YLWRGERRDTANLFPQTSLTLHMWPDTEGTFNVECLTTDHYTGGMKQKYTVNQCRRQSEDSTFYLGERTYYIAAVEVEWDYS
PQREWEKELHHLQEQNVSNAFLDKGEFYIGSKYKKVVYRQYTDSTFRVPVERKAEEEHLGILGPQLHADVGDKVKIIFKNMA
TRPYSIHAHGVQTESSTVTPTLPGETLTYVWKIPERSGAGTEDSACIPWAYYSTVDQVKDLYSGLIGPLIVCRRPYLKVF
NPRRKLEFALLFLVFDENESWYLDDNIKTYSDHPEKVNKDDEEFIESNKMHAINGRMFGNLQGLTMHVGDEVNWYLMGMGNE
IDLHTVHFHGHSFQYKHRGVYSSDVFDIFPGTYQTLEMFPRTPGIWLLHCHVTDHIHAGMETTYTVLQNEDTKSG

Mass (average): 122205.2 Identifier: gi|4557485 Protein Coverage: 11.07%

B

Complement C3

[illegible]

Mass (average): [illegible] Identifier: [illegible] Protein Coverage: 16.?5%

Figure 8

| Number of injections Tested | Injections: Adeno(n=57); Squamous(n=71); Cancer(n=128); Control(n=64); Total(n=192) | Injections Identified/Possible (%) |
|---|---|---|
| 64 | Positive Identification (I.D.) Control (Control) | 62/64 (96.8%) |
| 128 | Positive ID as Cancer (Cancer, Adeno, or Squamous) | 130/128 (101.6%)* |
| 192 | Correct partial I.D. only( Cancer missing Adeno or Squamous; Adeno or Squamous missing Cancer; Control and Cancer, Adeno or Squamous) | 6/192 (3.1%) |
| 192 | Correct I.D. only | 185/192 (96.4%) |
| 64 | I.D. as Control (include Null and partial I.D.) | 65/64 (101.6%)* |
| 192 | False Negative (any Cancer sample I.D. as Control or Null) | 1/192 (0.01%) |
| 192 | False Positive (include Control I.D. with either: Cancer, Adeno, or Squamous) | 2/192 (1.0%) |
| 192 | Null : did not meet cutoff criteria for all 4 tests | 1/192 (0.01%) |
| 128 | Correctly ID as Cancer with Adeno or Squamous (requires: Cancer and Squamous or Adeno) | 123/128 (96.1%) |
| 64 | Correctly I.D. as Control (requires Control I.D. only , no other I.D. can be present) | 62/64 (96.9%) |

| Number of Patients Tested | Patients: Adeno(n=19); Squamous(n=24); Cancer(n=43); Control(n=23) | Patients Identified/Possible (%) (all injections agree) |
|---|---|---|
| 23 | Control | 21/23 (91.3%) |
| 19 | Adenocarcinoma | 19/19 (100%) |
| 24 | Squamous | 23/24 (95.8%) |
| 43 | Cancer | 42/43 (97.6%) |

| Number of Patients Tested | Patients: Adeno(n=19); Squamous(n=24); Cancer(n=43); Control(n=23) | Patients Identified/Possible (%) Requires 2/3 Consensus for Identification |
|---|---|---|
| 23 | Control | 23/23 (100%) |
| 19 | Adenocarcinoma | 19/19 (100%) |
| 24 | Squamous | 24/24 (100%) |
| 43 | Cancer | 43/43 (100%) |

*Includes incorrect I.D.s

DIFFERENT SIGNIFICANT PEAKS APPEAR IN LUNG CANCER AND PANCREATIC CANCER

Haptoglobin

MRALGAVVTLLLWGQLFAVELGNDATDIEDDSCPKPPEIANGYVEHLVRYRCRQFYKLQ
TEGDGIYTLNSEKQWVNPAAGDKLPKCEAVCGKPKHPVDQVQRIIGGSMDAKGSFPWQA
KMISRHGLTTGATLISDQWLLTTAQNLFLNHSENATAKDIAPTLTLYVGKNQLVEIEKVVL
HPERSVVDIGLIKLKQKVLVTEKVMPICLPSKDYVAPGRMGYVSGWGRNVNFRFTERLK
YVMLPVADQEKCELHYEKSTVPEK<u>KGAVSPVGVQPILNK</u>HTFCAGLTKYEEDTCYGDA
GSAFAVHDTEEDTWYAAGILSFDKSCAVAEYGVYVRATDLKDWVQETMAKN

Mass (average): 38563.2 Identifier: gi|59808182 Protein Coverage: 38% 133/348 AA

B

| Seq | # | b | y | (+1) |
|---|---|---|---|---|
| K | 1 | 129.2 | 1507.8 | 15 |
| G | 2 | 186.2 | 1379.6 | 14 |
| A | 3 | 257.3 | 1322.6 | 13 |
| V | 4 | 356.4 | 1251.5 | 12 |
| S | 5 | 443.5 | 1152.4 | 11 |
| P | 6 | 540.6 | 1065.3 | 10 |
| V | 7 | 639.8 | 968.2 | 9 |
| G | 8 | 696.8 | 869.1 | 8 |
| V | 9 | 796.0 | 812.0 | 7 |
| Q | 10 | 924.1 | 712.9 | 6 |
| P | 11 | 1021.2 | 584.7 | 5 |
| I | 12 | 1134.4 | 487.6 | 4 |
| L | 13 | 1247.5 | 374.5 | 3 |
| N | 14 | 1361.6 | 261.3 | 2 |
| K | 15 | 1489.8 | 147.2 | 1 |

C

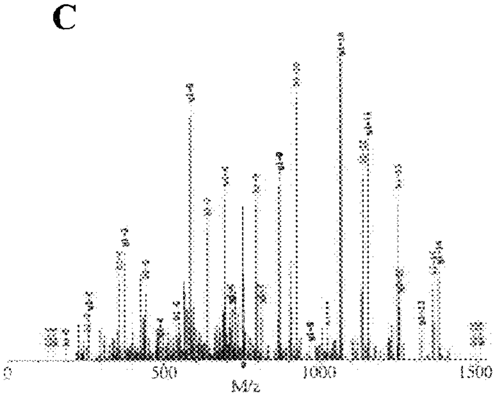

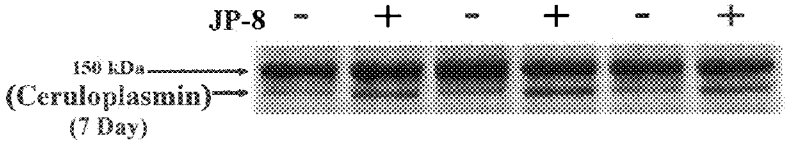

B

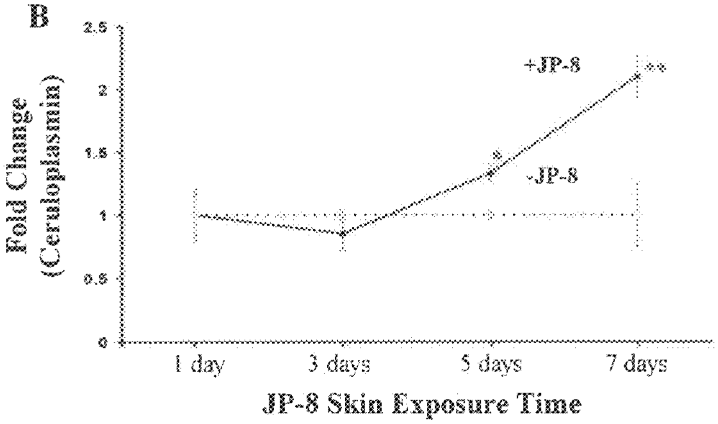

IDENTIFICATION OF BIOMARKERS IN BIOLOGICAL SAMPLES AND METHODS OF USING SAME

CROSS REFERENCE TO RELATED APPLICATIONS

This application claims benefit under 35 U.S.C. 119(e) of provisional application U.S. Ser. No. 61/008,750, filed Dec. 21, 2007. The entire content of the above-referenced patent application is hereby expressly incorporated herein by reference.

STATEMENT REGARDING FEDERALLY SPONSORED RESEARCH OR DEVELOPMENT

The government owns certain rights in the present invention pursuant to a grant from the Department of Defense (Grant #F49620-01).

BACKGROUND OF THE INVENTION

In 2007, approximately 200,000 lung and pancreatic cancer deaths occurred in the United States. Earlier detection with respect to progression of lung and pancreatic cancer would significantly reduce these mortality numbers. Identification of cancer biomarkers is a proven strategy for the screening and early treatment of cancer. Small amounts of peripheral blood are readily available for cancer biomarker identification and analysis. This is best exemplified by the PSA (prostate specific antigen) blood test screen for prostatic cancer. The development of biomarker blood tests to assist in the detection and diagnosis of lung and pancreatic cancers, especially in its earlier, curable, stages is imperative. Individuals with risk factors for these diseases (smoking, alcohol use, and family history) would benefit from blood tests developed for early detection of these carcinomas.

Mass spectrometry (MS) is the technical foundation of protein biomarker analysis, and its use is becoming more mandatory in cancer and disease research. Modern mass spectrometry is capable of high resolution, sensitivity, mass accuracy, and is robust in operation. Coupled with one-dimensional (1-D) or two-dimensional (2-D) gel electrophoresis, micro-HPLC, surface-enhanced templates, and various software packages, large numbers of proteins and peptides can be identified and quantified. The masses of different molecules are unique, and in order to determine the mass of that molecule, it must first be ionized. There are two ways to ionize biomolecules for mass spectrometry: laser desorption/ionization (LDI) and electrospray ionization (ESI). Once ionized, there are essentially two ways to determine mass: using a quadrupole/ion trap, and using a time-of-flight (TOF) mass analyzer. Mass spectrometry-based approaches have identified proteins specific for a number of cancers, including breast, prostate and lung cancer. Surface-enhanced laser desorption/ionication (SELDI) is an MS technique performed by coating metal grids with affinity matrices and then binding proteins/peptides from biological fluids to these surfaces followed by laser desorption and time of flight (TOF) mass determination of proteins/peptides. MALDI MS analysis (matrix-assisted laser desorption/ionization) was able to detect proteins/peptides present in control sera but absent in sera from pancreatitis/pancreatic cancer patients.

Another use of mass spectrometry in cancer and disease diagnostics is profiling of the small molecule, low mass range (approximately 500 to 5000 m/z values) of serum. This methodology, referred to as serum proteomic profiling or serum profiling, relies upon the high resolution and mass accuracy of modern mass spectrometers as well as statistical analysis software to analyze, distinguish, and classify thousands of mass peaks at once. This technology application is based upon the concept that changes in the physiological state of the human body (e.g., by disease) are reflected in changes in biomarkers present in serum. These changes could result from tissues and organs secreting and/or shedding different amounts and kinds of biomarkers and/or altered biomarkers (e.g., proteins, peptides, lipids, nucleic acids) into the circulating bloodstream. These changes could be due to duress on organ homeostasis, bodily defenses, and disease mechanisms themselves. This technology was previously used to distinguish serum mass peak patterns for breast and prostate cancer, and to develop a blood test for ovarian cancer, which, like pancreatic cancer, is very hard to diagnose in its early, curable stages A number of previous studies have identified biomarkers in lung cancer patients using mass spectrometry as well as other approaches. One group used MALDI MS and found that serum proteins amyloid A and macrophage migration inhibitory factor were elevated in lung cancer patients (Howard et al., 2004). No distinction was made in the types of lung cancer identified, and the prognostic value of these markers was found to be limited. A more successful study was reported using SELDI MS analysis from 158 lung cancer patients and 50 controls in which a series of proteins was shown to identify non-small cell lung carcinoma 91.4% of the time (Yang et al., 2005). The analysis was not able to distinguish early stage cancer from controls. A novel approach to identify lung cancer biomarkers involves the use of breath analysis of compounds and/or their patterns uniquely exhaled by lung cancer patients. One study using this technology reported the measurement of 13 volatile organic compounds in the exhaled breath of lung cancer patients with a diagnostic accuracy of 80% (Poli et al., 2005). However, these were incapable of distinguishing types of lung cancer or identifying early stages of the disease.

A number of protein biomarkers have been identified in the sera and pancreatic juices from pancreatitis and pancreatic cancer patients. Serum biomarker protein CA-19.9 is presently used to monitor pancreatic cancer but is not useful in early diagnosis (Gattani et al., 1996). The sera and pancreatic juice of pancreatitis patients contain elevated proteases (Leto et al., 1997). Sera of pancreatic cancer patients have elevated anti-proteases (Yu et al., 2005; and Trachte et al., 2002). Phosphoglycerate kinase (PGK) was found elevated in pancreatic cancer sera (Hwang et al., 2006), and insulin-like growth factor binding protein 2 was elevated in pancreatic juice from pancreatic adenocarcinoma patients (Chen et al., 2006). The hepatocarcinoma-intestine-pancreas/pancreatitis associated protein I was identified by mass spectrometry analysis as a potential pancreatic cancer biomarker from pancreatic juice (Rosty et al., 2002). However, none of these studies were able to clearly distinguish early clinical stages of pancreatic cancer from controls.

The use of mass spectrometry (MS) to identify peptide/protein differences between sera of control and disease states holds promise in diagnostics (Richter et al., 1999). The presently disclosed and claimed invention is based on the premise that sera contain very large numbers of low molecular weight peptides and other small molecules, and this complexity will vary between disease states. The basis for this complexity likely involves exopeptidase degradation of cell proteins (Villanueva et al., 2006), and could reflect homeostatic mechanisms which change with physiological state. This results in organs/tissues shedding/secreting different amounts/kinds of biomolecules. This methodology, referred to as serum proteomic profiling or serum profiling, relies upon the high resolution and mass accuracy of modern mass spectrometers as well as bioinformatic/statistic software to be able to analyze and distinguish thousands of mass peaks. Standard statistical approaches, like those utilized in the presently disclosed and claimed invention (and described in detail herein after), are better for analysis than novel algorithms (Semmes et al., 2005). Profiling of sera and other biological fluids is presently used to catalog disease states and identify biomarker patterns in many cancers including lung/pancreatic cancer (Yang et al., 2005; and Li et al., 2002). However, for reasons given below, SELDI (surface enhanced laser desorption-ionization) MS analysis of sera has a number of problems yet the cancer biomarker field exclusively uses this technology (Sorace et al., 2003). In SELDI, sera samples are placed on affinity grids to separate peptides and proteins. Samples are then washed, ionization chemicals added, and then dried. All of these steps have the potential for artifact introduction, especially with sample crystallization which is a random process that affects the ionization step in laser desorption MS.

Presently, this emerging technology has various shortcomings, including the MS technologies and analysis techniques currently utilized. The SELDI technology involves prefractionation of sera followed by chemical addition and crystallization, and thus is a solid state analysis, which is much more difficult than an all liquid state analysis. In addition, this solid state analysis will require a much larger amount of sample than a liquid analysis would require.

Therefore, the present invention is directed to new and improved methods of identifying biomarkers in cancer or disease sera using MS techniques that overcome the defects and disadvantages of the prior art.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 3 illustrates tandem mass spectrometry identification of a 2-macroglobulin in pancreatic cancer sera. Tryptic digestion of protein bands in FIG. 2, ESI-MS/MS, and data analysis were performed as described in METHODS. Panel A exhibits the peptide sequence information (15 peptides in bold) obtained using ESI-MS/MS analysis of the uppermost bands in FIG. 2. These sequences matched those found in the human a 2-macroglobulin precursor molecule; this sequence contains the N-terminal signal sequence of the precursor. Panels B and C provide more detailed information on the identification of the fourth peptide from the N-terminus. Panel B exhibits the b-ion and y-ion series for the underlined peptide in A with actual fragment ions identified in bold. Panel C exhibits the raw MS/MS spectrum for the underlined peptide.

FIG. 4 depicts amino acid sequence identification of sera ceruloplasmin and complement C3 by tandem mass spectrometry. Protein sample preparation, tandem MS/MS, and data analysis were performed as described in the METHODS. Panel A, peptide sequences (bold) in the displayed sequence of human ceruloplasmin identified by tandem MS/MS; 11% of total sequence identified. Panel B, peptide sequences (bold) in the displayed sequence of human complement C3 identified by MS/MS; 16.75% of total sequence identified.

FIG. 8 illustrates that quantification of patient identifications (I.D.) for controls and lung cancer using ESI-MS.

FIG. 11 illustrates tandem mass spectrometry (MS/MS) identification of sera haptoglobin in JP-8 exposed rats. Tryptic digestion of the designated protein band in FIG. 10, ESI-ion trap MS/MS, and MS/MS data analysis were performed as described in the Materials and Methods. Panel A exhibits the amino acid sequence of *Rattus norvegicus* haptoglobin with the peptide sequences in bold identified in this study (38% total sequence identified). Panels B and C provide the MS/MS information on the identification of one of these peptides (bold and underline in panel A). B, the b-ion and y-ion series and resultant sequence of this peptide; C, MS/MS spectrum of this peptide. Proteins in FIGS. 12-14 were identified in a similar manner.

FIG. 12 illustrates a time-dependent increase in the levels of the acute-phase protein ceruloplasmin in response to dermal JP-8 exposure. Panel A, Coomassie-stained SDS gel of a protein band determined to be rat ceruloplasmin (see FIG. 11 legend) in three independent sera samples after seven days of exposure to JP-8 fuel. (−) lanes indicate acetone exposure and (+) lanes indicate JP-8 exposure. Panel B, densitometric quantification of the ceruloplasmin Coomassie band over a time-course of JP-8 dermal exposure (solid line) or acetone dermal exposure (broken line). *,** denote solid-line p values of 0.02 (n=3) and 0.018 (n=3) respectively, determined using the Student's t test.

DETAILED DESCRIPTION OF THE INVENTION

Figure 1:
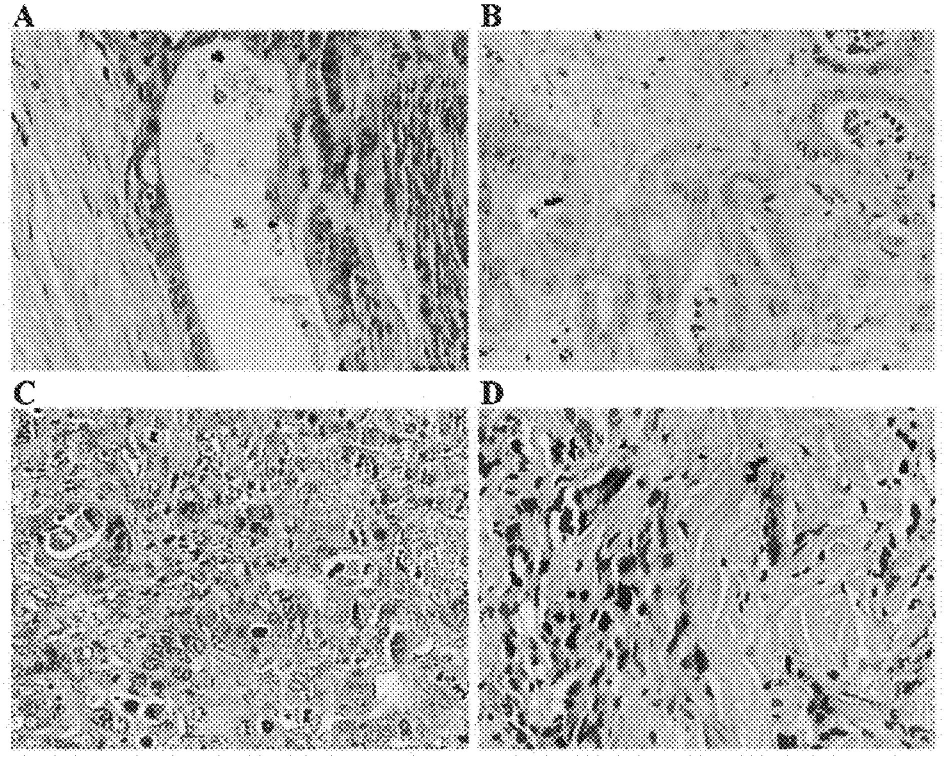
FIG. 1 illustrates histochemical (H & E) stained thin sections of human pancreatic adenocarcinoma. Tumors exhibited in panels A and B were located in the pancreas. Tumors in panels C and D were pancreatic cancers which metastasized to the liver and peritoneum, respectively.

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "surface-enhanced laser desorption/ionication" or "SELDI" refers to an MS technique performed by coating metal grids with affinity matrices and then binding proteins/peptides from biological fluids to these surfaces followed by laser desorption and mass determination of proteins/peptides. All of these steps have the potential for artifact introduction, especially with sample crystallization which is a random process that affects the ionization step in laser desorption MS. The SELDI technology involves prefractionation of sear followed by chemical addition and crystallization, and thus is a solid state analysis, which is much more difficult than an all liquid state analysis. In addition, this solid state analysis will require a much larger amount of sample than a liquid analysis would require.

The term "electrospray ionization" or "ESI" as used herein refers to a technique for directly spraying a solution of ions into a mass spectrometer. The technique is so gentle that only molecular ions, characteristic of the molecular weights of the compounds of interest, are seen. The technique of electrospray is therefore a method for "weighing" molecules in dilute solution. The structures of the detected ions can often be deduced from the electrospray spectrum. In the ESI technique, a dilute acidic solution of the macromolecule of interest is sprayed from a metal syringe needle at +5000 v, forming fine, highly charged droplets from which the solvent rapidly evaporates.

The term "time of flight" or "TOF" as used herein refers to a type of mass spectrometer in which molecular ions from an ion source are ejected by a laser flash or electrical pulse, and are separated by their speed of travel, which is inversely proportional to their mass-to-charge ratio.

The term "liquid biological sample" as used herein will be understood to refer to a sample of biological fluid. Biological samples include, but are not limited to, blood, plasma, serum, sputum, cerebrospinal fluid (CSF), tears, mucus, urine and the like.

The phrase "providing a liquid biological sample" as used herein refers to obtaining a biological sample for use in methods described in this invention. Most often, this will be done by removing a sample of cells from an animal, but can also be accomplished by using previously isolated cells (e.g., isolated by another person, at another time and/or for another purpose).

The term "polypeptide" as used herein is a generic term to refer to native protein, fragments, or analogs of a polypeptide sequence. Hence, native protein, fragments, and analogs are species of the polypeptide genus.

As applied to polypeptides, the term "substantial identity" means that two peptide sequences, when optimally aligned, such as by the programs GAP or BESTFIT using default gap weights, share at least 80 percent sequence identity, such as at least 90 percent sequence identity, or at least 95 percent sequence identity, or at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "metastasis" as used herein will be understood to refer to the spread of cancer from a primary tumor to other parts of the body. Metastasis is a sequential, multistep process in which tumor cells detach from a primary tumor, migrate through the basement membrane and extracellular matrix, and invade the lymphatic and/or blood systems. This is followed by the establishment of secondary tumors at distant sites.

The terms "disease", "disease state", and "disorder" as used herein, will be understood to include, but not be limited to, any acute or chronic pathological condition which could benefit from diagnosis and/or treatment.

The term patient includes human and veterinary subjects. "Mammal" for purposes of treatment refers to any animal classified as a mammal, including human, domestic and farm animals, nonhuman primates, and any other animal that has mammary tissue.

The term "healthy patient" as used herein will be understood to refer to a patient who is free of cancer. The term "healthy patient" may be used interchangeably herein with the terms "normal, noncancerous patient" and "control patient".

The term "series of statistically significant peaks" as used herein will be understood to refer to a collection or list of peaks or M/z values present in samples of a particular pathological state which represent the standard expectation of peaks or M/z values for the particular pathological state. In one embodiment, a series of statistically significant peaks includes a minimum of 20 peaks.

The terms "acute phase protein", "inflammatory protein", and "inflammation sensitive protein" will be understood to be used interchangeably herein, and refer to a class of proteins whose plasma concentrations increase (positive acute phase proteins) or decrease (negative acute phase proteins) in response to inflammation. Most disease states have inflammatory components. Examples of acute phase proteins that may be utilized in accordance with the present invention include, but are not limited to, Albumin, pre-albumin, apolipoprotein-A1 (apo-A1), apo-AII, apo-AIII, apo-AIV, Alpha 1-antichymotrypsin, Alpha 1-antitrypsin, Alpha-2-HS glycoprotein, Alpha-2-Macroglobulin, Alpha-2-antiplasmin, Calprotectin, C-reactive protein, Ceruloplasmin, Complement C2, C3, C4, C5, C9, B, C1 inhibitor, C4 binding protein, Factor VIII, Ferritin, Fibrin, fibrinogen, Haptoglobin, Hemopexin, Heme oxygenase, Heparin cofactor 11, Histidine-rich glycoprotein, Inter-alpha-trypsin inhibitor, Lactoferrin, Leukocyte protein 1, Lipoprotein (a), Lipopolysaccharide binding protein, Manganese superoxide dismutase, Manose binding protein, Orosomucoid ($\alpha$1-acid glycoprotein), Plasmin, Plasminogen activator inhibitor I, Serum tenascin C, Serum amyloid A, Serum amyloid P component, Thrombin, and Von Willebrand factor.

When the terms "one," "a," or "an" are used in this disclosure, they mean "at least one" or "one or more," unless otherwise indicated.

Numerous aspects and advantages of the invention will be apparent to those skilled in the art upon consideration of the following detailed description which provides illumination of the practice of the invention.

The present invention is directed to methods of identifying biomarkers in cancer or disease sera, as described in further detail herein below.

Pancreatic cancer diagnosis is often invasive, problematic, and costly. It is important to develop non-invasive, reliable, and cost-effective tests using small amounts of a readily available body fluid (such as but not limited to, serum) to assist the Pathologist, Oncologist and/or Surgeon in the diagnosis and treatment of cancer.

Toward this end, the present invention is related to identification of biomarkers in cancer or disease patients (including but not limited to, lung and pancreatic cancer patients) by serum profiling, a technique which utilizes mass spectrometry (MS) in the analysis and identification of potential biomarkers. Such biomarkers can also provide clues to carcinogenesis mechanisms. The presently disclosed and claimed invention demonstrates the utility of analyzing sera from cancer and disease patients for diagnostic and mechanistic purposes.

Current methods of serum profiling use SELDI-MS, which is a solid state analysis. However, the presently disclosed and claimed invention overcomes the disadvantages and defects of the SELDI-MS technology by utilizing liquid ESI-MS for serum profiling; such technique is able to distinguish low mass spectral peaks in cancer or disease sera from normal sera.

The presently disclosed and claimed invention is directed to a method of identifying biomarkers in liquid biological samples from cancer patients or patients having a particular disease state. The method includes the steps of: (a) providing a plurality of first liquid biological samples, wherein the plurality of first liquid biological samples are obtained from patients having the same type of cancer or a particular disease state; (b) providing a plurality of second liquid biological samples, wherein the plurality of second liquid biological samples are obtained from normal, healthy patients; (c) directly subjecting the plurality of first liquid biological samples and the plurality of second liquid biological samples to electrospray ionization mass spectrometry (ESI MS) to produce a mass spectrum profile for each liquid biological sample; (d) constructing a first database comprising peaks present in the mass spectrum profiles of the plurality of first liquid biological samples; (e) constructing a second database comprising peaks present in the mass spectrum profiles of the plurality of second liquid biological samples; (f) comparing the second database to the first database to identify at least one series of statistically significant peaks that distinguish the plurality of liquid biological samples obtained from cancer/disease patients from the plurality of liquid biological samples obtained from healthy patients; and (g) determining that the at least one series of statistically significant peaks identified in (f) comprise at least one biomarker related to the type of cancer or particular disease state.

In one embodiment, the at least one series of statistically significant peaks identified in step (f) above comprises at least one of: (a) at least one statistically significant peak present in the plurality of liquid biological samples obtained from cancer patients (or patients having a particular disease state) that is not present in the plurality of liquid biological samples obtained from healthy patients; (b) at least one statistically significant peak present in the plurality of liquid biological samples obtained from healthy patients that is not present in the plurality of liquid biological samples obtained from cancer patients (or patients having a particular disease state); (c) at least one statistically significant peak present in the plurality of liquid biological samples obtained from cancer patients (or patients having a particular disease state) that is present at an increased intensity and/or area when compared to the same peak in the plurality of liquid biological samples obtained from healthy patients; and (d) at least one statistically significant peak present in the plurality of liquid biological samples obtained from healthy patients that is present at an increased intensity and/or area when compared to the same peak in the plurality of liquid biological samples obtained from cancer patients (or patients having a particular disease state).

The at least one biomarker identified in step (g) may have a mass in the low mass region of between about 450 m/z and about 4000 m/z; in addition, the at least one series of statistically significant peaks may include a plurality of biomarkers therein, such as but not limited to, at least twenty biomarkers related to the type of cancer or a particular disease state.

In one embodiment, the mass spectrometry technique utilized in accordance with the presently disclosed and claimed invention is electrospray ionization-time of flight mass spectrometry (ESI-TOF MS).

Another embodiment of the presently disclosed invention includes a method of distinguishing between subtypes of cancer or stages of cancer. Such method includes the steps of: (a) providing a plurality of first liquid biological samples, wherein the plurality of first liquid biological samples are obtained from patients having the same type and subtype or stage of cancer; (b) providing a plurality of second liquid biological samples, wherein the plurality of second liquid biological samples are obtained from patients having the same type of cancer as the plurality of first liquid biological samples but a different subtype or stage of cancer; (c) providing a plurality of third liquid biological samples, wherein the plurality of third liquid biological samples are obtained from normal, healthy patients; (d) directly subjecting the plurality of first liquid biological samples, the plurality of second liquid biological samples and the plurality of third liquid biological samples to electrospray ionization mass spectrometry (ESI MS) to produce a mass spectrum profile for each liquid biological sample; (e) constructing a first database comprising peaks present in the mass spectrum profiles of the plurality of first liquid biological samples; (f) constructing a second database comprising peaks present in the mass spectrum profiles of the plurality of second liquid biological samples; (g) constructing a third database comprising peaks present in the mass spectrum profiles of the plurality of third liquid biological samples; (h) comparing the third database to the first and second databases to identify at least one series of statistically significant peaks that distinguish the plurality of liquid biological samples obtained from cancer patients from the plurality of liquid biological samples obtained from healthy patients; (i) determining that the at least one series of statistically significant peaks identified in (h) comprises at least one biomarker related to the type of cancer; (j) comparing the first database to the second database to identify at least one series of statistically significant peaks present in the plurality of liquid biological samples obtained from patients having one cancer subtype or stage that is not present in the plurality of liquid biological samples obtained from patients having another cancer subtype or stage; and (k) determining that the at least one series of statistically significant peaks identified in (j) comprises at least one biomarker related to a specific subtype or stage of cancer.

The at least one series of statistically significant peaks identified in step (h) may comprise at least one of: (a) at least one statistically significant peak present in the plurality of liquid biological samples obtained from cancer patients that is not present in the plurality of liquid biological samples obtained from healthy patients; (b) at least one statistically significant peak present in the plurality of liquid biological samples obtained from healthy patients that is not present in the plurality of liquid biological samples obtained from cancer patients; (c) at least one statistically significant peak present in the plurality of liquid biological samples obtained from cancer patients that is present at an increased intensity and/or area when compared to the same peak in the plurality of liquid biological samples obtained from healthy patients; and (d) at least one statistically significant peak present in the plurality of liquid biological samples obtained from healthy patients that is present at an increased intensity and/or area when compared to the same peak in the plurality of liquid biological samples obtained from cancer patients.

The at least one series of statistically significant peaks identified in step (j) may comprise at least one of: (a) at least one statistically significant peak present in the plurality of liquid biological samples obtained from patients having one cancer subtype or stage that is not present in the plurality of liquid biological samples obtained from patients having another cancer subtype or stage; and (b) at least one statistically significant peak present in the plurality of liquid biological samples obtained from patients having one cancer subtype or stage that is present at an increased intensity and/or area when compared to the same peak in the plurality of liquid biological samples obtained from patients having another cancer subtype or stage.

The plurality of first and second biological samples may be obtained from patients having any type of cancer, including but not limited to, pancreatic cancer patients, lung cancer patients, and the like.

The at least one biomarker identified in at least one of steps (i) and (k) may have a mass in the low mass region of between about 450 m/z and about 4000 m/z; in addition, the at least one series of statistically significant peaks identified in steps (h) and (j) may each include a plurality of biomarkers therein, such as but not limited to, at least twenty biomarkers related to the type of cancer. Also, the method of mass spectrometry may be electrospray ionization-time of flight mass spectrometry (ESI-TOF MS).

The presently disclosed and claimed invention is also directed to a method of serum profiling that utilizes gel electrophoresis to identify at least one acute phase protein that is up or down-regulated in a type of cancer or disease state. In this method, sera from a cancer or disease patient and sera from a healthy control patient are subjected to gel electrophoresis (such as but not limited to, SDS-PAGE, Western blot detection, immunofluorescence techniques, etc.), and a plurality of acute phase proteins that are substantially increased or decreased in the cancer or disease sera compared to the control sera are identified. The plurality of acute phase proteins may total at least 5 proteins, at least 10 proteins, at least 15 proteins, at least 20 proteins, at least 25 proteins, at least 30 proteins, at least 35 proteins, or at least 40 proteins.

The presently disclosed and claimed invention further includes a method of identifying biomarkers in a liquid biological sample from a patient suspected of having cancer or a disease state. The method includes the steps of: (a) providing a liquid biological sample obtained from a patient suspected of having cancer; (b) directly subjecting the first liquid biological sample to electrospray ionization mass spectrometry (ESI MS) to produce a mass spectrum profile for the liquid biological sample; (c) comparing the mass spectrum profile to the databases produced as described herein above; and (d) determining that the patient has cancer if at least one biomarker is identified as being present in the liquid biological sample.

Certain embodiments of the methods of the presently disclosed and claimed invention include the step(s) of constructing databases that comprise peaks present in the mass spectrum profiles of a plurality of liquid biological samples. This database construction offers an advantage over the previously published SELDI analysis techniques, as the data analysis procedure identifies mass spectral peaks prior to performing significance analysis. In the prior art SELDI technique, significance analysis was performed first, and this added variation to the system.

In one particular embodiment, the step of "constructing a database", as recited in the claims, involves compressing mass spectral data by summing M/z signal intensity into whole number units identified by rounding down M/z values. For example but not by way of limitation, M/z intensity values between the whole number steps between and including 500 and less than 501 would be summed and assigned an M/z value of 500. Data is normalized in a stepping normalization to total signal intensity of 25-50 M/z units from throughout the data range. For example by not by way of limitation, the summed Intensity of M/z value between 350 and 375 for each sample are normalized. The next step would normalize the sum Intensity of M/z value between 376 and 400 for each sample. The normalization steps continue until the M/z range is completed. Peaks are identified using software which automatically identifies peaks using valley to valley definitions. The information provided by the software includes descriptive values such as, but not limited to: peak range, peak Centroid, peak intensity, peak minimum M/Z, peak maximum M/z, and peak area.

Initial databases may be created by grouping similar information together by disease state (cancer, control, injury, etc.) and include relevant sample information, peak identifying characteristics, relevant statistical information and pathology or disease state information. The databases so constructed can then be compared to identify statistically relevant peaks which help identify the disease state. This comparison may include increased, diminished or absent peak values and M/z values. Once statistical relevant peaks have been identified, a pathology assignment is included in the database. The pathology assignment specifies the particular expected pathology variables and values which assigns the expected pathology for a sample containing the defined peak and when to assign the particular pathology. The value is dependent for each statistical test group (i.e., (control vs. general cancer) and (control vs. specific cancer)) would each have specific pathology and assignment values for each M/z tested (initial database construction requires knowledge of disease state).

For example but not by way of limitation, the test construction may include the following; values at each M/z peak for each sample are compared to the test group's (i.e., disease, control, etc.) database and each peak is assigned a pathology for each statistical test (each peak may be tested more than once depending on the number of tests which denoted statistical significant changes in peak values). The occurrence value for each pathology and sample is determined. The value observed divided by the maximum possible observations provides a percentage similarity value. Observations of range limitations for similarity percentages help define range limitations used in further testing. Cutoff values for each disease or test group are determined and set to help assign final pathology. Percentage range limitations are used to assign pathology to the sample if the cutoff value is satisfied. Cutoff test results indicate the samples' similarity identification or final pathology assignment.

The methods of the presently disclosed and claimed invention may be utilized to not only diagnose a condition, a particular subtype of the condition and/or its degree of severity, but can also be utilized to follow and assess the efficacy of treatment.

EXAMPLES

Examples are provided hereinbelow. However, the present invention is to be understood to not be limited in its application to the specific experimentation, results and laboratory procedures. Rather, the Examples are simply provided as one of various embodiments and are meant to be exemplary, not exhaustive.

Example 1

In 2006, pancreatic cancer is predicted to be the fourth leading cause of cancer deaths in the United States (32,300 versus 41, 430 for breast cancer and 27,350 for prostate cancer). The identification of cancer biomarkers has proven a useful strategy in the screening, early detection, and treatment of cancer. This is exemplified by the standard PSA (prostate specific antigen) blood test screen for prostatic cancer (Schroder et al., 1996). Pancreatic cancer is especially difficult to diagnose (due in part to the inaccessibility of the organ), which likely contributes to the high mortality rate of this disease (Jemal et al., 2003). Resection of the pancreatic tumor using the Whipple procedure is at present the most effective treatment of this disease, and for this procedure to be effective, the cancer must be detected at its early stage (Posteir et al., 2001). Smoking, alcohol use, and pancreatitis are some of the known risk factors for pancreatic cancer (Lowenfels et al., 1999; and Postier et al., 2003).

A number of protein biomarkers were identified in the sera, pancreatic juices, and tissues from pancreatic cancer patients. These include serum protein CA-19.9 (Gattani et al.), glutathione S-transferase (Ulrich et al., 2002; and Trachte et al., 2002), vascular endothelial growth factor (VEGF) (Trachte et al., 2002), and NF-κB (Wang et al., 1999). NF-κB is a major regulator of inflammation and its up-regulation in pancreatic cancer suggests key roles of inflammatory processes in the development of pancreatitis and pancreatic cancer. Mass spectrometry (MS) is the technical foundation of protein biomarker analysis, and its use is becoming more mandatory in cancer research (Chambers et al., 2000; and Verma et al., 2001). MALDI MS analysis (matrix-assisted laser desorption/ionization) was able to detect peptides/proteins present in normal sera but absent in sera from pancreatitis/pancreatic cancer patients (Valerio et al., 2001). Another use of mass spectrometry in cancer diagnostics is profiling of the small molecule, low molecular weight range (approximately 500 to 5000) of serum. This technology is based upon the concept that changes in the physiological state of the human body (e.g., by disease) are reflected by changes in biomarkers present in serum. This technology was previously used to help distinguish serum mass peak patterns for breast and prostate cancer (Li et al., 2002; and Ornstein et al., 2004).

In the presently disclosed and claimed invention, mass spectrometry approaches were used to identify biomarkers present in the sera of pancreatic cancer patients when compared to sera of normal individuals. At present, no blood test or any other reliable bodily fluid analysis is available for pancreatic cancer, especially in its early stages. The inventive concept disclosed and claimed herein provides the technology and assays necessary for accurate serum profiling/testing for pancreatic cancer. Such analyses will lead to earlier diagnosis and treatment of patients. A number of acute phase/inflammatory proteins have been identified herein (using gel electrophoresis and mass spectrometry) whose levels are increased in pancreatic cancer patients when compared to normal individuals. The presently disclosed and claimed invention has also identified, using electrospray ionization (ESI) mass spectrometry, heterogeneous groups of low molecular weight compounds (500-1500) in sera that correlate with pancreatic cancer patients versus healthy individuals.

Materials and Methods for Example 1

Pathological Analysis of Human Pancreatic Adenocarcinoma. Tumor sections (5 μm thick) from stage IIB and stage 1V (metastatic) pancreatic adenocarcinoma patients were stained with hematoxylin and eosin (H&E), and evaluated for morphologic abnormalities by a surgical pathologist (Dr. Stan Lightfoot). Pancreatic adenocarcinoma was indicated by abnormal glandular ducts and infiltrating fibrous tissue. Metastatic disease was indicated by tumor metastasis to other organs/tissues (liver and peritoneum). Pancreatic cancer staging (IIB[T1-3, N1, M0]-IV[any T, any N, M1) was determined from pancreatic tumor size (T), lymph node involvement (N), and tumor metastases (M).

Gel Electrophoresis of Sera Samples from Pancreatic Cancer Patients and Control Volunteers. Serum was obtained from whole blood by incubation at 4° C. for 45 min followed by centrifugation at 13,000 g for 2 min. Sera aliquots (50 μl) were frozen at −80° C. The protein concentrations of human sera were determined in triplicate using the Bradford protein assay (Bio-Rad, data not shown). Sera samples from pancreatic cancer patients as well as samples from healthy volunteers were heated at 95° C. for 10 min, and proteins were resolved by size using 10% SDS-polyacrylamide gel electrophoresis (PAGE) followed by Coomassie staining as described (Larabee et al., 2005). Quantification was performed by densitometry on gel bands from scanned images using the software package, UN-SCAN-IT Version 5.1 (Silk Scientific Inc., Orem, Utah). Statistical significance was determined by a two-tailed student's t-test. For all comparisons, a p value of <0.05 was used to designate a significant difference.

Protein Analysis of Human Pancreatic Cancer Sera and Normal Sera. Protein bands from SDS-PAGE were excised and destained with 40% MeOH-7.5% acetic acid, dehydrated in 100% MeOH, and then rehydrated in 70% methanol. Gel bands were further destained in a 30% acetonitrile solution containing 100 mM ammonium bicarbonate. The gel slice was then crushed and vacuum dried. Each slice was rehydrated in 50 mM ammonium bicarbonate containing 1 μg trypsin (Promega) and incubated overnight at 35° C. Peptide fragments were collected and combined from gel washes of 50, 75 and 95% acetonitrile in 5% formic acid. Desiccated peptides were suspended in 2% formic acid, 5% methanol, 2% acetonitrile and applied to a Vydac C18 100×0.150 mm HPLC column; peptides were eluted using a gradient of methanol containing 2% formic acid. MS/MS peptide sequencing was performed on a ThermoElectron LCQ electrospray-ion trap mass spectrometer. MS data was collected in the positive mode with a nano-ESI source (capillary temperature 200° C., source voltage of 1.70 KV, source current of 80.00 μamps and capillary voltage of 27 volts). Identification of peptide/protein sequences was performed using TurboSequest (ThermoElectron), version 3.0 software. Results from the NCBI (National Center for Biotechnology Information) database searches were checked against a common contaminant database. Individual data search files were limited to molecular weights between 150 and 6000, peptide mass tolerance of 1.5, fragment ion tolerance of 0.0, and ion cutoff percentage of 30% (minimum % match of actual to theoretical MS/MS ions). Protein searches using the peptide sequence identified the top X-correlation and were considered statistically significant when their Xcorr was 2.5 or greater. The trypsin identification inherent in the digests was 1.5 and above. A previous study using this methodology listed highly significant values of Xcorr ranging from 1.9 to 3.9 (Dittmer et al., 2002).

Electrospray Ionization-Mass Spectrometry (ESI-MS) of Sera from Human Pancreatic Cancer Patients and Healthy Controls. High-resolution mass spectra were generated using sera samples from pancreatic cancer patients and healthy controls in random fashion. For this study, sera from 13 pancreatic adenocarcinoma patients (age range from 44 to 79, stage range from IB[T2, N0,M0]-IV, 7 females and 6 males, and 12 healthy controls (age range 51 to 70, 6 females and 6 males) were subjected to ESI-MS analysis. Informed consent was obtained from all patients and volunteers used in these studies. The mass spectra were sampled at an m/z (mass divided by charge) resolution of 0.02 Daltons over a m/z range of 400 to 5000. Triplicate mass spectra for each serum sample were obtained by electrospray Ionization (ESI) mass spectrometry (Mariner System, Applied Biosystems, Foster City, Calif.). For ESI-MS, a serum sample was diluted 1 to 400 into a solution of 50% methanol and 2% formic acid and directly infused into the ESI source at a flow rate of 2 μl/min. Positive ion mode spectra were collected and averaged every 10 seconds and accumulated for 10 to 20 min for each injection. The instrument settings for ESI-MS were as follows: spray tip potential, 1612.50; nozzle potential, 61.04; skimmer 1 potential, 12.01; quad DC potential, 6.23; deflection voltage, 0.68; einzel lens potential, −30.00; quad RF voltage, 875.24; nozzle temperature, 195.01° C.; push pulse potential, 740.11; pull pulse potential, 359.82; pull bias potential, 6.00; accelerator potential, 3819.96; reflector potential, 1449.97; deflector potential, 2499.90.

Statistical Analysis of Human Sera Mass Spectra. Sera mass spectra were subjected to preprocessing steps to convert the high resolution data into a group of data points more easily compared between treatment groups. Because slight variances in the m/z (mass/charge) values of each peak may vary between sera samples, a linear two-point interpolation was used to provide sampling uniformity between samples at a resolution of 0.02 Dalton. Since the intensity values for each sample may vary in magnitude, the intensity values were also normalized. This normalization was done by summing all intensity values within the m/z range of 800 to 1500 for each sample. Using this summation value as the normalizing constant, all intensity values in each pattern were then divided by this constant to yield the relative intensity pattern for that sample. The resulting data set was further compressed by summing all intensity values within a particular m/z integer interval. For example, all intensity values from m/z values of 500.00 to 500.99 were summed and labeled as 500. An exemplar (cohort) of the sera patterns was created by summing all available patterns for both the cancer class and the normal class. Each peak was identified by a number sequentially assigned from one and was defined by the beginning valley location, the peak location, and the ending valley location, which was the beginning valley location for the next peak. The same set of valley locations were then applied to all samples. The maximum intensity within the interval between valleys was considered to be the relative intensity for that peak.

Each sample spectrum was represented by a set of relative intensity and m/z values associated with the peaks. To determine which peak was significant, a bootstrapping technique[19] was used to randomly divide in blinded fashion the training set into many subsets. Each subset contains roughly 80% of the spectra from the cancer class and roughly 80% from the normal class. For each subset, a Pearson's correlation coefficient was computed (Mathworks, Inc., 2002) from the relative intensities and m/z values of each individual peak from both classes. Based on the resultant correlation coefficients, the peaks were rank ordered. A total of 1000 subsets were created and processed. The sorted list identified the peaks that are most correlated with the discrimination between the cancer class and the normal class. To provide discrimination ability on the subsets, a linear regression (James et al., 1985) was performed using the relative intensities and m/z values of the sorted peaks from the training set by associating the cancer sample class with +1 and the healthy sample class with −1. Using the regression coefficients, a prediction was made for each sample in the training set. To test the efficacy of the discrimination power of the regression coefficients, random sets or sera spectra were processed in similar manners. To set the threshold for discrimination between the two sample classes, a Bayesian classifier (Samso et al., 2002) was used which balances the probability of error between the false positives and false negatives in the example.

Results for Example 1

Figure 2:
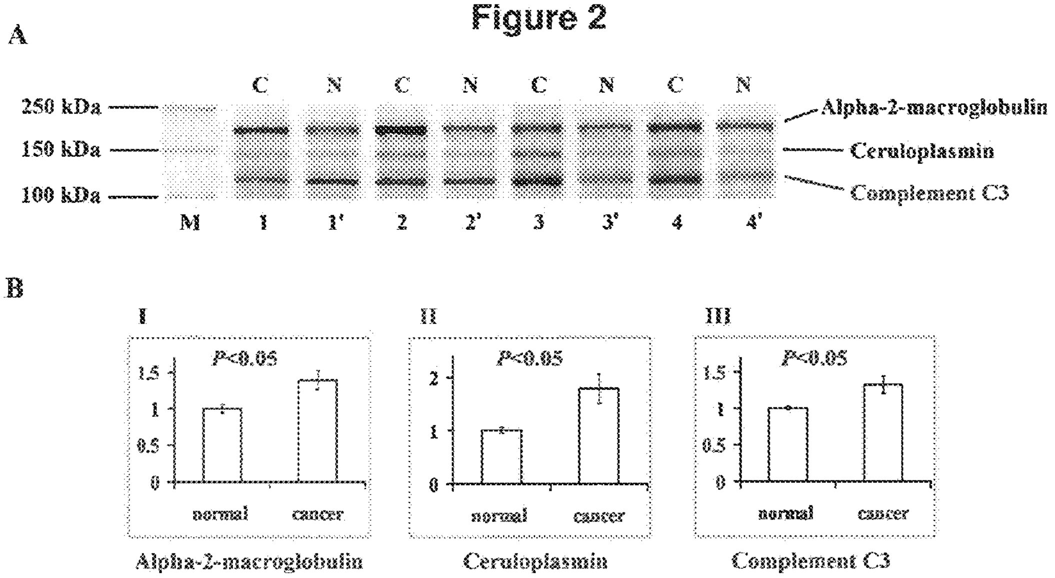
FIG. 2 illustrates the identification of protein biomarkers for human pancreatic cancer sera by SDS gel electrophoresis and tandem mass spectrometry (MS). Panel A exhibits an SDS gel panel of four healthy sera (N) and four cancer sera (C); the four cancer sera are from patients of the tumors exhibited in FIG. 1 (SDS gel lanes 1 and 2, panels A and B; lanes 3 and 4, panels C and D). Protein identifications are in the right margin; the far left lane contains the molecular mass markers (BioRad, #161-0373). Panel B is the quantification of three major Coomassie-stained band intensities in all the pancreatic cancer and normal sera in panel A. P values (<0.05) for quantitative differences in band intensities were determined using a standard t-Test.

Inflammatory Protein Biomarkers in the Sera of Pancreatic Cancer Patients. FIG. 1 exhibits the histology (hematoxylin and eosin staining, [H & E]) of pancreatic tumors (stages IIB-IV) from patients whose sera was used in subsequent gel electrophoresis studies to identify protein tumor biomarkers (FIG. 2). The tumor in panel A displays a chaotic picture of glandular elements. The cells lining the dilated ducts have irregular oval nuclei with large nucleoli, and the glands are surrounded by an irregular edematous stroma. In panel B, the tissue has a nodule of cancer and the glands are irregular. Both these tumors are primary in origin and are stage IIB. Tumors in panels C and D are pancreatic cancers (stage 1V) that have metastasized to the liver and peritoneum, respectively. Panel C exhibits liver cells in the upper portion and metastatic cancer in the lower portion. The liver cells look normal and the malignant cells are forming glandular structures and have similar characteristics as observed in panel A. In panel D, an infiltrate of malignant cells is seen within the peritoneum along with a fibroblastic area (elongated cells lacking nuclei in the middle of panel). Very poor glandular elements are seen in the neoplastic area in this panel and the cells have markedly reduced cytoplasm and irregular hyperchromatic nuclei.

The identification of proteins as up or down-regulated in various cancers can provide important biomarkers for diagnostics and give mechanistic clues about the carcinogenesis process which possibly can be exploited therapeutically. Exhibited in FIG. 2A is an SDS gel panel of high molecular mass proteins in the sera of four different pancreatic cancer patients (C, lanes 1-4) whose tumors are exhibited histologically in FIG. 1. Electrophoresed next to these cancer patient sera are sera from four different healthy controls (N, lanes 1'-4'). The three major bands present were subjected to tandem mass spectrometry protein sequence identification as described in the Materials and Methods of this Example.

Three major proteins were identified, □-2-macroglobulin (upper band), ceruloplasmin (middle band), and complement C3 (lower band). There were 30-40% more "hits" for all three major proteins in the cancer lanes versus the control lanes. Ceruloplasmin is observed to be elevated in the FIG. 2 panel of pancreatic cancer sera. This copper-containing oxidase protein was previously characterized as an acute phase or inflammation sensitive protein as are α2-macroglobulin, and complement C3 (ISPs) (Engstrom et al., 2004). The elevated presence of these three proteins in the sera of pancreatic cancer patients is consistent with the concept that pancreatic cancer has an inflammatory disease component. It is of interest that the two lower bands (ceruloplasmin and complement C3) appear elevated relative to α-2-macroglobulin in the sera from the two patients with metastasized tumors. This is evident by comparing the stage IIB sera in lanes 1 and 2, FIG. 2 (which correspond to patient tumors in FIG. 1, panels A and B, respectively) with stage 1V sera in lanes 3 and 4, FIG. 2 (which correspond to patient pancreatic metastatic tumors in FIG. 1, panels C and D, respectively). FIG. 3 exhibits the MS/MS sequences identified in α-2-macroglobulin (panel A, 13.7% of total sequence) as well as the important b-y ion series (panel B, successive peptide bond breaks from the amino and carboxyl ends respectively of one of the peptides), and one peptide MS/MS spectrum (panel C). FIG. 4 exhibits the MS/MS sequences identified in ceruloplasmin (panel A, 11% of sequence) and complement C3 (16.8% of sequence).

Figure 5:
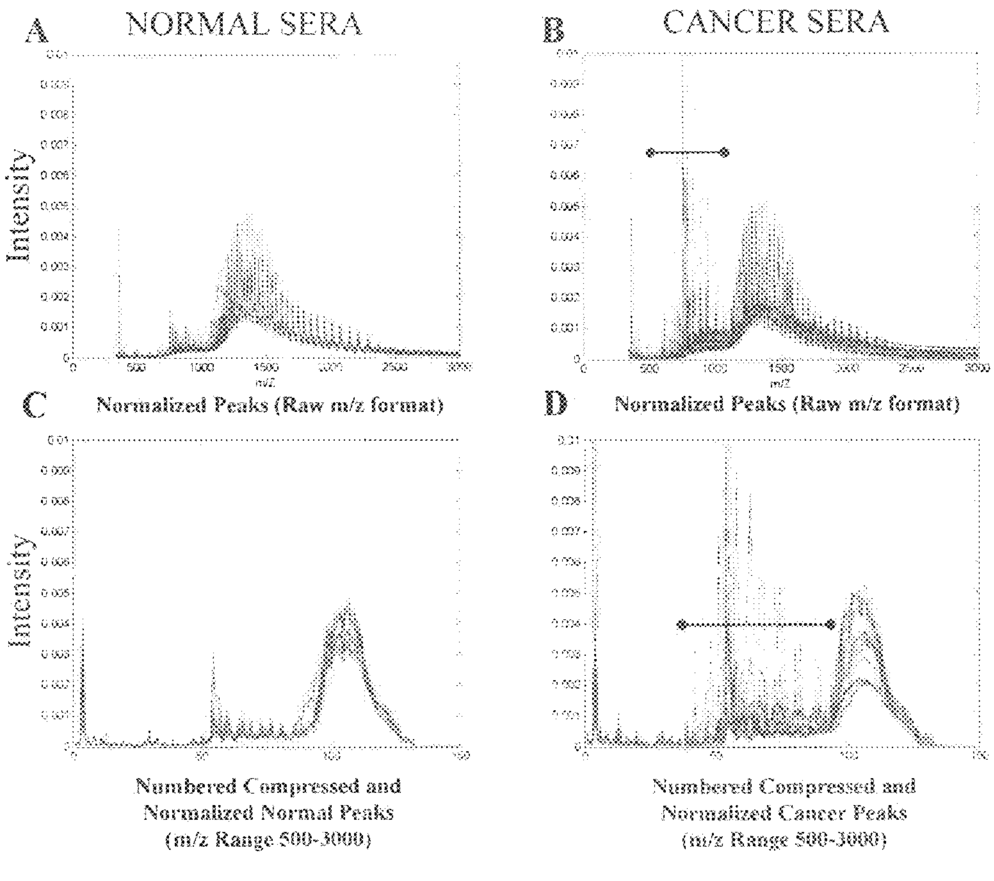
FIG. 5 illustrates high resolution, low-mass spectra of sera from pancreatic cancer patients or control volunteers. High resolution ESI-MS on sera samples was performed as described in the METHODS. Panels A and B are superimposed, normalized (peak intensity) spectra from 36 control serum scans and 40 pancreatic cancer serum scans, respectively. Panels C and D are numbered superimposed peaks (intensity normalized and m/z compressed) from 36 healthy control serum scans and 40 pancreatic cancer serum scans, respectively. The bars in both panels B and D denote the m/z regions of highest variability.

Serum Profile Heterogeneity Distinguishes Human Pancreatic Cancer Sera. Mass spectrometry profiling of sera and other bodily fluids has become a useful technique to catalog disease states and identify biomarker patterns, and holds promise for developing blood tests for various cancers including pancreatic cancer (Li et al., 2002; Richter et al., 1999; Semmes et al., 2005; and Yu et al., 2005). FIG. 5 exhibits ESI-MS experiments to distinguish serum mass profiles from 13 human pancreatic adenocarcinoma patient sera and 12 age and sex-matched human control sera. For this example, serum (upon 400-fold dilution) was applied to an ESI-time of flight-MS instrument to produce the mass spectrum profile for each serum sample. It is noted in panel B that many cancer peak differences (denoted by bar) exist in the 500-1200 m/z range when compared to the same region in the control spectra (A). The spectra in these panels exhibit 12 control and 13 cancer spectra, both performed in triplicate. Next, the normalized control and cancer peaks were compressed (intensity peaks were summed and assigned to an integer m/z value, panels C and D) which reduced the total number of peaks from several thousand to less than 150. This was performed to make the subsequent correlation coefficient and bootstrapping calculations more manageable. The reduced number of peaks in panels C and D from 1 to about 140 correlates to an approximate m/z range of 500 to 3000 in panels A and B.

For quantitative analysis, an individual Pearson's correlation coefficient was determined (described in the Materials and Methods section), based on the normalized relative intensity and mass/charge values for each of the peaks. The resultant correlation coefficients can be sorted to determine which peak is more significantly correlated with either pancreatic cancer or controls. As shown in Table 1, 20 peaks are significantly correlated (corr values) with pancreatic cancer or normal sera. At this point the correlation coefficients can be viewed as approximate percentages. That is, the correlation of 0.68 means approximately 68% of the normal samples had a peak of that mass to charge ratio (m/z, 1330) with the same intensity. If this intensity is removed from the correlation calculation, all these correlation coefficients would be in the 90% range. It is noted that the correlation coefficients for the 20 cancer peaks are smaller than the normal sera peaks. This indicates that the cancer sera are more heterogeneous with respect to the low mass profiles than the normal sera. Again this is indicated by the large variability seen in the 400-1200 mass region in the normalized cancer spectra (bar, panel B) when compared to panel A. In a blinded randomization process (bootstrapping, described in Materials and Methods section) of sample spectra, these 20 peaks and their correlation coefficients were subsequently utilized to identify pancreatic cancer versus control sera to the degree exhibited in Table 2. This methodology was able to distinguish cancer from normal sera 95% of the time in this blinded trial.

Figure 6:
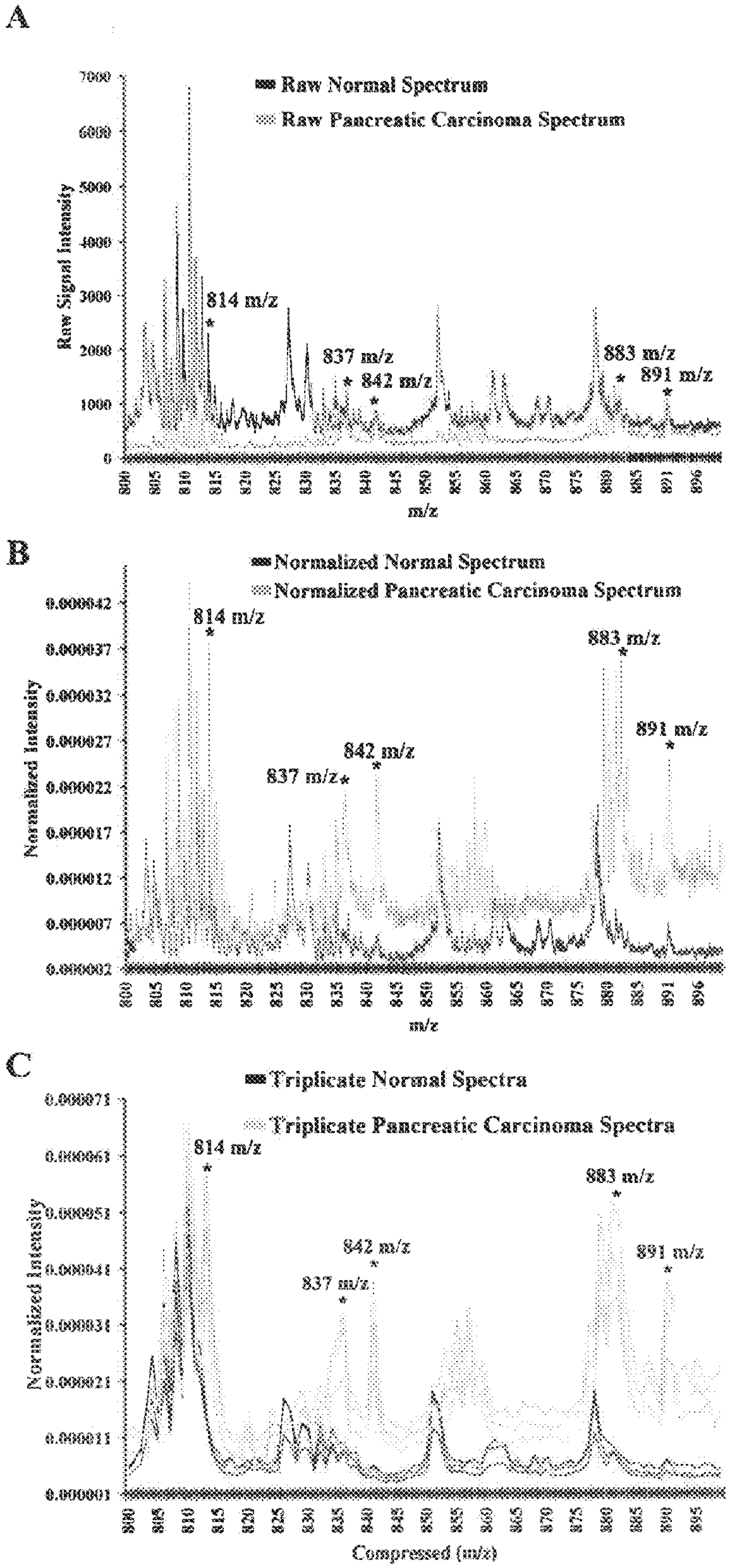
FIG. 6 illustrates the elucidation of pancreatic cancer m/z peaks from raw mass spectral data. ESI-MS of sera, peak intensity normalization and m/z compression were performed as described in the Methods. Panel A, raw mass spectra from a normal serum (dark grey line) and a pancreatic cancer serum (light grey line). Panel B, raw mass spectra from panel A normalized. Panel C, triplicate mass spectra from sera samples in panel A normalized and compressed. Five unique m/z peaks for pancreatic cancer sera identified in Table 1 are indicated with (*) in all panels.

Five low-mass peaks are present in pancreatic cancer sera but not in the normal sera in the 800-900 m/z range (Table 1). FIG. 6 exhibits a normal and a pancreatic cancer ESI mass spectrum in the "raw" data state (panel A), the normalized state (panel B), and the normalized and compressed data state (panel C). The five low-mass peaks in Table 1 are readily observed and retained during this data processing. This observation provides congruity between the statistical analysis used to identify low-mass peaks of correlative value for pancreatic cancer (Table 1) and the peaks present in the actual mass spectra.

TABLE 1

Identification of Biomarker Mass Peaks in the Sera of Human Pancreatic Cancer Patients

| Normal Sera | | | Cancer Sera | | |
|---|---|---|---|---|---|
| Rank | m/z | corr | Rank | m/z | corr |
| 1 | 1330 | 0.68 | 1 | 1569 | 0.52 |
| 2 | 1665 | 0.67 | 2 | 814* | 0.49 |
| 3 | 1304 | 0.66 | 3 | 762 | 0.46 |
| 4 | 1167 | 0.59 | 4 | 883* | 0.46 |
| 5 | 1279 | 0.59 | 5 | 1010 | 0.45 |
| 6 | 1255 | 0.59 | 6 | 947 | 0.45 |
| 7 | 1209 | 0.58 | 7 | 993 | 0.44 |
| 8 | 1623 | 0.58 | 8 | 891* | 0.43 |
| 9 | 1338 | 0.57 | 9 | 1222 | 0.43 |
| 10 | 1480 | 0.56 | 10 | 842* | 0.43 |
| 11 | 1415 | 0.56 | 11 | 761 | 0.42 |
| 12 | 521 | 0.55 | 12 | 935 | 0.41 |
| 13 | 1357 | 0.55 | 13 | 837* | 0.41 |
| 14 | 1479 | 0.55 | 14 | 1135 | 0.41 |
| 15 | 1188 | 0.54 | 15 | 617 | 0.40 |
| 16 | 497 | 0.54 | 16 | 1082 | 0.40 |
| 17 | 1287 | 0.53 | 17 | 798 | 0.40 |
| 18 | 1585 | 0.53 | 18 | 689 | 0.39 |
| 19 | 1232 | 0.52 | 19 | 795 | 0.39 |
| 20 | 1547 | 0.51 | 20 | 789 | 0.38 |

m/z: mass of a molecule divided by the unit charge of the molecule.
corr: Pearson's correlation coefficient[20]
*m/z values identified in FIG. 6

TABLE 2

Serum Profiling of Human Pancreatic Cancer and Normal Sera Spectra from Blinded Training Data

| Sample Identification | Spectra Identified/ Tested | Patient Identified/ Tested | Correctly Identified Spectra (%) | Correctly Identified Patients (%) |
|---|---|---|---|---|
| Non-Cancerous identified as non-Cancerous: | 36/36[a] | 12/12 | 100% | 100% |
| Cancerous identified as Cancerous: | 38/40[b] | 12/13 | 95% | 92% |
| Non-Cancerous identified as | 0/36 | 0/12 | 0% | 0% |

TABLE 2-continued

Serum Profiling of Human Pancreatic Cancer and Normal Sera Spectra from Blinded Training Data

| Sample Identification | Spectra Identified/ Tested | Patient Identified/ Tested | Correctly Identified Spectra (%) | Correctly Identified Patients (%) |
|---|---|---|---|---|
| Cancerous | | | | |
| Cancerous identified as non-Cancerous | 2/40 | 1/13 | 5% | 8.3% |

[a]12 control serum samples were scanned 3 times using ESI-MS.

[b]12 pancreatic cancer serum samples were scanned 3 times and 1 cancer serum sample was scanned 4 times.

Discussion for Example 1

In the present example of the disclosed and claimed invention, three acute phase or inflammation sensitive proteins (ISPs) were observed increased in the sera of pancreatic cancer patients (complement C3, α-2-macroglobulin, and ceruloplasmin, FIG. 2). Although the increases were not large, they were significant to a p value $<0.05$. Other acute phase response proteins previously found elevated in pancreatic cancer patients include serum amyloid A, α-1-antitrypsin, α-1-antichymotrypsin, and inter-α-trypsin inhibitor (Trachte et al., 2002; and Koomen et al., 2005). The elevation observed in the presently disclosed and claimed invention of the complement C3 protein in sera from pancreatic cancer patients is of interest because this protein is known to be a key regulator of inflammatory responses (Szalai et al., 2000). Inflammation is hypothesized to play a key role in pancreatic cancer development. For example, NF-κB, another major regulator of inflammation, is up-regulated in pancreatic cancer and pancreatitis tissues, which indicates that inflammatory processes have a role in the development of pancreatitis and pancreatic cancer (Wang et al., 1999). Histological evidence exists that pancreatitis (inflammation of the pancreas) is a potential precursor for pancreatic cancer in an experimental pancreatic cancer animal system (Postier et al., 2003). NF-κB and complement C3 stimulate inflammatory processes, which indicates that their elevation has causal roles in pancreatic cancer development as opposed to being a secondary effect from the cancer condition.

The other two acute phase proteins observed elevated in pancreatic cancer sera are α2-macroglobulin and ceruloplasmin. α2-macroglobulin is an anti-proteinase and was previously found complexed with trypsin in the sera of pancreatic cancer patients (Nakae et al., 1991). There are studies indicating that this protein may also have a role in cell spreading (Ikari et al., 2000). mRNA for this protein was previously observed elevated in pancreatic tumor tissue relative to adjacent normal tissue (Tan et al., 2003). Ceruloplasmin, a copper-binding oxidase, is also observed elevated in this panel of pancreatic cancer sera proteins (FIG. 2). Ceruloplasmin was observed to be elevated in ovarian cancer (Lee et al., 2004). Elevated amounts of this protein would suggest that pancreatic cancer might be susceptible to chemical agents that disrupt copper homeostasis like ammonium tetrathiomolybdate, which has efficacy against some cancers (Teknos et al., 2005). The increased presence of these three proteins in the sera of pancreatic cancer patients is consistent with the overall hypothesis that pancreatic cancer has an inflammatory disease component. Tobacco smoke and alcohol are known risk agents for pancreatic cancer (Lowenfels et al., 1999; and Postier et al., 2003). These agents could be inducing inflammation events in the pancreas mediated by NF-κB, complement C3, and other inflammatory proteins.

In this example of the presently disclosed and claimed invention, the low mass regions of a cohort of control sera (n=12) and sera from pancreatic cancer patients (n=13) were analyzed in triplicate by electrospray ionization (ESI) mass spectrometry (MS). The resulting spectra were subjected to preprocessing involving intensity normalization and m/z compression and then analyzed by Pearson's correlation and bootstrapping statistical techniques which expand the original numbers (Zharkikh et al., 1992). A 95% success rate was achieved in distinguishing pancreatic cancer sera mass spectra from control sera spectra and a 100% success rate was achieved in distinguishing control sera spectra from pancreatic cancer sera spectra (see Table 2). This example is the first serum profiling analysis of pancreatic cancer using ESI-MS technology. Most other cancer studies of this nature employ SELDI analysis (surface enhanced laser desorption/ionization). ESI-MS has several advantages over SELDI analysis for these types of assays. SELDI-MS involves equilibrating dilute sera with a surface matrix followed by several washing procedures of the matrix. The surface matrix, which has chemical additives added to aid in the subsequent ionization process, is then dried resulting in a random crystalline state. Laser desorption from such a crystalline state is dependent upon the chemical nature and structural randomness of the crystals. Such processes introduce variability and other unknowns into the total analytical procedure. ESI-MS is a completely liquid analysis requiring minimal sample manipulation. Also, biomolecules other than peptides can be analyzed and their structures can be determined using tandem MS.

In the serum profiling assays of the presently disclosed and claimed invention, more sera variability was found from pancreatic cancer patents than from control volunteers. For example, in the approximate 500-1200 m/z range in FIG. 5, the pancreatic cancer sera panel (B) has much more and much higher m/z intensity values than the similar mass region in normal sera (panel A). Variability between the same tumor types from different individuals is observed at the DNA level, as is the case with breast cancer DNA heterogeneity for example.[34] The presently disclosed and claimed invention extends this variability to the phenotypic level, i.e., the small molecule patterns in sera. This small molecule variability in pancreatic cancer sera could be due to increased proteolysis. This variability in pancreatic cancer sera versus control sera is also evident in the Pearson's correlation coefficients. When comparing m/z values found in either normal sera or pancreatic cancer sera (Table 1, panel A), it is evident that the distinguishing peaks in the normal sera have higher correlation values than the peaks in the cancer sera. This indicates that the control group as a whole is more homogeneous than the cancer group. It is also evident from this correlation data that the cancer sera has more distinguishing m/z values in the approximate 500-1200 range described above (19 out of 20) than the control data (6 out of 20). Again this is consistent with the general observation that the 500-1200 low mass region in sera is more variable in pancreatic cancer patients than in normal individuals. The appearance of such variability in pancreatic cancer sera (e.g., Table 1 and FIG. 6) is of interest because it may serve as an aid in the process of individualized diagnosis, which is a prerequisite of individualized therapy. In addition, some of the peaks/molecules appearing in the sera from pancreatic cancer patients likely are present at earlier stages of the disease, as these pancreatic cancer sera represent stages IB-IV of the disease. Such stage comparisons will be explored in future studies.

Example 2

Lung and pancreatic cancers have low 5-year survival rates (2-5%) because tests for early clinical stages of these diseases are not available (Greenberg et al., 2007). Development of such tests using peripheral blood samples will have major clinical and societal impacts. Tobacco smoking is a major risk factor for both these diseases, and the smoking population (direct and second-hand) would be a major group that would benefit from such testing. The commercial potential of such testing is therefore considerable not only for these cancers but also for other cancers and diseases as well. The presently disclosed and claimed invention has developed assays that will aid in the early diagnosis of lung and pancreatic cancers. These procedures, unique in the cancer biomarker field, are based on the use of electrospray ionization (ESI) mass spectrometry (MS) of serum. The present example illustrates that the presently disclosed and claimed invention obtains remarkable results distinguishing different carcinomas of the lung at early clinical stages from controls.

Human sera is a complex mixture of biomolecules including proteins, peptides, sugars, carbohydrates, lipids, nucleic acids, and other organic and inorganic compounds (Richter et al., 1999). The organs and tissues in human bodies are constantly shedding/secreting these biomolecules in response to environmental/physiological changes (Villanueva et al., 2006). Trying to make physiological sense out of such a changing mixture is a daunting task. The presently disclosed and claimed invention deciphers the complex biomolecular mixtures/patterns in human cancer sera, such as but not limited to, lung and pancreatic cancer sera, using an all-liquid electrospray ionization (ESI) mass spectrometry (MS) in order to identify/distinguish different physiological states, i.e. diseases. Previously the cancer biomarker field has relied exclusively on MALDI/SELDI (matrix-assisted laser desorption ionization/surface-enhanced laser desorption ionization) MS analysis for low-mass profiling of sera, which utilizes a completely different physics and chemistry than ESI-MS and introduces analytical variability in the analysis (Sorace et al., 203; and Semmes et al., 2005). In addition, the presently disclosed and claimed invention has significant applications for individualized diagnosis, treatment, and ameliorative care of patients with various cancers and other diseases as well. The future of cancer treatment will rely on "personalized medicine," and patients entering a treatment program will be analyzed by their unique molecular profile in addition to their type of tumor. No present methodology exists to solve the problems addressed by the presently disclosed and claimed invention (Yang et al., 2005).

The development of methodology to detect lung and pancreatic cancer in their more curable early stages (clinical stage I/II) is of paramount importance. The presently disclosed and claimed invention provides novel approaches for early detection of lung or pancreatic cancer in order to aid in diagnosis and treatment. The presently disclosed and claimed invention includes, but is not limited to, blood tests for early detection of human lung and pancreatic cancer using the novel approach of electrospray-ionization mass spectrometry (ESI-MS) of lung and pancreatic cancer serum. The all-liquid ESI-MS analysis employed in the presently disclosed and claimed invention offers significant advantages over the more commonly used random crystal-state MALDI/SELDI MS analysis for these types of procedures. In addition, the data analytical procedure of the presently disclosed and claimed invention identifies mass spectral peaks first and then performs significance analysis versus the other way around which adds variation to previously published SELDI studies (Sorace et al., 2003). Thus, the presently disclosed and claimed invention will foster individualized care for the lung or pancreatic cancer patient.

Materials and Methods for Example 2

Electrospray ionization-time of flight mass spectrometry (ESI-TOF MS) of disease and control sera. Serum was obtained from whole blood by incubation at 4° C. for 45 min followed by centrifugation at 13,000 g for 2 min to remove the clot. Sera aliquots (50 μl) were frozen at −80° C. and aliquots not reused after freezing and thawing. For ESI-MS, a serum sample was diluted 1 to 400 into a solution of 50% methanol and 2% formic acid and directly infused into the ESI source at a flow rate of 2 μl/min. High-resolution mass spectra were collected from three disease and three control sera in random fashion per day. The spectra was sampled at an m/z (mass divided by charge) resolution of two hundredths over an m/z range of 400 to 8000. Triplicate mass spectra for each serum sample were obtained by ESI time-of-flight (TOF) mass spectrometry (ThermoFisher). Positive ion mode spectra was collected and averaged every 10 seconds and accumulated for 10 to 20 min for each injection. The instrument settings for ESI-MS were as follows: spray tip potential, 1612.50; nozzle potential, 61.04; skimmer 1 potential, 12.01; quad DC potential, 6.23; deflection voltage, 0.68; einzel lens potential, −30.00; quad RF voltage, 875.24; nozzle temperature, 195.01° C.; push pulse potential, 740.11; pull pulse potential, 359.82; pull bias potential, 6.00; accelerator potential, 3819.96; reflector potential, 1449.97; deflector potential, 2499.90.

Electrospray ionization-ion trap mass spectrometry (ESI-ion trap MS) of disease and control sera. The ThermoFisher LCQ ADVANTAGAE Serum Profiling Procedure followed the standards set with the Mariner Mass spectrometer. Initial 1/400 dilution of sample in 2% formic acid 50% methanol and sample flow of 0.5 ul/min. LCQ settings for nano-spray profiling of serum: Source Voltage 1.72(kV), Source Current 0.78(μA), Sheath/Aux/Sweep Gas Flow=0, Capillary Voltage 27.81(V), Capillary Temp 200.10(C), Tube Lens Voltage, set potential 34.00(V). Data acquisition included 5 minute initial baseline prior to injection, injection and a stable interval of 10-15 min after the sample injection. Data was then exported and processed identical to the previous methods.

Treatments and statistical analyses of ESI-MS serum spectra data streams. Raw spectral trace data from either the ThermoFisher Mariner ESI-TOF or ThermoFisher LCQ Advantage ion trap mass spectrometers was extracted using the Mariner ESI-MS (ThermoFisher) Data Explorer software package. Spectral Data was exported in a format providing (m/z value) and intensity values. The (m/z values) was compressed into whole number units using a round down sum. The sum of intensities between m/z=120.000 and m/z=120.9999 . . . ] equaled the compressed intensity value for m/z=120.000. This compression was applied through the entire range of acquired data for each data set. Data was normalized in segments of 100(m/z) from 350-4000(m/z) then in segments of 1000 (m/z) from 4000-8000 (m/z). MS spectral peak Identification, which resulted in a centroid m/z peak area value being assigned to each peak, was performed using Data Explorer (ThermoFisher) using the following settings: Data Explorer settings: Mass Resolution(5000), % Peak Intensity(0), % Max Peak Area(0), Valley to baseline setting. Mass spectral peaks identified were exported to Excel for statistical processing. Peak areas identified by centroid (m/z) were placed into pathological groups: (control, cancer, squamous, and adeno) then tested for significance using the Student-t-test (paired, two-sample unequal variance). The tests include control vs. cancer, control vs. adenocarcinoma, control vs. squamous, squamous vs. cancer, and adenocarcinoma vs. cancer, as pathological pairs. A pathological peak list was created from the peak centroids identified as significant (p-values <0.05 was considered significant), and the top 159 peaks were scored to establish a significant pathological relationship for any particular serum. The pathological peak list contained the top 160 m/z values determined significant for each pathological pair.

The pathological scoring of peaks utilized the comparison of a group averages to the pathological pairs used in the statistical determination (see Table 3). Primary pathology for a peak was assigned to the pathology with the highest average compared to the paired average. The secondary pathology assignment was assigned to the pathology with the lowest average compared to the paired average. The individual serum peak list for each injection was then compared to the pathology peak list and the pathology pair average and assigned a pathology value. The comparison of injection peaks to the pathology peak list was performed in a similar fashion to the original pathology assignment. The injection peak was compared to the pathology pair average for any test pair at each m/z peak identified. Injection values higher than the average pair were assigned primary peak pathology with values less than the pathology pair assigned secondary peak pathology. The sum of each group was determined (cancer, squamous, adenocarcinoma, control) and compared to the total possible peak identifications for each group within the test series (peak n=940 for adenocarcinoma; n=1421 for squamous; n=1627 for control; n=1236 for cancer). This resulted in a percentage of total identification for the test series which provides a general pathology identity for each injection tested.

TABLE 3

Pathology Grouping by m/z Centroid Peak Value

| Mass Spectral Peak Centroid (m/z) | Pathology Group 1 (Control group is preferentially used as Group 1 if control present) | Pathology Group 2 | Pathology Group 1 and Group 2 Average |
|---|---|---|---|
| m/z(1) | Peak Area Value 1 | Value 2 | Value 3 (*Pathology determined by comparison) |

*If (Value 1) < (value 3) then Pathology assignment belongs to (Group 2) otherwise the Pathology assignment belongs to (Group 1).

Results for Example 2

Figure 7:
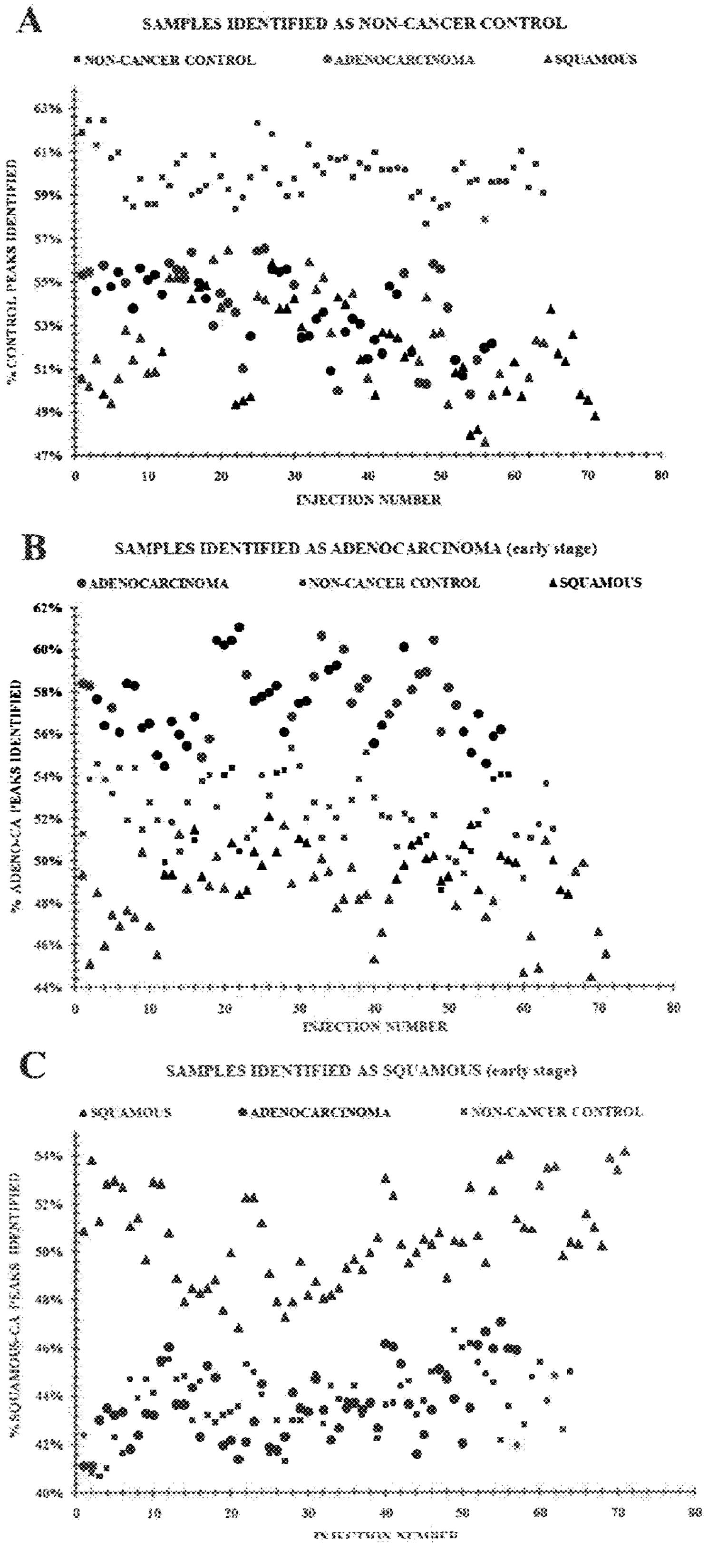
FIG. 7 illustrates the quantitative distinction of patient sera samples with early-clinical stage subtypes of lung cancer from control sera samples.

FIG. 7 illustrates results from ESI-MS experiments in which sera samples from 43 human lung cancer patients were distinguished from 22 age-matched human controls. For these studies, serum (400-fold dilution) was applied to an ESI-time of flight-MS instrument to produce the mass spectrum profile for each serum sample. To analyze the raw mass spectral data, preprocessing steps (normalization and compression) were performed as described in Example 1 and in the Materials and Methods section. It was possible to identify a group of m/z (mass divided by charge) peaks that are differentially present at p<0.05 in sera from control individuals versus adenocarcinoma and squamous cell lung cancer (CA) patients (Panel A), from individuals with stage I/II lung adenocarcinoma versus control and squamous cell lung cancer patients (Panel B), and from individuals with stage I/II lung squamous cell carcinoma versus control and adenocarcinoma lung cancer patients (Panel C). This result is not due to a smoking affect, as the number of smokers in the adenocarcinoma group is about equal to the number of smokers in the squamous cell group, and both are about twice that of the control group. This data was generated using the "two replicates per run, two runs per day over twenty days" rule of the National Committee for Clinical Laboratory Standards (2004). The data presented in FIG. 7 is a remarkable achievement as no other data presented in the cancer serum biomarker field has been able to distinguish 1) controls from early stage I/II cancers, and distinguish 2) cancer sub-types (adenocarcinoma and squamous) from a specific cancer type (lung).

FIG. 8 illustrates the success rate (%) with respect to correctly predicting sera assignments in blinded fashion for different tumor classifications (controls, lung adenocarcinomas, lung squamous cell carcinomas, and total cancers (adeno plus squamous) using the peak discrimination methodology depicted in FIG. 8. The correct patient assignment percentages ranged from 100 for the lung adenocarcinomas (lung CA) to 91.7% for controls. Not indicated in the table is the fact that a large number of significant m/z peaks were gleaned to obtain this information (ranging from about 800 for the controls to about 300 for the lung cancer group as a whole). By contrast, a previous study analyzing lung cancer biomarkers had a sensitivity of 79.1% in the detection of lung cancers in stages I/II (Yang et al., 2005).

The sensitivity of selected biomarkers in predicting early stage lung cancer was at least 97.7% (power value approximated to 0.98), while the percentage of samples tested negative from patients who do not have cancer was found to be 91.3% (21 out of 23). To calculate the size of a population N that needs to be tested to give true significance, the equation $\delta=d(N)^{1/2}$ was used, where δ (delta) is obtained from a standard power table using an α value (false positive rate of 0.08-approximated here to 0.1) which yields a δ value for this calculation of 3.6. A d value of 0.5 was used, which is indicative of a medium size effect of the measurements. Using these values, the calculated N value for these experiments is 52 (the patient numbers needed to attain true significance in each of the patient sub-classes). When analyzing patient samples, a standard for attaining clinical significance is the analysis of 100 patients for each class. Thus, the biomarkers used in this example exhibited an excellent predictive model (N=52) for use as a screening test for early-stage lung cancer.

Figure 9:
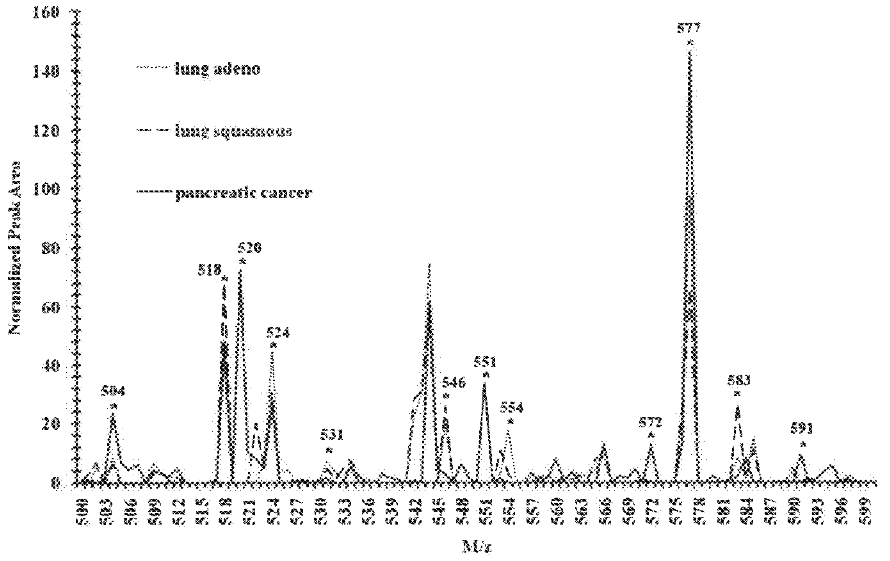
FIG. 9 graphically depicts ESI-MS spectra that demonstrate that there are different significant peaks between lung cancer and pancreatic cancer.

The presently disclosed and claimed invention has developed blood tests for early detection of lung and pancreatic cancer; these tests can be used for clinical testing of sera from patents who smoke, have congestive and gastric distress, pancreatitis, and other risk factors for lung and pancreatic cancer including family history. One step in this development process was the determination of the specificity of these electrospray ionization (ESI)-MS sera assays with respect to lung cancer and pancreatic cancer. FIG. 9 exhibits the determination of spectral m/z peak differences between lung and pancreatic cancer spectra. This figure displays the differences and similarities of significant m/z peaks (p<0.05) in a narrow 500-599 m/z range of an ESI-MS spectrum between lung and pancreatic cancers.

Major differences include m/z peaks at 504, 520, and 551. Thus, not only is the ESI-MS serum profiling paradigm of the presently disclosed and claimed invention able to distinguish controls from a cancer in early clinical stages as well as sub-types of that cancer (FIG. 7), but this paradigm is also able to distinguish different types of cancer all together (FIG. 9). This is a remarkable achievement as no other data presented in the cancer serum biomarker field has been able to make such claims.

Table 4 illustrates the top 100 observed lung cancer peaks showing significant differences from control sera peaks.

TABLE 4

OBSERVED LUNG CANCER SERA PEAKS SHOWING SIGNIFICANT DIFFERENCES FROM CONTROL SERA PEAKS

| | CANCER | | SQUAMOUS | | ADENO | |
|---|---|---|---|---|---|---|
| RANK top 100 | M/z | TTEST | M/z | TTEST | M/z | TTEST |
| 1 | 496 | 1.23278E−12 | 496 | 1.21897E−11 | 534 | 1.01479E−10 |
| 2 | 1547 | 6.17531E−10 | 758 | 2.67951E−11 | 1357 | 1.24126E−09 |
| 3 | 387 | 3.20229E−09 | 759 | 5.19471E−11 | 1547 | 3.16341E−09 |
| 4 | 489 | 1.61706E−08 | 563 | 4.83805E−09 | 2416 | 3.66525E−08 |
| 5 | 563 | 4.93695E−08 | 489 | 5.13003E−08 | 1209 | 1.68581E−07 |
| 6 | 592 | 1.00191E−07 | 565 | 5.92424E−08 | 475 | 1.73535E−07 |
| 7 | 534 | 1.15799E−07 | 592 | 1.28767E−07 | 563 | 1.76094E−07 |
| 8 | 1209 | 1.96196E−07 | 585 | 1.4942E−07 | 1304 | 3.0648E−07 |
| 9 | 758 | 2.27885E−07 | 475 | 2.51274E−07 | 387 | 3.26094E−07 |
| 10 | 585 | 2.94473E−07 | 878 | 3.13951E−07 | 503 | 6.11131E−07 |
| 11 | 2416 | 3.36075E−07 | 1547 | 3.49527E−07 | 1330 | 6.40555E−07 |
| 12 | 733 | 4.48232E−07 | 411 | 8.42308E−07 | 1415 | 8.22855E−07 |
| 13 | 878 | 5.34951E−07 | 733 | 8.87976E−07 | 611 | 9.72108E−07 |
| 14 | 759 | 6.09692E−07 | 524 | 1.41698E−06 | 2381 | 1.20224E−06 |
| 15 | 475 | 7.45114E−07 | 1209 | 2.33816E−06 | 1072 | 1.34011E−06 |
| 16 | 565 | 7.83175E−07 | 534 | 2.83742E−06 | 542 | 1.61987E−06 |
| 17 | 411 | 8.36394E−07 | 387 | 3.20025E−06 | 928 | 2.09439E−06 |
| 18 | 613 | 9.01897E−07 | 906 | 3.8289E−06 | 554 | 3.06668E−06 |
| 19 | 1357 | 1.06435E−06 | 2017 | 4.10543E−06 | 1105 | 4.66596E−06 |
| 20 | 2381 | 1.62143E−06 | 613 | 4.61227E−06 | 592 | 5.64363E−06 |
| 21 | 1478 | 1.88637E−06 | 1959 | 7.71475E−06 | 482 | 5.82138E−06 |
| 22 | 542 | 3.77112E−06 | 1057 | 8.09492E−06 | 2149 | 6.45074E−06 |
| 23 | 503 | 4.89858E−06 | 1478 | 9.58005E−06 | 496 | 7.31946E−06 |
| 24 | 1091 | 4.9348E−06 | 1623 | 1.02293E−05 | 878 | 1.21942E−05 |
| 25 | 1057 | 5.02677E−06 | 505 | 1.13423E−05 | 1958 | 1.86096E−05 |
| 26 | 590 | 6.16999E−06 | 1179 | 1.66579E−05 | 2220 | 2.11748E−05 |
| 27 | 554 | 7.53482E−06 | 503 | 1.67488E−05 | 535 | 3.05963E−05 |
| 28 | 369 | 9.37936E−06 | 3448 | 2.10301E−05 | 405 | 3.60677E−05 |
| 29 | 1304 | 1.08632E−05 | 352 | 2.81671E−05 | 2081 | 4.53842E−05 |
| 30 | 1105 | 1.10458E−05 | 1903 | 3.19919E−05 | 2083 | 4.62824E−05 |
| 31 | 543 | 1.46316E−05 | 2080 | 3.70005E−05 | 869 | 5.89006E−05 |
| 32 | 582 | 1.54543E−05 | 772 | 4.37168E−05 | 481 | 6.14696E−05 |
| 33 | 1073 | 1.92044E−05 | 2585 | 4.84261E−05 | 1623 | 7.15315E−05 |
| 34 | 860 | 1.98198E−05 | 431 | 5.32578E−05 | 1478 | 7.34197E−05 |
| 35 | 366 | 2.1602E−05 | 444 | 5.61639E−05 | 1849 | 7.50236E−05 |
| 36 | 1623 | 2.33391E−05 | 400 | 6.40624E−05 | 860 | 7.81441E−05 |
| 37 | 2083 | 2.6705E−05 | 2220 | 6.57456E−05 | 863 | 8.02699E−05 |
| 38 | 1415 | 2.73984E−05 | 811 | 6.60346E−05 | 3104 | 8.2096E−05 |
| 39 | 698 | 3.75545E−05 | 567 | 6.91719E−05 | 483 | 0.000100219 |
| 40 | 1448 | 3.77616E−05 | 698 | 7.76513E−05 | 2261 | 0.000109799 |
| 41 | 1958 | 4.26744E−05 | 559 | 9.24875E−05 | 1255 | 0.00011762 |
| 42 | 524 | 5.13812E−05 | 2148 | 0.000110933 | 1385 | 0.000123675 |
| 43 | 567 | 5.66682E−05 | 942 | 0.000124983 | 567 | 0.000124514 |
| 44 | 3819 | 8.01202E−05 | 2955 | 0.000133301 | 3411 | 0.000147102 |
| 45 | 1072 | 8.34258E−05 | 3811 | 0.000134362 | 1279 | 0.000166943 |
| 46 | 2220 | 9.37252E−05 | 2416 | 0.000149876 | 585 | 0.000180726 |
| 47 | 577 | 9.74444E−05 | 1059 | 0.000153009 | 767 | 0.00018102 |
| 48 | 1189 | 0.000103182 | 2829 | 0.000169332 | 2833 | 0.000194658 |
| 49 | 1255 | 0.000110333 | 1105 | 0.000172946 | 4417 | 0.00020764 |
| 50 | 482 | 0.000123376 | 3107 | 0.00018271 | 3157 | 0.00022174 |
| 51 | 1188 | 0.000126573 | 422 | 0.000185411 | 3827 | 0.00023567 |
| 52 | 598 | 0.000137327 | 2923 | 0.000192041 | 2985 | 0.00024376 |
| 53 | 1233 | 0.000139216 | 1958 | 0.000195379 | 1446 | 0.000265777 |
| 54 | 1109 | 0.000142116 | 409 | 0.000210959 | 1512 | 0.000266314 |
| 55 | 688 | 0.000150354 | 4375 | 0.000215558 | 1902 | 0.000266734 |
| 56 | 2081 | 0.000165549 | 590 | 0.000216529 | 3126 | 0.000267213 |
| 57 | 505 | 0.000172597 | 1706 | 0.000222244 | 1091 | 0.000273236 |
| 58 | 811 | 0.000177767 | 860 | 0.000241636 | 2704 | 0.000280037 |
| 59 | 658 | 0.000181265 | 511 | 0.000245805 | 3819 | 0.000281217 |
| 60 | 1417 | 0.000190332 | 1109 | 0.00025963 | 3028 | 0.000287503 |
| 61 | 400 | 0.000191511 | 566 | 0.000270008 | 1584 | 0.000297455 |
| 62 | 631 | 0.000199996 | 1030 | 0.00027902 | 1108 | 0.000303458 |
| 63 | 1148 | 0.000201067 | 1584 | 0.000279193 | 688 | 0.000322186 |
| 64 | 3028 | 0.00020364 | 2297 | 0.000288486 | 3235 | 0.000342517 |
| 65 | 1128 | 0.000229528 | 1189 | 0.000300938 | 1073 | 0.000365048 |
| 66 | 1584 | 0.000300395 | 1448 | 0.000310082 | 768 | 0.000378246 |

TABLE 4-continued

OBSERVED LUNG CANCER SERA PEAKS SHOWING SIGNIFICANT DIFFERENCES FROM CONTROL SERA PEAKS

| | CANCER | | SQUAMOUS | | ADENO | |
|---|---|---|---|---|---|---|
| RANK top 100 | M/z | TTEST | M/z | TTEST | M/z | TTEST |
| 67 | 2955 | 0.000311086 | 3819 | 0.000313803 | 416 | 0.000394578 |
| 68 | 3448 | 0.00031434 | 482 | 0.00033235 | 3211 | 0.000399899 |
| 69 | 1211 | 0.000329588 | 366 | 0.000345154 | 453 | 0.000455447 |
| 70 | 4375 | 0.000373785 | 416 | 0.000349674 | 621 | 0.000510203 |
| 71 | 416 | 0.000374259 | 3510 | 0.000374062 | 2018 | 0.000548043 |
| 72 | 1232 | 0.00037719 | 2379 | 0.000385556 | 400 | 0.000549928 |
| 73 | 4190 | 0.000380893 | 2557 | 0.000402581 | 4200 | 0.000550148 |
| 74 | 597 | 0.000430194 | 3540 | 0.000417945 | 639 | 0.000578957 |
| 75 | 2149 | 0.000433333 | 546 | 0.000426927 | 590 | 0.000604704 |
| 76 | 1587 | 0.00043905 | 598 | 0.000447887 | 861 | 0.000647832 |
| 77 | 2380 | 0.000446476 | 1148 | 0.000459241 | 2470 | 0.000649744 |
| 78 | 1110 | 0.000461849 | 3234 | 0.000483742 | 4617 | 0.000651629 |
| 79 | 419 | 0.000468051 | 2971 | 0.00049454 | 2711 | 0.000682323 |
| 80 | 703 | 0.000505907 | 2380 | 0.000512621 | 2818 | 0.00071177 |
| 81 | 568 | 0.000510269 | 582 | 0.000532021 | 1146 | 0.00071974 |
| 82 | 1067 | 0.00051754 | 2083 | 0.000536675 | 1109 | 0.000728467 |
| 83 | 4417 | 0.000578023 | 2679 | 0.000565591 | 419 | 0.000787203 |
| 84 | 721 | 0.000578408 | 631 | 0.000583039 | 2271 | 0.000787831 |
| 85 | 836 | 0.000579543 | 3475 | 0.000586899 | 383 | 0.000800867 |
| 86 | 483 | 0.000590873 | 1091 | 0.000650605 | 1167 | 0.000836824 |
| 87 | 858 | 0.000630917 | 2381 | 0.000685367 | 3762 | 0.000855479 |
| 88 | 2152 | 0.000684954 | 4175 | 0.000701775 | 2380 | 0.000874218 |
| 89 | 1146 | 0.00071974 | 1146 | 0.00071974 | 518 | 0.000881257 |
| 90 | 463 | 0.000728487 | 3028 | 0.000734199 | 363 | 0.000958913 |
| 91 | 481 | 0.000821984 | 3876 | 0.000741914 | 2442 | 0.000973283 |
| 92 | 1959 | 0.000822234 | 1073 | 0.000784969 | 994 | 0.001000104 |
| 93 | 840 | 0.000848995 | 1128 | 0.000801681 | 879 | 0.001048827 |
| 94 | 559 | 0.000851067 | 355 | 0.000813664 | 2931 | 0.001127405 |
| 95 | 2261 | 0.000879196 | 1080 | 0.000837565 | 3858 | 0.001133298 |
| 96 | 1902 | 0.000904958 | 1188 | 0.000838688 | 3744 | 0.001139343 |
| 97 | 444 | 0.000922214 | 543 | 0.000903559 | 489 | 0.001161764 |
| 98 | 4802 | 0.000927821 | 887 | 0.000936682 | 3752 | 0.001239616 |
| 99 | 2080 | 0.000965366 | 2751 | 0.000952568 | 2473 | 0.001262234 |
| 100 | 2148 | 0.000980378 | 3013 | 0.00102423 | 1799 | 0.001262252 |

Example 3

There is evidence that exposure to petroleum hydrocarbon products (combustion, vapor, or liquid) poses health and toxicological risks, especially with regard to respiratory, neurological, dermal, and cardiovascular pathologies/diseases (Robledo et al., 2000; Gauderman et al., 2007; Pleil et al., 2000; Ritchie et al.; 2001a; Ritchie et al., 2001b; Kabbur et al., 2001; Larabee et al., 2005; Lund et al., 2007; Peters et al., 2004). An association was found between exposure to vehicular traffic on public highways and the onset of a human myocardial infarction (MI) within a short period (one hour) after the exposure, suggesting a causal relationship between MI and vehicular exhaust (Peters et al., 2004). A correlation was found between nearby residence exposure to road traffic and lung development in children in the 10 to 18 year old age group (Gauderman et al., 2007). This study concluded that exposure to traffic on a freeway has negative effects on children's lung development, independent of regional air quality, that could affect lung function later in life. Exposures to petroleum (gasoline) exhaust emissions, both particulate and gaseous, were found to initiate vascular remodeling and oxidative stress pathways in mice, which are known to contribute to the progression of atherosclerosis (Lund et al., 2007). Biomarkers for atherosclerosis were found elevated in gasoline exhaust-exposed mice, including matrix metalloproteinases and heme oxygenase-1. Elevated reactive oxygen species were also found in the arteries of exposed animals (Lund et al., 2007).

The petroleum fuel, JP-8 (jet propulsion formulation-8), was previously shown to be toxic to rodents and humans in the liquid, vapor, and combustion exhaust states (Robledo et al., 2000; Ritchie et al., 2001a; Kabbur et al., 2001; Kinkead et al., 1992; Ulrich, 1999; Kobayashi and Kikukawa, 2000). The dermal exposure to JP-8 in rats and humans results in inflammatory responses at the site of application (Kabbur et al., 2001; Kinkead et al., 1992; Ulrich, 1999; Gallucci et al., 2004). Of related interest, a skin inflammatory condition in humans (psoriasis) was recently shown to increase the risk for myocardial infarctions (Gelfand et al., 2006). One study demonstrated that dermal exposure to JP-8 in rats for seven days induced organ stress and toxicity, including histo-pathological changes in heart tissue (Larabee et al., 2005). Inflammatory processes in the heart were induced in this JP-8 dermal model as evidenced by the presence of elevated numbers of infiltrating lymphocytes and generalized edema (Larabee et al., 2005). Heme oxygenase −1 (HO-1), a biomarker for atherosclerosis (Lund et al., 2007) was found elevated in the JP-8 dermal study (Larabee et al., 2005). Elevation of the inducible heat shock protein 70 (HSP70) in rat heart and other organs was also observed with no changes in constitutively expressed heat shock protein 70 (HSC70) (Larabee et al., 2005). This is consistent with generalized systemic stress being induced by a JP-8 dependent skin inflammatory condition, with a concomitant induction of a cellular defense mechanism. Cellular apoptosis was observed (Larabee et al., 2005) which is consistent with some cases of over-expression of HSP70 (Liu et al., 2003). JP-8 was previously found to induce apoptosis in tissue culture cells in vitro (Stoica et al., 2001).

In the present example, time-dependent serum profiling analysis is performed in a rodent JP-8 dermal exposure model to identify and assess any changes in biomarkers for this toxicant exposure. Serum profiling is the molecular analysis of changes in the levels of serum proteins and other molecules in response to changes in physiology (Richter et al., 1999). Such biomarkers could provide mechanistic information about JP-8 induced pathology, and also have the potential for risk analysis. Serum offers a convenient bodily fluid for biochemical analysis of disease processes since molecules in sera likely reflect changes in physiological states (Richter et al., 1999). The current example relies on mass spectrometry (MS) approaches which have proven valuable in sera proteomic analysis (Chambers et al., 2000). Certain acute-phase response proteins (Mackiewicz et al., 1993; e.g., haptoglobin, ceruloplasmin, and $\alpha_1$-inhibitor III), were observed to be altered in sera in a time-dependent manner in this JP-8 dermal exposure model. In addition, low-mass molecules, which correlated with either control (acetone) or JP-8 exposure, were identified by analyzing sera directly with ESI-MS.

Materials and Methods for Example 3

Rat dermal JP-8 exposure and sera collection. The rat dermal JP-8 exposure protocol was performed as described previously (Gallucci et al., 2004; Larabee et al., 2005). Filtered (0.45 μm) JP-8 (lot # UN1863) was a gift from the Air Force Research Laboratory (AFRL/HEPB) at Wright-Patterson Air Force Base and the Air Force Office for Scientific Research (AFOSR). Animals were handled according to standards described in the "Guide for the Care and Use of Laboratory Animals" prepared by the National Academy of Sciences and published by the National Institutes of Health (NIH publications 86-23 revised 1985). Rats were housed in polycarbonate cages containing hardwood chip bedding at room temperature on a 12 hr light/dark cycle. JP-8 was applied daily to the shaved neck (9 $cm^2$ patch) of the male Long-Evans rats (8-12 weeks old, 200-250 g) at a dose of 300 μl, and the control group was treated with 300 μl of acetone. Previously, acetone was shown not to cause histological skin or internal organ changes over this seven-day exposure treatment (Gallucci et al., 2004; Larabee et al., 2005). The rats remained in the fume hood for 1 hr post exposure. At 1, 3, 5, or 7 days following the exposure, rats were anesthetized with ketamine/zylazine and immediately sacrificed (decapitation), and whole blood was collected. Serum was obtained from whole blood by incubation at 4° C. for 45 min followed by centrifugation at 13,000 g for 2 min to remove the clot. Sera aliquots (50 μl) were frozen at −80° C. Sera protein concentrations were determined in triplicate using the Bradford protein assay (Bio-Rad).

Gel electrophoresis and tandem mass spectrometry (MS/MS) identification of sera proteins. 60 μg of sera protein were mixed with 0.5 volume sample buffer (62.5 mM Tris-HCl, pH 6.8, 2% SDS, 10% glycerol, 5% β-mercaptoethanol, and 0.001% bromophenol blue). Samples were heated at 95° C. for 10 min, and proteins were resolved by size using one-dimensional (1-D) 8-12% SDS-polyacrylamide gel electrophoresis (PAGE) as described (Larabee et al., 2005). Rat sera from a minimum of 3 JP-8 exposed and 3 acetone-exposed controls were analyzed on the same gel. Protein band quantification was performed by densitometry of the Coomassie-stained gel bands; scanned images were analyzed using the software package UN-SCAN-IT Version 5.1 (Silk Scientific Inc., Orem, Utah). Standard error of the mean (SEM) and Student's t test for time points were performed using Excel software.

Coomassie bands from 1-D gels were excised and destained with 40% MeOH-7.5% acetic acid, dehydrated in 100% MeOH, and then rehydrated in 70% MeOH. Gel bands were further destained in a 30% acetonitrile solution containing 100 mM ammonium bicarbonate, crushed, and then vacuum dried. Bands were rehydrated in 300-400 μl of 50 mM ammonium bicarbonate containing 1 μg trypsin (Promega). Digestion was performed overnight at 35° C. Peptide fragments were collected using a three-step acetonitrile/formic acid dehydration. Supernatants from gel piece centrifugations were collected and combined after each wash of 50, 75 and 95% acetonitrile in 5% formic acid. The supernatants were dried under vacuum and peptides resuspended in 200 μl of 2% formic acid containing 5% methanol. 50 μl of each sample was applied to a Vydac C18 100×0.3 mm HPLC column before MS/MS analysis. Peptides were eluted using a gradient of methanol containing 2% formic acid. MS/MS peptide sequencing was performed on a ThermoElectron LCQ electrospray-ion trap mass spectrometer. MS data were collected in the positive mode with an ESI source (capillary temperature 210° C., source voltage of 4.5 KV, source current of 80.00 pamps and capillary voltage of 26 volts). Data was acquired with 4 micro scans of 405 milliseconds utilizing the data-dependent MS/MS double-play method with a dynamic exclusion width of 0.50, reject mass width of 1.00, default isolation width of 2.00, normalized collision energy of 35.0%, and the inclusion of data-dependent MS/MS of singly charged ions. Identification of peptide/protein sequences was performed using TurboSequest (ThermoElectron), version 3.0. A peptide/protein database for screening was constructed from the non-redundant database acquired from NCBI as well as with a common contaminant database. Individual data search files (for each MS/MS peptide spectrum) were limited to mass values between 150 and 6000 Da, observable mass differences of 0.1 Da. Protein searches using peptide sequences identified the top X-correlation and were considered statistically significant when their Xcorr values were 2.5 or greater. The trypsin identification inherent in the digests was 1.5 and above. A previous study using this methodology listed highly significant values of Xcorr ranging from 1.9 to 3.9 (Dittmer et al., 2002).

Electrospray ionization-mass spectrometry (ESI-MS) of sera. For ESI-MS, a serum sample (frozen and thawed only once) was diluted 1 to 500 into a solution of 50% methanol and 2% formic acid and directly infused into the ESI source at a flow rate of 2 μl/min. High-resolution mass spectra were collected from two JP-8-exposed and two acetone-exposed control sera in random fashion in one day. The spectra were sampled at an m/z (mass divided by charge) resolution of two hundredths over an m/z range of 400 to 8000. Duplicate mass spectra for each serum sample were obtained by ESI time-of-flight (TOF) mass spectrometry (Applied Biosystems, Mariner System, Foster City, Calif.). Positive ion mode spectra were collected and averaged every 10 seconds and accumulated for 10 to 20 min for each injection. The instrument settings for ESI-MS were as follows: spray tip potential, 1612.50; nozzle potential, 61.04; skimmer 1 potential, 12.01; quad DC potential, 6.23; deflection voltage, 0.68; einzel lens potential, −30.00; quad RF voltage, 875.24; nozzle temperature, 195.01° C.; push pulse potential, 740.11; pull pulse potential, 359.82; pull bias potential, 6.00; accelerator potential, 3819.96; reflector potential, 1449.97; deflector potential, 2499.90.

Statistical analysis of ESI-MS data. Rat sera mass spectra were analyzed by a series of preprocessing steps to convert the high resolution, low mass data into a group of data points that can more easily be compared between treatment groups.

Because slight variances in the mass-to-charge (m/z) values of each peak may vary between sera samples, a linear two-point interpolation was used to provide sampling uniformity at a resolution of one hundredth of a Dalton. Since the intensity values for each sample may also vary from sample to sample as well as with MS instrument detector sensitivity, the intensity values were normalized by summing all intensity values within the m/z range of 800 to 1500 and dividing each peak by this value. The resulting data set was further compressed by summing all intensity values within one Dalton/charge interval. An exemplar (cohort) of the sera pattern was created by summing all available patterns for both the JP-8 and acetone-exposed classes. From this exemplar, peaks and valleys were identified. Each peak was identified by a number sequentially assigned and was defined by the beginning valley location, the peak location, and the ending valley location, which was the beginning valley location for the next peak. The same set of valley locations were then applied to all samples. The maximum intensity within the interval between valleys was considered to be the relative intensity for that peak.

Each serum spectrum was represented by a set of relative intensity and m/z values associated with the peaks. To determine which peaks are most significant for distinguishing JP-8 or acetone-exposed classes, a bootstrapping technique (Zharkikh and Wen-Hsiung, 1992) was used to randomly divide in blinded fashion all the peak data into many subsets. Each subset contains roughly 80% of the peaks from the JP-8 class and roughly 80% from the acetone class. For each subset, the Pearson's correlation coefficient was computed from the relative intensities and m/z values of each individual peak from both classes. This correlation routine was supplied by the software package Matlab (MathWorks, Inc., Natick, Mass.). Based on the resultant correlation coefficients, the peaks were rank ordered. A total of 1000 subsets were created, processed, and sorted in this fashion. The sorted list identified the peaks that were most correlated with the discrimination between the JP-8 class and the acetone control class. To provide discrimination ability in the subsets, a linear regression (James et al., 1985) was performed using the relative intensities and m/z values of the sorted peaks from the training set by associating the JP-8 samples with +1 and the acetone class with −1. Using the regression coefficients, a prediction was made for each sample in the training set. To set the threshold for discrimination between the two classes, a Bayesian classifier (Samso et al., 2002) was used which balances the probability of error between the false positives and false negatives. To test the efficacy of the discrimination power of the regression coefficients, random, unknown sets of sera spectra were processed in similar manners. The spectra were interpolated and compressed and the same set of valley locations were used to determine the maximum intensity for the associated peaks. These peaks were then sorted in the same rank order found earlier. Finally the sorted relative intensity values of the sorted peaks were subjected to the same linear regression model and discriminated by the same threshold found through the training set.

Results for Example 3

Figure 10:
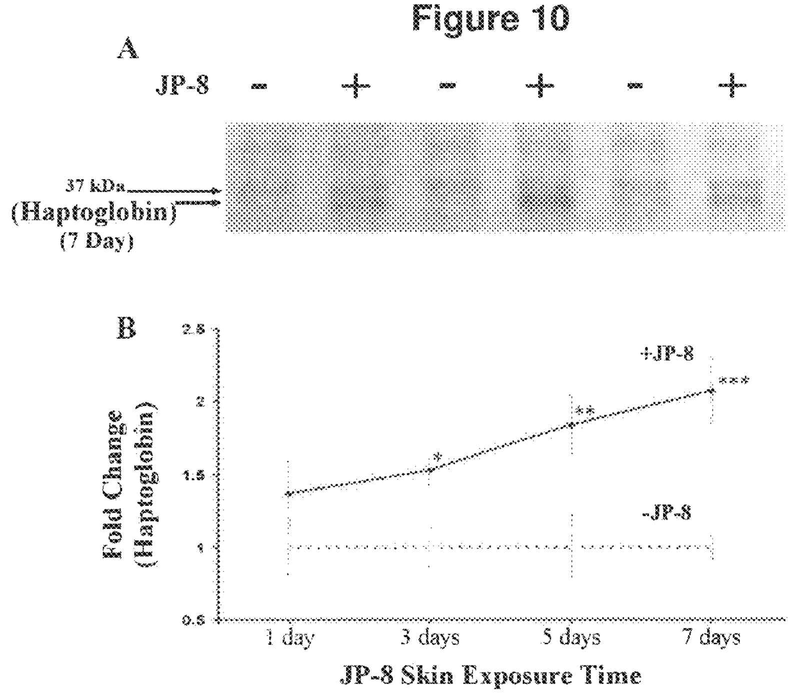
FIG. 10 illustrates the change over time in levels of the acute-phase protein haptoglobin in sera samples from rats dermal-exposed to JP-8 fuel or acetone. JP-8 rat exposures, SDS PAGE, and protein band identification and quantification for this figure as well as FIGS. 12-14 were described in the Materials and Methods. Panel A, Coomassie-stained SDS gel of a protein band determined to be haptoglobin (see FIG. 11 legend) in three independent sera samples after seven days of exposure to JP-8 fuel. (−) lanes indicate acetone exposure and (+) lanes indicate JP-8 exposure. Panel B, densitometric quantification of the haptoglobin Coomassie band over a time-course of JP-8 dermal exposure (solid line) or acetone dermal exposure (broken line). *, , * denote solid-line p values of 0.013 (n=5), 0.03 (n=4), and 0.01 (n=3) respectively, determined using the Student's t test.

JP-8 dermal exposure in rats causes an increase in sera levels of haptoglobin and ceruloplasmin acute-phase response proteins. Acute-phase response proteins are a major class of proteins present in serum whose levels increase (positive acute-phase proteins) or decrease (negative acute-phase proteins) in response to infection, stress, and/or inflammatory conditions (Mackiewicz et al., 1993). Utilizing gel electrophoresis and mass spectrometry, a number of acute-phase proteins whose serum levels change in a time-dependent manner in response to JP-8 dermal exposure have been identified in a rat model. Exhibited in FIG. 10 are the sera levels (derived from mass spectrometry and densitometry) of the acute phase protein haptoglobin in response to a time course of JP-8 dermal exposures in the rat model (Panel B). Panel A is Coomassie-stained SDS PAGE gel of the 7 day sera analysis. The haptoglobin protein band, which migrates on this gel with a molecular mass slightly less than 37 kDa, was identified by tandem MS/MS as described in FIG. 11. After 1 day of JP-8 skin exposure (+lanes, Panel A), haptoglobin levels (solid line, Panel B) are about 50% above acetone control levels (broken line) of this protein and increase to about 100% greater than control after 7 days of exposure (p=0.01). It is noted that dermis irritation is observed from 3-5 days of JP-8 exposure. Thus serum haptoglobin levels are responding rapidly to the fuel application to the skin. FIG. 11 exhibits the mass spectrometry identification of the haptoglobin band in FIG. 10. The identified peptide coverage is 38% and is observed in Panel A (bolded amino acid letters). The peptide whose sequence is identified in the MS/MS sequencing Panels B and C is underlined. Panel B exhibits the b and y-ion series (peptides fragmented from the amino or carboxyl termini, respectively) of this underlined peptide. Panel C is the actual tandem MS/MS spectra of this peptide. All other acute-phase proteins processed in this example were identified in a similar fashion.

The JP-8 dermal exposure time-course for the acute phase protein ceruloplasmin is exhibited in FIG. 12. As seen in Panel B, levels of ceruloplasmin remain essentially at control levels for days 1 and 3 after JP-8 exposure (solid line). The levels then rise in the 5 day exposure period to about 50% of control values (broken line) and continue to rise to about 200% at the 7 day period (p=0.018). This kinetic behavior is somewhat different from what is observed with haptoglobin levels which rise at the 1 and 3 day time periods (FIG. 10). The ceruloplasmin kinetics more reflect the JP-8 inflammation kinetics on the rat dermis. Observed in the Coomassie-stained gel panel in A are the ceruloplasmin bands from 3 control and 3 JP-8 rat-exposed 7 day sera. Both haptoglobin and ceruloplasmin are acute phase proteins that have a role in hemoglobin and iron metabolism (Edwards et al., 1986; Harris et al., 1995). Unlike the ceruloplasmin band, the 150 kDa protein band above it does not vary appreciably in response to JP-8 dermal exposure. This band was identified by tandem MS/MS as the acute-phase protein $\alpha_2$-macroglobulin.

Figure 13:
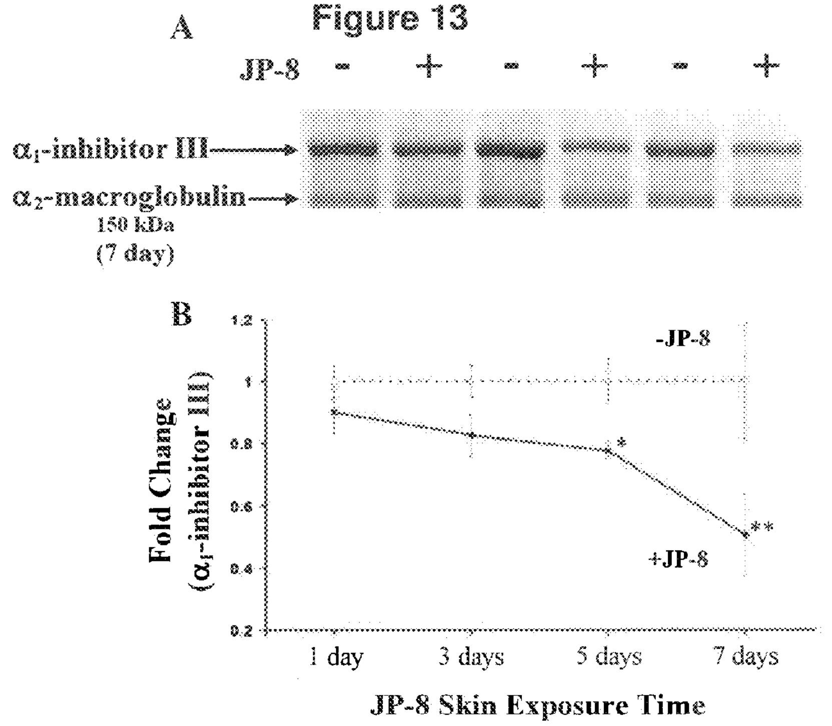
FIG. 13 illustrates that rat dermal exposure to JP-8 decreases levels of the negative acute-phase protein $\alpha_1$-inhibitor III in a time-dependent manner. Panel A, Coomassie-stained SDS gel of a protein band determined by MS/MS to be rat $\alpha_1$-inhibitor III (see FIG. 11 legend) in three independent sera samples after seven days of exposure to JP-8 fuel. The 150 kDa band was identified by MS/MS as rat $\alpha_2$ macroglobulin as was the 150 kDa band in FIG. 12A. (−) lanes indicate acetone exposure and (+) lanes indicate JP-8 exposure. Panel B, densitometric quantification of the $\alpha_1$-inhibitor III Coomassie band over a time-course of JP-8 dermal exposure (solid line) or acetone dermal exposure (broken line). *, ** denote solid-line p values of 0.04 (n=3) and 0.013 (n=3) respectively, determined using the Student's t test.
Figure 14:
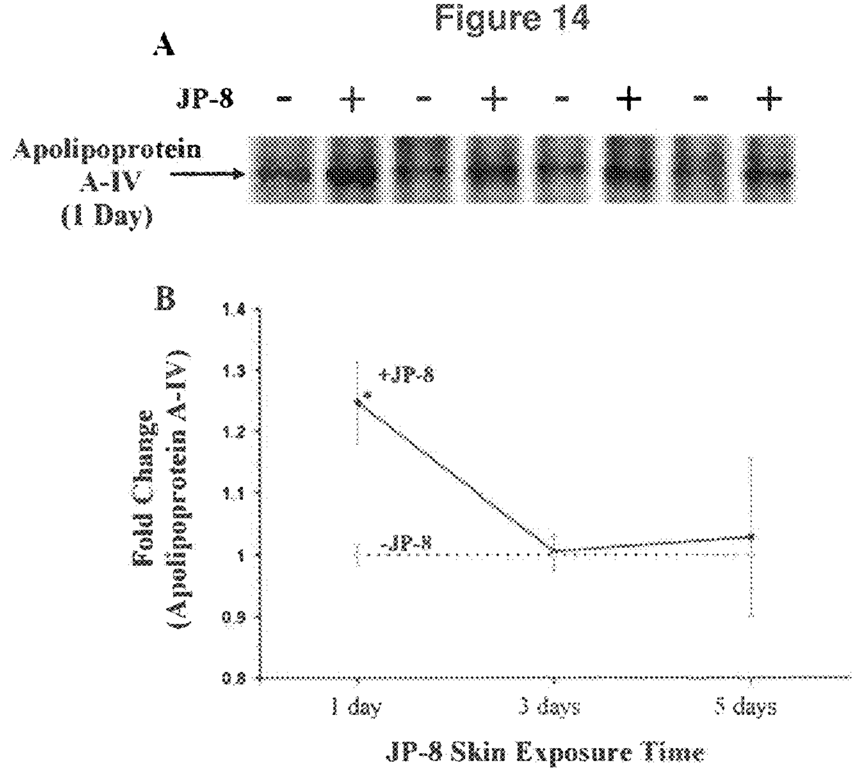
FIG. 14 illustrates the time-dependent increase then decrease of serum apolipoprotein A-IV in response to rat dermal exposure to JP-8. Panel A, Coomassie-stained SDS gel of a protein band determined by MS/MS to be rat apolipoprotein A-IV (see FIG. 11 legend) in three independent sera samples after one day of exposure to JP-8 fuel. (−) lanes indicate acetone exposure and (+) lanes indicate JP-8 exposure. Panel B, densitometric quantification of the apolipoprotein A-IV Coomassie band over a time-course of JP-8 dermal exposure (solid line) or acetone dermal exposure (broken line). * denotes a solid-line p value of 0.012 (n=4), determined using the Student's t test.

JP-8 dermal time-dependent exposure causes decreases in sera levels of $\alpha_1$-inhibitor III and a transient increase in apolipoprotein A-IV. $\alpha_1$-inhibitor III is a negative acute-phase protein as levels usually decrease in inflammatory responses (Mackiewicz et al., 1993). In the present example, a slight reduction was seen in this serum protein level (about 10%) at day 1 of JP-8 dermal exposure and continued decrease (to about 50%) through day 7 of exposure (FIG. 13, panel B, solid line; p=0.013). The reduction in levels of this protein is accelerated between day 5 and 7 of JP-8 exposure, the time period where the rat dermis inflammation response is most evident. Panel A in FIG. 13 exhibits an SDS PAGE gel of sera samples from 3-control and 3-day 7 JP-8 dermal-exposed rats. The decrease in the $\alpha_1$-inhibitor III band is observed (+lanes), and again little change is observed in the 150 kDa $\alpha_2$-macroglobulin band, a phenomenon also observed in FIG. 12. Apoliporotein A-IV is an acute-phase protein that has roles in cholesterol metabolism as well as anti-oxidant activities (Spaulding et al., 2006). As exhibited in FIG. 14, Panel B, initial levels of this protein in rat sera are elevated in response to 1 day dermal exposure to JP-8, increasing about 25% (solid line, p=0.012). However, after 3 and days of exposure, levels of apolipoprotein A-IV are reduced to control levels (broken line). The SDS gel of control (−) and 1 day JP-8 exposed (+) sera is displayed in Panel A.

Figure 15:
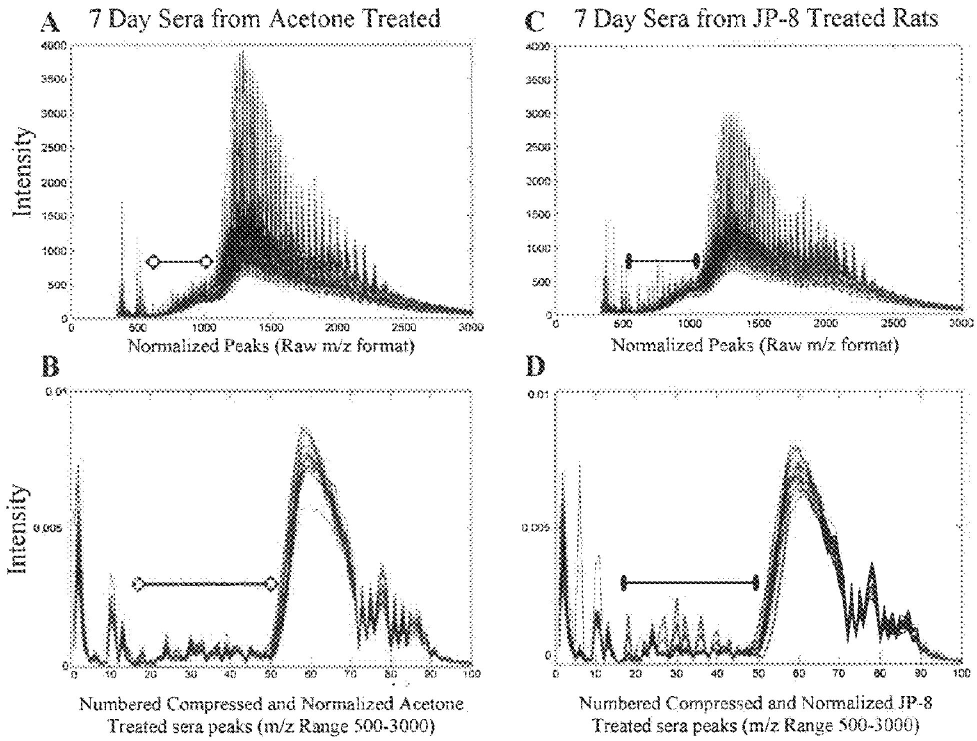
FIG. 15 illustrates high-resolution electrospray-ionization mass spectrometry (ESI-MS) spectra of sera from rat dermal control (acetone) or JP-8 exposure. High resolution ESI-MS on rat sera samples was performed as described in the Materials and methods. Panels A and B are superimposed raw m/z spectra from 8 rats exposed to dermal acetone and 8 rats exposed dermal JP-8, respectively; triplicate mass spectra were obtained from each rat serum sample giving a spectra sample size of 24 in each panel. Panels C and D are superimposed m/z spectra from panels A and B respectively in which the m/z peaks were normalized and compressed as described in the Materials and Methods; peaks are numbered along the x-axis. The open and dark-diamond bars (panels A-D) demark a spectral area of difference between the acetone and JP-8 sera, respectively.

Direct ESI-MS analysis of sera from control and JP-8 dermal exposed rats. FIG. 15 displays an electrospray ionization (ESI) MS experiment to distinguish serum mass profiles from 8 rats with dermal exposure to acetone (controls) and 8 rats from JP-8 exposed rats (mass spectra performed in triplicate). For these studies, serum (upon 500-fold dilution) was applied to an ESI-time of flight-MS instrument to produce the duplicate mass spectrum profile for each serum sample. It is noted in Panel B that many spectral peaks (denoted by the bar) exist in the 500-1200 m/z range of the JP-8 exposed sera (solid diamonds) when compared to the same region in the control spectra (open diamonds, Panel A). Next, the normalized control and JP-8 peaks were compressed (intensity peaks were assigned to the closest integer m/z value, panels C and D), which reduced the total number of peaks from about 4,000 to about 400. This was performed to make the subsequent correlation coefficient calculations more manageable.

For quantitative analysis, an individual Pearson's correlation coefficient was determined (described in the Materials and Methods section), based on the normalized relative intensity and mass/charge (m/z) values for each of the peaks. The resultant correlation coefficients can be sorted to determine which peak of a certain intensity is more significantly correlated with either control or JP-8 exposed rats. Table 5 lists the top 9 peaks which significantly correlated with JP-8 or normal sera. The correlation coefficients can be viewed as approximate percentages. That is, the correlation of 0.771 means approximately 77% of the JP-8 sera spectra had a peak of that mass to charge ratio (m/z, 702) with a given intensity. It is noted that the correlation coefficients for JP-8 peaks are larger than for the normal sera peaks. This indicates that the JP-8 sera are more homogeneous with respect to the low mass profiles than the normal sera, possibly due to the rat population reacting in similar fashion to the JP-8 insult. The m/z peaks in Table 5 were used to correctly discriminate 4 unknown sera samples (12 total mass spectra, data not shown).

Figure 16:
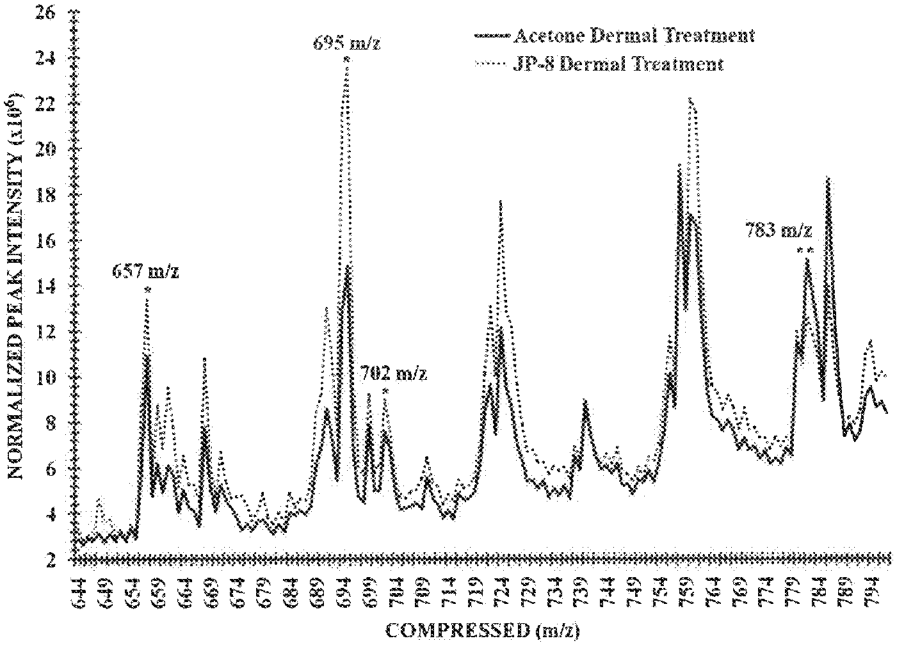
FIG. 16 illustrates JP-8 and acetone-treatment m/z peaks from Table 5 identified in ESI-MS spectra of rat sera. ESI-MS of rat sera, peak intensity normalization, and m/z compression were performed as described in the Materials and Methods. The mass spectra for JP-8 (dotted line) or acetone treatment (solid line) are an average of spectra from 5 sera samples, each analyzed in triplicate. Four m/z peaks identified in Table 5 for JP-8 (657, 695, 702 m/z) and acetone-treatment (783 m/z) are indicated with (*) and (**), respectively.

Table 5 has four m/z peaks in the 650-790 m/z range that correlate with JP-8 or acetone treatment (657, 695, 702 m/z for JP-8 and 783 m/z for acetone). It would be of interest to see if these peaks derived from statistical analysis of the MS data could be observed in sera mass spectra. FIG. 16 exhibits ESI mass spectra of normalized, compressed, and averaged sera spectra from rats with acetone dermal treatment (solid line) or JP-8 dermal treatment (dotted line). In this figure the JP-8 peaks from Table 5 (657, 695, 702 m/z) are more prominent in the sera from JP-8 treated-animals and the 783 m/z peak is more prominent in the sera from acetone-treated animals. This observation provides congruity between the statistical analysis used to identify low-mass peaks of correlative value for JP-8 or acetone treatment (Table 5) and the m/z peaks present in ESI-MS mass spectra of sera from JP-8 or acetone-treated animals.

TABLE 5

Identification of Biomarker Mass Peaks in the Sera of Rats Dermal-Treated with JP-8 Fuel

| ACETONE treatment | | | JP-8 FUEL treatment | | |
|---|---|---|---|---|---|
| Rank | m/z | corr | Rank | m/z | Corr |
| 1 | 856 | 0.628 | 1 | 702* | 0.771 |
| 2 | 907 | 0.592 | 2 | 1922 | 0.721 |
| 3 | 978 | 0.566 | 3 | 1971 | 0.712 |
| 4 | 830 | 0.554 | 4 | 695* | 0.676 |
| 5 | 972 | 0.541 | 5 | 1746 | 0.585 |
| 6 | 913 | 0.512 | 6 | 2024 | 0.569 |
| 7 | 783** | 0.467 | 7 | 474 | 0.515 |
| 8 | 1374 | 0.456 | 8 | 1670 | 0.512 |
| 9 | 520 | 0.44 | 9 | 657* | 0.451 |

m/z: mass of a molecule divided by the unit charge of the molecule
corr: Pearson's correlation coefficient
*, **peaks identified in ESI-mass spectra in FIG. 16

Discussion for Example 3

A previous study of JP-8 fuel toxicity indicated that the application of this petroleum product to rat dermis daily for a seven day period resulted in systemic stress as evidenced by increased levels of inducible heat shock protein 70 (HSP70) in rat internal organs (Larabee et al., 2005). Organ damage was also noted histologically, most notably in the heart where infiltration of inflammatory cells as well as fat accumulation (steatosis) was observed (Larabee et al., 2005). The present example utilized serum profiling and mass spectrometry approaches to identify serum biomarkers in order to further understand the nature of this rodent systemic response to dermal JP-8 exposure. A number of acute-phase proteins (APP), also termed inflammation-sensitive proteins (ISP) (Mackiewicz et al., 1993; Lind et al., 2004), were observed to be altered in the sera of rats exposed to dermal JP-8 applications. These proteins included haptoglobin, ceruloplasmin, $\alpha_1$-inhibitor III, and apolipoprotein A-IV. These alterations were consistent with previous non-JP-8 acute-phase responses in which levels of haptoglobin and/or ceruloplasmin are elevated, and levels of $\alpha_1$-inhibitor III, a proteinase inhibitor and negative acute phase protein, were reduced (Mackiewicz et al., 1993; Aiello et al., 1988). The acute-phase response in mammals is a biochemical redirection in homeostasis to deal with an acute inflammatory or otherwise stressful insult (Mackiewicz et al., 1993). The acute-phase response is not only accompanied by changes in APP levels but also changes at different rates and to different degrees (Mackiewicz et al., 1993). Because all these phenomena were observed, it was concluded that dermal application of JP-8 in rats elicits an acute-phase response, possibly triggered by chemical and inflammatory reactions at the site of application and possibly elsewhere.

As with other acute-phase responses, kinetic differences were observed in the appearance/disappearance of several acute-phase proteins in response to JP-8 dermal application. Each acute-phase response is likely to have unique attributes depending upon the triggering factors. Although haptoglobin levels rise after 1 day of exposure, ceruloplasmin levels rise after 5 days of exposure (FIGS. 10 and 12). Both these proteins have roles in hemoglobin and iron metabolism. Haptoglobin binds hemoglobin and iron released from red blood cells; ceruloplasmin is an iron oxidase that produces ferric ions from ferrous ions, with ferric ions being required for binding to transferrin. It is possible that the dermal application of JP-8 causes oxidative stress leading to red blood cell lysis and induction of haptoglobin synthesis. This oxidative stress was observed in JP-8 treated tissue culture cells (Boulares et al., 2002) and could involve oxidation of hydrophobic alkane and aromatic hydrocarbons found in JP-8 (Ritchie et al., 2001a). Exposure to aromatic hydrocarbons (e.g. benzene which is present in JP-8 in low amounts) caused reductions in blood cell counts in humans (Lan et al., 2004). Increased levels of ceruloplasmin and its ability to oxidize ferrous to ferric iron may not be required until later in the acute response. Ceruloplasmin may also have a role in cardiovascular disease (Giurgea et al., 2005). The elevation of this protein observed in this example could have a mechanistic link to the cardiac damage observed in the earlier JP-8 dermal study (Larabee et al., 2005).

$\alpha_1$-inhibitor III is the classic negative acute-phase protein (Mackiewicz et al., 1993), and its levels decrease in a time-dependent manner in the rat dermal JP-8 exposure model (FIG. 13). This protein is a member of the anti-proteinase family of serum proteins. Levels of a structurally related acute-phase protein, $\alpha_2$-macroglobulin, were not appreciably altered by rat dermal exposure to JP-8 (FIGS. 12 and 13). Systemic inflammatory conditions like adjuvant-induced arthritis in rats induce high levels of $\alpha_2$-macroglobulin within two days (Doherty et al., 1998). These proteinase inhibitor proteins are produced in liver hepatocytes (Lonberg-Holm et al., 1987). In the previous 7 day JP-8 dermal study, no evidence of inflammation was observed in the liver but was observed in the heart (Larabee et al., 2005). It is possible that although JP-8 is inducing an inflammatory condition in the rat dermis, any systemic inflammatory response generated is not extensive enough and/or of the proper nature to increase levels of $\alpha_2$-macroglobulin. Apolipoprotein A-IV is another negative acute-phase protein whose levels are down-regulated in rheumatoid arthritis (Doherty et al., 1998). Although an initial rise in levels of this protein was seen at day 1 of JP-8 exposure, levels are reduced to control levels at days 3 and 5; no overall decrease like that observed in an inflammatory arthritic condition. This is additional evidence that the JP-8 induced acute-phase response does not mimic the systemic inflammatory response induced by arthritis. The transient induction of apolipoprotein A-IV at 1 day of JP-8 exposure could be a response to oxidative stress initially induced by JP-8 dermal treatment as this protein has anti-oxidant activities (Spaulding et al., 2006).

The studies in FIGS. 10-14 involved mass spectrometric analysis of sera proteins resolved by SDS PAGE. Performing mass spectrometry (MS) directly on sera and other readily available bodily fluids is a useful technique to catalog physiological states and identify biomarker peaks and their patterns (Richter et al., 1999). The hypothesis behind such studies is that changes in physiological states (including those involving disease) result in alterations in the kinds and amounts of biomolecules secreted and/or shed from organs and tissues into the bloodstream. Such a paradigm should prove useful in toxicological analyses with the added benefit that sera analysis involves minimal animal disruption. Using electrospray ionization (ESI)-MS analysis directly on sera from JP-8 dermal exposed rats, a region in the low-mass spectra of JP-8 exposed animals was identified that had peak differences from the same region in control animals (FIG. 15). In addition, a number of sera low-mass peaks were identified that were correlated to either control exposures (acetone) or JP-8 exposures (Table 5, FIG. 16).

Thus, this Example demonstrates that the presently disclosed and claimed invention may be utilized for health-risk analysis to toxicological exposures as well. Although petroleum fuel products have major negative impacts on the environment, this and previous studies indicate they are health hazards as well.

Example 4

The identification of biomarkers for disease states is important for understanding underlying mechanisms, and in disease diagnosis and treatment. Military personnel are increasingly being exposed to body blast concussions and associated traumatic brain injuries (TBI). It is important to identify brain and body-related injuries resulting from such exposures. In the present Example, it is demonstrated that sub-traumatic brain injuries result in measurable changes in serum and tissue biomarkers that can be analyzed by proteomic approaches (mass spectrometry). The identification of these biomarkers and their patterns, and the following of their time-courses subsequent to the blast as well as with any therapeutic modality, will lead to better diagnosis and treatment of these blast-related injuries.

Materials and Methods for Example 4

Electrospray ionization-time of flight mass spectrometry (ESI-TOF MS) of sera from blast and control rats. High-resolution mass spectra were generated from sera samples of three blast and three control sera in random fashion per day. The spectra were sampled at an m/z (mass divided by charge) resolution of two hundredths over an m/z range of 400 to 8000. Triplicate mass spectra for each serum sample were obtained by ESI-TOF-MS (Applied Biosystems, Mariner System, Foster City, Calif.). For ESI-MS, positive ion mode spectra were collected and averaged every 10 seconds and accumulated for 10 to 20 min for each injection. MS/MS peak structural information was performed on a ThermoElectron LCQ electrospray-ion trap mass spectrometer. MS data was collected in the positive mode, and peptide sequence identification was performed using TurboSequest (ThermoElectron), version 3.0.

Statistical analysis of sera mass spectra. Because slight variances in the m/z values of each peak were observed between samples, a linear two-point interpolation was used to provide sampling uniformity between samples (Hanas et al., 2008; Larabee et al., 2008). Since the intensity values for each sample may vary in magnitude from sample to sample, the values must be normalized by summing all intensity values within the m/z range of 1000 to 2000 for each sample. All intensity values were divided by this normalization constant to yield the relative intensity pattern for that sample. The data set was further compressed by summing all intensity values within a particular interval (1 Dalton). An exemplar (cohort) of the sera pattern was created by summing all available patterns for both the normal class and the different blast classes. Each sample was represented by a set of relative intensity values associated with the peaks. To determine which peak is significant, a bootstrapping technique was used to randomly divide the training set into many subsets (Hanas et al., 2008). For each subset, the Pearson's correlation coefficient was computed from the relative intensities of each individual peak from both classes. To provide discrimination ability on the unknowns, a linear regression was performed using the relative intensities of the sorted peaks from the training set by associating the cancer samples with the normal class. Using the regression coefficients, a prediction was made for each sample in the training set. The m/z peaks that correlate with either normal or different blast classes were then identified in the actual mass spectra (Hanas et al., 2008; Larabee et al., 2008).

Results for Example 4

Figure 17:
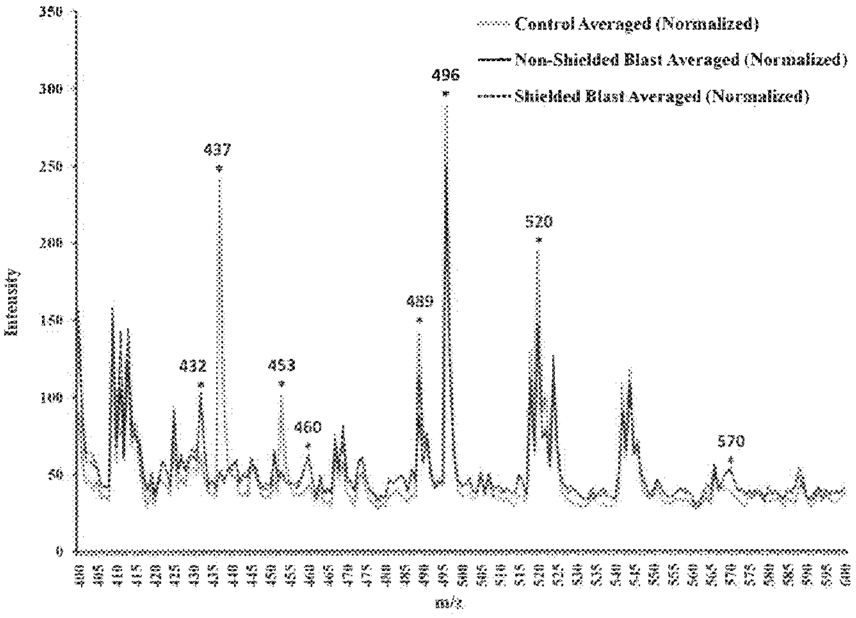
FIG. 17 illustrates low mass spectra (400-600 m/z) of sera from control or 1 hour post blast-exposed rats.

Sera differences in rat control sera versus 1 hr post-blast sera over the 400 to 600 m/z range. FIG. 17 below illustrates ESI-MS experiments to distinguish sera mass spectrometry profiles from 3 normal rats, 3 rats exposed to a shielded blast (1 hr), and 3 rats exposed to a non-shielded blasts (1 hr, all three classes of mass spectra were normalized and averaged). Serum (upon 400-fold dilution) was applied to an ESI-time of flight-MS instrument to produce the mass spectrum profile for each serum sample (see Materials and Methods section).

The rat control sera over this narrow range of m/z (charge divided by mass) have the largest intensity changes (m/z peaks 437, 453, 489, 496, and 520), and the intensity change is in the positive direction relative to the blast sera. These sera were collected 1 hr after the experimental condition (blast or no blast) which indicates that these peak signals were reduced rather quickly in response to the blast condition. Importantly, the ability of the presently disclosed and claimed invention to identify changes so soon after the blast insult portends well for subsequent time-course analyses. Of note, not much of a difference was observed at this early time point in the shielded versus non-shielded blast effect. This observation is consistent with a general suppressive effect in the sera from blast-exposed rats. The largest changes in this mass range are for peaks 453 and 437. The tandem mass spectrometry capabilities (MS/MS) allow these and other peaks to be structurally identified. It is noted that small intensity increases are seen for the 432, 460, and 570 m/z values in the blast samples versus the control samples. Thus, changes in physiological state (including those involving trauma) result in alterations in the kinds and amounts of biomolecules secreted and/or shed from organs and tissues into the bloodstream.

Figure 18:
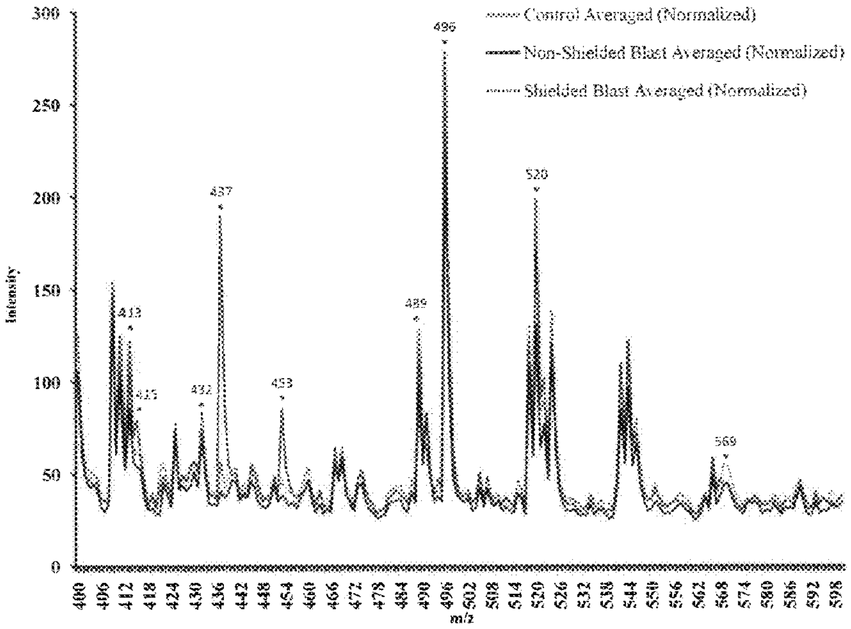
FIG. 18 illustrates low mass spectra (400-600 m/z) of sera from control of 24 hours post blast-exposed rats.

Sera differences in rat control sera versus 24 hr post-blast sera. FIG. 18 illustrates ESI-MS experiments to distinguish sera mass spectrometry profiles (400-600 m/z) from 3 normal rats, 3 rats exposed to a shielded blast (24 hr), and 3 rats exposed to a non-shielded blasts (24 hr, all three classes of mass spectra were normalized and averaged). Serum (upon 400-fold dilution) was applied to an ESI-time of flight-MS instrument to produce the mass spectrum profile for each serum sample (see Materials and Methods section).

The rat control sera over this narrow range of m/z (charge divided by mass) have the largest intensity changes (higher intensity for the control) at m/z peaks 437 and 453 like the 1 hr data. The 489, 496, and 520 m/z peaks, which are elevated in the control sera relative to the post-1 hr blast sera, are now equalized in the 24 hr-post blast sera. These sera were collected 1 hr after the experimental condition (blast or no blast) which indicates that these peak signals were reduced rather quickly in response to the blast condition. Importantly, the ability of the presently disclosed and claimed invention to identify changes so soon after the blast insult portends well for subsequent time-course analyses. Of note, not much of a difference was observed at this early time point in the shielded versus non-shielded blast effect. This observation is consistent with a general suppressive effect in the sera from blast-exposed rats. The largest changes in this mass range are for peaks 453 and 437. The tandem mass spectrometry capabilities (MS/MS) allow these and other peaks to be structurally identified. It is noted that small intensity increases are seen for the 432, 460, and 570 m/z values in the blast samples versus the control samples.

Figure 19:
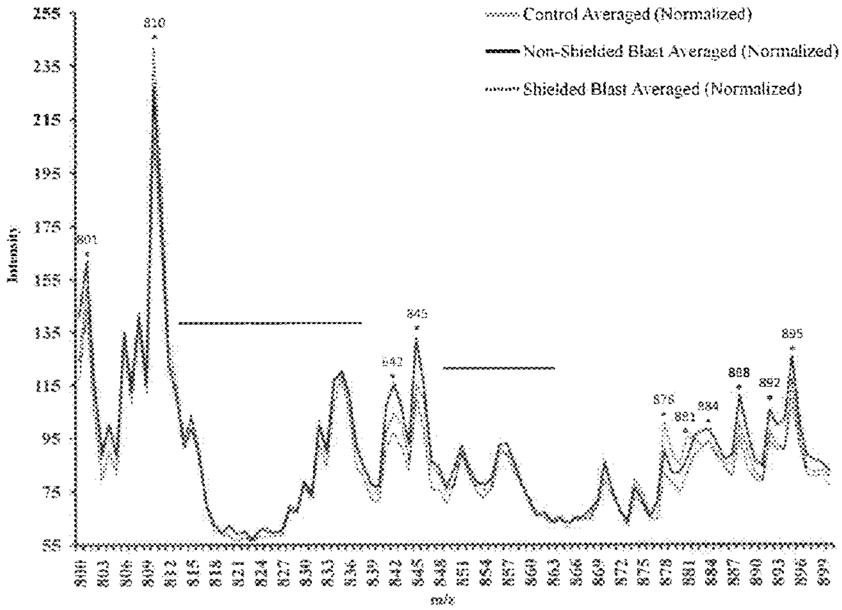
FIG. 19 illustrates low mass spectra (800-900 m/z) of sera from control or 24 hour blast-exposed rats.

FIG. 19 exhibits spectra in the 800-900 m/z range. A non-shielded change is observed at m/z peak 845. The horizontal lines indicate spectral areas of little change. Thus, changes in physiological state (including those involving trauma) result in alterations in the kinds and amounts of biomolecules secreted and/or shed from organs and tissues into the bloodstream.

Example 5

Strategic preparedness for trauma events, resulting from natural or man-made disasters, is important not only for regaining the health of the affected individuals but also for the well-being of the nation. Rapid medical diagnosis and subsequent analysis of individuals involved in trauma events is essential for positive outcomes. For this purpose, cutting edge diagnostic capabilities need to be continuously developed. Mass spectrometry profiling is an advancing biotechnology with the capability to screen biofluids and tissues for protein/biomolecule changes characteristic of a particular trauma injury. Mass spectrometry profiling of disease states is based on the premise that tissues and organs are constantly shedding/secreting proteins/biomolecules into the blood and other bodily fluid systems. These patterns of biomolecules will change depending on the disease state of the individual, thus giving every disease/trauma state a unique proteomic profile (Richter et al., 1999). This technology relies heavily on the development of high-resolution mass spectrometry (MS) to decipher these biomolecule patterns as well as to identify potential biomarkers of a particular trauma/disease state. This present example is directed to proteomic profiling analyses as they relate to diagnosing and treating traumatic brain injury (TBI) and bacterial sepsis/neuroinflammation.

Traumatic brain injury (TBI) and the need for diagnostic tests at the molecular level. Traumatic Brain Injury (TBI) results from a sudden insult to the brain, and can vary over a wide range of severities. In the United States, approximately 1.4 million people experience a traumatic brain injury, and approximately 50,000 Americans die every year from TBI (Thurman et al., 1999). Future disasters, both natural and man-made, can cause such brain injuries, the rapid management of which will improve outcomes. Moderate to severe cases of TBI are characterized by increased swelling of the brain tissue which is indicative of the presence of inflammatory events (Thurman et al., 1999). One hypothesis is that inflammatory responses to a varying degree are characteristic of all forms of TBI. Because inflammation can be described as a cascade of molecular events, it is important to perform molecular analyses in the diagnosis as well as treatment progression of all forms of TBI beyond the traditional MRI, PET, and CT scans. At present, no molecular analyses are routinely performed in the diagnosis and screening for TBI severity. Molecular analyses as those described in this example will result in greater understanding of TBI and aid in the development of new therapeutic strategies.

Molecular analysis of systemic sepsis and its relationship to neuroinflammation. Sepsis is a common and often fatal condition caused by systemic infection, and marked by sequential activation of inflammatory and then counter-inflammatory host responses (Hotchkiss et al., 2003). Sepsis is a likely major consequence of most disasters including natural and man-made situations. An emerging consensus is that the central nervous system (CNS) as well as bodily organs are damaged by systemic infections such as sepsis; the CNS does not have to be infected directly by the bacterial or viral pathogens to see these effects (Brandt et al., 2008; and Wang et al., 2004). Importantly, monocytes containing bacteria were observed migrating into the brain in a sepsis-dependent process (Drevets et al., 2004). Thus, studying CNS infections as a part of systemic disease studies brings added value to understanding how the immune system affects the brain in mass casualty situations. The data presented in Drevets et al. (2004) demonstrates that host responses to lethal bacterial infection in peripheral organs activate the brain and trigger it to produce chemokines, upregulate adhesion molecules, and recruit monocytes into it. Thus, there is a clear and relevant connection between host responses to systemic infection and critical events in the brain that result in neuroinflammation. In the present example, blood biomarkers for sepsis were elucidated by mass spectrometry-based serum profiling in order to help distinguish between fatal and non-fatal bacterial infections. In addition, CSF was analyzed from wild-type mice which recruit monocytes to the brain during sepsis and from mutant/IFNg −/− mice which do not recruit inflammatory monocytes to the brain during sepsis.

Materials and Methods for Example 5

Electrospray ionization-time of flight mass spectrometry (ESI-TOF MS) of TBI, sepsis, and control CSF and sera. In each set, CSF were collected from a minimum of 3 blast or bacteria-exposed rats and mice and 3 normal ketamine-anesthetized rats or mice by surgical exposure of the atlanto-occipital membrane followed by CSF extraction with a 26 g needle-syringe. Serum was obtained from the whole blood of TBI or sepsis rats and mice, and control rats and mice by incubation at 4° C. for 45 min followed by centrifugation at 13,000 g for 2 min to remove the clot. CSF and sera aliquots (50 μl) were frozen at −80° C., and aliquots were not reused after freezing and thawing. For ESI-MS, a serum sample was diluted 1 to 400 (1 to 150 for CSF) into a solution of 50% methanol and 2% formic acid and directly infused into the ESI source at a flow rate of 2 μl/min. High-resolution mass spectra were collected from disease and control sera in random fashion per day. The spectra were sampled at an m/z (mass divided by charge) resolution of two hundredths over an m/z range of 400 to 8000. Triplicate mass spectra for each serum sample were obtained by ESI time-of-flight (TOF) mass spectrometry (Applied Biosystems, Mariner System, Foster City, Calif.). Positive ion mode spectra were collected and averaged every 10 seconds and accumulated for 10 to 20 min for each injection.

Statistical analysis of the mass spectral data. Sera and CSF mass spectra were analyzed by a series of preprocessing steps to convert the high resolution, low mass data into a group of data points that can more easily be compared between treatment groups. Since the intensity values for each sample may also vary from sample to sample, the intensity values were normalized by summing all intensity values within the m/z range of 800 to 1500 and dividing each peak by this value. The resulting data set was further compressed by summing all intensity values within one Dalton/charge interval. An exemplar (cohort) of the sera pattern was next created by summing all available patterns for both the TBI/sepsis and the control classes. From this exemplar, peaks and valleys were identified. The maximum intensity within the interval between valleys was considered to be the relative intensity for that peak. Each sample spectrum was represented by a set of relative intensity and m/z values associated with the peaks. To determine which peaks are most significant for distinguishing classes, a bootstrapping technique (Zharkikh et al., 1992) was used to randomly divide in blinded fashion all the data into many subsets. For each subset, the Pearson's correlation coefficient was computed from the relative intensities and m/z values of each individual peak from both classes. This correlation routine was supplied by the software package Matlab (Mathworks, Inc., 2002). Based on the resultant correlation coefficients, the peaks were rank ordered. A total of 1000 subsets were created and processed. The final rank of each peak was the sum of all individual ranks. Based on this final rank, all peaks were reordered from highest to the lowest. The sorted list identified the peaks that are most correlated with the discrimination between the sepsis/TBI classes and the normal class. To provide discrimination ability in the subsets, a linear regression (James et al., 1985) was performed using the relative intensities and m/z values of the sorted peaks from the training set by associating the treatment samples with +1 and the normal class with −1. Using the regression coefficients, a prediction was made for each sample in the training set. To set the threshold for discrimination between the two classes, a Bayesian classifier (Samso et al., 2002) was used which balances the probability of error between the false positives and false negatives. To test the efficacy of the discrimination power of the regression coefficients, random, unknown sets of sera spectra were processed in similar manners. The spectra were interpolated and compressed, and the same set of valley locations were used to determine the maximum intensity for the associated peaks. These peaks were then sorted in the same rank order found earlier. Finally, the sorted relative intensity values of the sorted peaks were subjected to the same linear regression model and discriminated by the same threshold found through the training set (Example 1; and Larabee et al., 2008).

Results for Example 5

Mass spectrometry profiling of TBI in a rodent blast model. The identification of biomarkers for disease states is important for understanding underlying mechanisms, diagnosing disease, and aiding in treatment. Military personnel are increasingly being exposed to body blast concussions and associated traumatic brain injuries (TBI). It is important to identify the types of brain and other physiological injuries resulting from such exposures. In the present example, it is demonstrated that sub-traumatic as well as traumatic brain injuries will result in measurable changes in cerebral spinal fluid (CSF), serum, and brain tissue biomarkers that can be analyzed by proteomic approaches (mass spectrometry and gel electrophoresis). CSF and serum reflect animal physiology because tissues and organs including brain are actively shedding/secreting biomolecules into these fluids. Importantly, these secreted biomarkers will change with any physiological state changes (Richter et al, 1999; and Example 1). The identification of these biomarkers and their patterns, and following their time-courses subsequent to the blast, will lead to better diagnosis and treatment of these blast-related injuries.

Electrospray ionization (ESI) mass spectrometry (MS) profiling as a means to distinguish and identify biomarkers in CSF and sera from normal rats and from blast-exposed rats. MS profiling of sera and other bodily fluids like CSF has become a powerful technique to mechanistically analyze disease states and identify biomarker patterns, as described herein above with regard to Example 1. With the use of statistical analysis capable of pattern resolution and recognition of thousands of biomolecules found in the low mass region of sera for example (400-2000 m/z), it is possible to discriminate disease state patterns. Small molecules are analyzed directly in the CSF and sera using electrospray ionization mass spectrometry (ESI-MS). This ESI methodology can be automated and doesn't suffer from the potential problems of SELDI (surfaced enhanced laser desorption ionization) analysis induced by washing, chemical treatment, and crystallization of samples. In addition, ESI-MS can screen for other small biomolecules besides peptides. TBI might be expected to affect biomolecules/metabolites secreted into the CSF from the brain.

Figure 20:
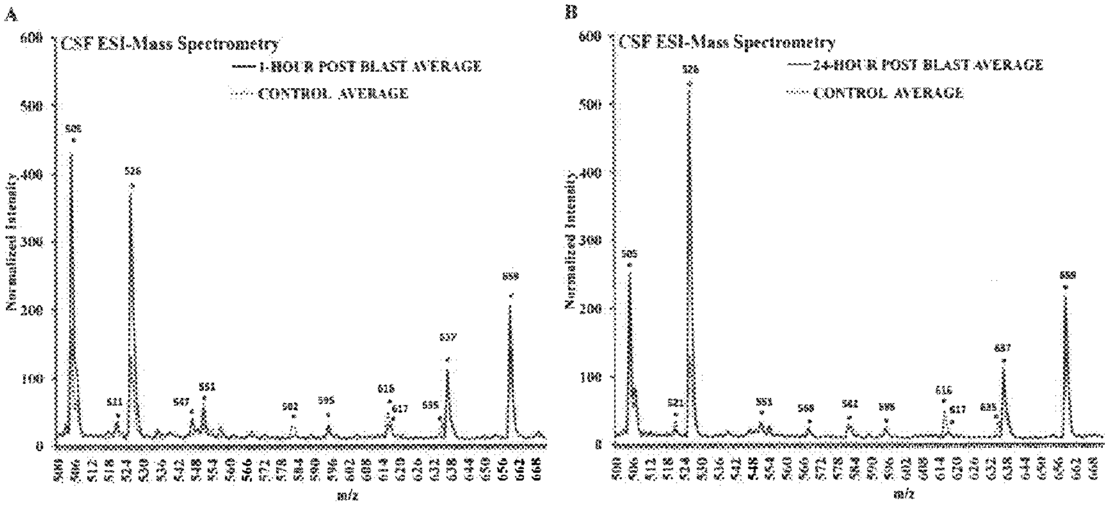
FIG. 20 illustrates low-mass profiling spectra of cerebrospinal fluid (CSF) from control, 1 hour, and 24 hour post blast-exposed rats.

FIG. 20 illustrates ESI-MS experiments to distinguish CSF profiles from 3 non-exposed rats and 3 rats exposed to a shielded blast (CSF collected 1 hr and 24 hr post blast). CSF (upon 150-fold dilution) was applied to an ESI-time of flight-MS instrument to produce the mass spectrum profile for each serum sample (see Materials and Methods section). In both classes, the mass spectra were normalized and averaged. The 1 hr post blast-exposed rat CSF over this narrow range of m/z (charge divided by mass, FIG. 20A) has the largest intensity (amount) differences (higher blast intensity versus the control) at m/z peaks 505 (about 33% higher) and 526 (about 300% higher). Of interest, the 526 peak increases about 30% in the 24 hr post-blast CSF (FIG. 20B) over the 1 hr timepoint, and the 505 peak increases about 50% over the 1 hr-time point. At 24 hr a small 547 peak present at 1 hr is greatly reduced. The fact that changes are seen between the 1 hr and 24 hr post-blast indicates that it is possible to assess CSF changes over time using this technology. Thus, changes in physiological states (including those involving trauma) can be assayed as alterations in the kinds and amounts of biomolecules secreted and/or shed from organs and tissues into bodily fluids like CSF. Such identifications should prove useful in the diagnosis and treatment of TBI.

Figure 21:
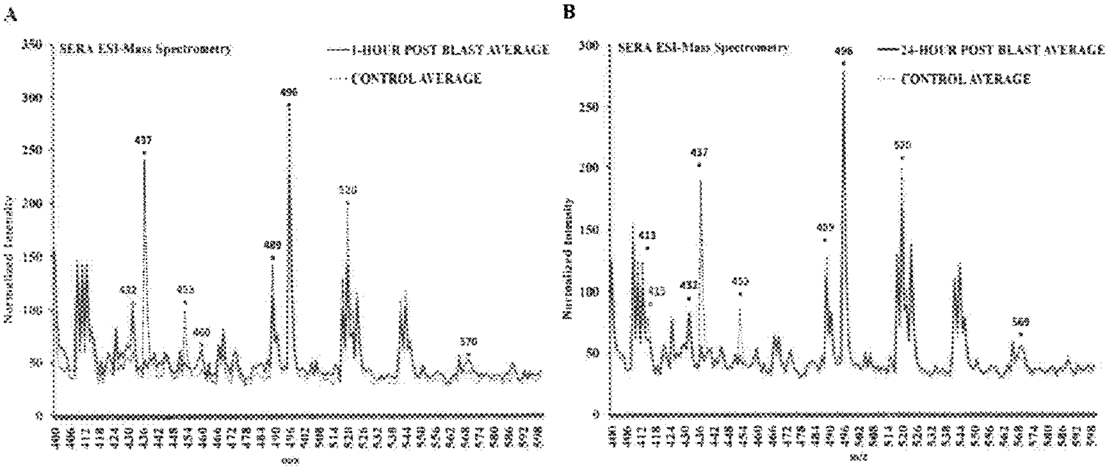
FIG. 21 illustrates low-mass profiling spectra of sera from control, 1 hour, and 24 hour post-blast exposed rats.

Mass profiling of sera biomarkers in control rats versus 1 and 24 hr post-blast rats as assayed by ESI-MS. FIG. 21 illustrates ESI-MS experiments to distinguish sera profiles from 3 control rats, and 3 rats exposed to a shielded blast (1 hr and 24 hr post-blast sera collection); all classes of mass spectra were normalized and averaged). Serum (upon 400-fold dilution) was applied to an ESI-time of flight-MS instrument to produce the mass spectrum profile for each serum sample (see Materials and Methods section). Importantly, the rat control sera over this narrow range of m/z (mass divided by charge) have the largest intensity (amount) changes (higher intensity for the controls) at m/z peaks 437 and 453 for both the 1 hr and 24 hr post-blast sera, (FIG. 21, panels A and B). The 496 m/z peak which is reduced at 1 hr (35%) returns to the control level at 24 hr. Importantly, the ability of the presently disclosed and claimed invention to identify changes so soon after the blast insult portends well for subsequent time-course analyses. These observations are consistent with a general early suppressive effect in the sera from blast-exposed rats, at least at the early time points. The tandem mass spectrometry capabilities (MS/MS) allow these and other annotated peaks to be structurally identified. The fact that changes are observed at the 1 hr and 24 hr post-blast sera demonstrates that it is possible to assess sera changes over time using this technology. These CSF and sera data demonstrate that changes in physiological state (including those involving trauma) result in alterations in the kinds and amounts of biomolecules secreted and/or shed from organs and tissues into the CSF and bloodstream.

Thus, in accordance with the present invention, there has been provided methods of identifying biomarkers in cancer sera that fully satisfy the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the invention.

References

The following references, to the extent that they provide exemplary procedural or other details supplementary to those set forth herein, are specifically incorporated herein by reference.

Aiello L P, Shia M A, Robinson G S, Pilch P F, Farmer S R. Characterization and hepatic expression of rat alpha 1-inhibitor III mRNA. J Biol Chem. 1988; 263:4013-22.

American Cancer Society. (2007) Cancer facts & figures 2007. Atlanta (GA): American Cancer Society, Inc. http://www.cancer.org/docroot/STT/content/STT 1× Cancer Facts FIGURES 2007.asp Banks R E, Stanley A J, Cairns D A, Barrett J H, Clarke P, Thompson D, Selby P J. (2005) Influences of blood sample processing on low-molecular-weight proteome identified by surface-enhanced laser desorption/ionization mass spectrometry. Clin. Chem. 51: 1637-1649.

Boulares A H, Contreras F J, Espinoza L A, Smulson M E. Roles of oxidative stress and glutathione depletion in JP-8 jet fuel-induced apoptosis in rat lung epithelial cells. Toxicol Appl Pharmacol. 2002; 180:92-9.

Brandt, C. T., D. Holm, M. Liptrot, C. Ostergaard, J. D. Lundgren, N. Frimodt-Moller, I. C. Skovsted, and 1. J. Rowland. 2008. Impact of bacteremia on the pathogenesis of experimental pneumococcal meningitis. J Infect Dis 197:235-244.

Chambers G, Lawrie L, Cash P, Murray G L. Proteomics: a new approach to the study of disease. J. Pathol. 2000; 192:280-288.

Chen R, Pan S, Yi E C, Donohoe S, Bronner M P, Potter J D, Goodlett D R, Aebersold R, Brentnall T A. (2006) Quantitative proteomic profiling of pancreatic cancer juice. Proteomics 6: 3871-3879.

Dittmar G A, Wilkinson C R, Jedrzejewski P T, Finley D. Role of a ubiquitin-like modification in polarized morphogenesis. Science. 2002; 295:2442-6.

Doherty N S, Littman B H, Reilly K, Swindell A C, Buss J M, Anderson N L. Analysis of changes in acute-phase plasma proteins in an acute inflammatory response and in rheumatoid arthritis using two-dimensional gel electrophoresis. Electrophoresis. 1998; 19:355-63.

Drevets, D. A., M. J. Dillon, J. S. Schawang, N. van Rooijen, J. Ehrchen, C. Sunderkotter, and P. J. M. Leenen. 2004. The Ly-6Chigh monocyte subpopulation transports Listeria monocytogenes into the brain during systemic infection of mice. J Immunol 172:4418-4424.

Edwards D H, Griffith T M, Ryley H C, Henderson A H. Haptoglobin-haemglobin complex in human plasma inhibits endothelium dependent relaxation: evidence that endothelium derived relaxing factor acts as a local autocoid. Cardiovasc Res. 1986; 20:549-56.

Engstrom G, Hedblad B, Stavenow L, et al. Fatality of future coronary events is related to inflammation-sensitive plasma proteins: a population-based prospective cohort study. Circulation 2004; 110:27-31.

Exocrine pancreas. In: American Joint Committee on Cancer: AJCC Cancer Staging Manual. 6th ed. New York, N.Y.: Springer, 2002, pp 157-164.

Gallucci R M, O'Dell S K, Rabe D, Fechter L D. JP-8 jet fuel exposure induces inflammatory cytokines in rat skin. Int Immunopharmacol. 2004; 4:1159-69.

Gattani A M, Mandeli J, Bruckner H W. (1996) Tumor markers in patients with pancreatic carcinoma. Cancer 78: 57-62.

Gattani A M, Mandeli J, Bruckner H W. Tumor markers in patients with pancreatic carcinoma. Gauderman W J, Vora H, McConnell R, et al. Effect of exposure to traffic on lung development from 10 to 18 years of age: a cohort study. Lancet. 2007; 369:571-7.

Gelfand J M, Neimann A L, Shin D B, Wang X, Margolis D J, Troxel A B. Risk of myocardial infarction in patients with psoriasis. JAMA. 2006; 296:1735-41.

Giurgea N, Constantinescu M I, Stanciu R, Suciu S, Muresan A. Ceruloplasmin—acute-phase reactant or endogenous antioxidant? The case of cardiovascular disease. Med Sci Monit. 2005; 11:RA48-51.

Gonzalez, M. L., Frank, M. B., Ramsland, P. A., Hanas, J. S., and Waxman, F. J. (2003) Structural analysis of IgG2A monoclonal antibodies in relation to complement deposition and renal immune complex deposition. Molecular Immunology 40, 307-17.

Greenberg A K, Lee M S. (2007) Biomarkers for lung cancer: clinical uses. Curr. Opin. Pulm. Med. 13, 249-255.

Hanas, J S, Hocker, J R, Cheung, J Y, Larabee, J L, Lerner, M R, Lightfoot, S A, Morgan, D L, Denson, K D, Prejeant, K C, Gusev, Y, Smith, B J, Hanas, R J, Postier, R G., and Brackett, D J. (2007) Biomarker Identification in Human Pancreatic Cancer Sera. Pancreas, 36: 61-69.

Harris Z L, Takahashi Y, Miyajima H, Serizawa M, MacGillivray RTA, Gitlin J D. Aceruloplasminemia: molecular characterization of this disorder of iron metabolism. Proc Natl Acad Sci USA. 1995; 92:2539-43.

Hotchkiss, R. S., and 1. E. Karl. 2003. The Pathophysiology and Treatment of Sepsis. N Engl J Med 348:138-150.

Howard B A, Zheng Z, Campa M J, Wang M Z, Sharma A, Haura E, Herndon J E 2nd, Fitzgerald M C, Bepler G, Patz E F Jr. (2004) Translating biomarkers into clinical practice: prognostic implications of cyclophilin A and macrophage migratory inhibitory factor identified from protein expression profiles in non-small cell lung cancer. Lung Cancer 46: 313-323. http://www.cancer.org/downloads/STT/CAFF2006PWSecured.pdf). American Cancer Society, 2006.

Hwang T L, Liang Y, Chien K Y, Yu JS. (2006) Overexpression and elevated serum levels of phosphoglycerate kinase 1 in pancreatic ductal adenocarcinoma. Proteomics 6: 2259-2272.

Ikari Y, Fujikawa K, Yee K O, et al. Alpha(1)-proteinase inhibitor, alpha(1)-antichymotrypsin, or alpha(2)-macroglobulin is required for vascular smooth muscle cell spreading in three-dimensional fibrin gel. J Biol Chem. 2000; 275:12799-12805.

Information for Authors. (2002) Clin. Chem. 48, 1-5.

James M L, Smith G M, Wolford J C. Applied Numerical Methods For Digital Computation, Harper & Row Publishers, New York, N.Y. 1985.

Jemal A, Murray T, Samuels A, et al. Cancer statistics, 2003. CA Cancer J. Clin. 2003; 53:5-26.

Kabbur M B, Rogers J V, Gunasekar P G, et al. Effect of JP-8 jet fuel on molecular and histological parameters related to acute skin irritation. Toxicol Appl Pharmacol. 2001; 175: 83-8.

Kinkead E R, Salins S A, Wolfe R E. Acute irritation and sensitization potential of JP-8 jet fuel. Acute Toxicol Data. 1992; 11:700.

Kittiniyom K, Gorse K M, Dalbegue F, et al. Allelic loss on chromosome band 18p11.3 occurs early and reveals heterogeneity in breast cancer progression. Breast Cancer Res 2001; 3:192-198.

Kobayashi A, Kikukawa A. Increased formaldehyde in jet engine exhaust with changes to JP-8, lower temperature, and lower humidity irritates eyes and respiratory tract. Aviat Space Environ Med. 2000; 71: 396-9.

Koomen J M, Shih L N, Coombes K R, et al. Plasma protein profiling for diagnosis of pancreatic cancer reveals the presence of host response proteins. Clin Cancer Res. 2005; 11:1110-1118.

Lan Q, Zhang L, Li G, et al. Hematotoxicity in workers exposed to low levels of benzene. Science. 2004; 306: 1774-6.

Larabee J L, Hocker J R, Cheung J Y, et al. Stress induced in heart and other tissues by rat dermal exposure to JP-8 fuel. Cell Biol Toxicol. 2005; 21:233-46.

Larabee, J. L., Hocker, J. R., and Hanas, J. S. (2005) Cys redox reactions and metal binding of a Cys2His2 zinc finger. Archives of Biochemistry and Biophysics 435, 139-149.

Larabee, J. L., Hocker, J. R., and Hanas, J. S. (2005) Mechanisms of Aurothiomalate-Cys2His2 Zinc Finger Interactions. Chemical Research in Toxicology, 18, 1943-1954.

Larabee, J. L., Hocker, J. R., and Hanas, J. S. (2008) Mechanisms of inhibition of zinc-finger transcription factors by selenium compounds ebselen and selenite. J. Inorg. Biochem. In press.

Larabee, J. L., Hocker, J. R., Cheung, J. Y., Gallucci, R. M., and Hanas, J. S. (2008) Serum Profiling of Rat Dermal Exposure to JP-8 Fuel Reveals an Acute-Phase Response. Toxicology Mechanisms and Methods, 18, 41-51.

Lee C M, Lo H W, Shao R P, et al. Selective activation of ceruloplasmin promoter in ovarian tumors: potential use for gene therapy. Cancer Res 2004; 64:1788-1793.

Leto G, Tumminello F M, Pizzolanti G, Montalto G, Soresi M, Carroccio A, Ippolito S, Gebbia N. (1997) Lysosomal aspartic and cysteine proteinases serum levels in patients with pancreatic cancer or pancreatitis. Pancreas 14:22-27.

Li J, Zhang Z, Rosenzweig J, Wang Y Y, Chan D W. (2002) Proteomics and bioinformatics approaches for identification of serum biomarkers to detect breast cancer. Clin Chem 48: 1296-1304.

Lind P, Engström G, Stavenow L, Janzon L, Lindgärde F, Hedbald B. Risk of myocardial infarction and stroke in smokers is related to plasma levels of inflammation-sensitive proteins. Arterioscler Thromb Vasc Biol. 2004; 24:577-82.

Liu Q-L, Kishi H, Ohtsuka K, Muraguchi A. Heat shock protein 70 binds caspase-activated DNase and enhances its activity in TCR-stimulated T cells. Blood. 2003; 102:1788-96.

Lonberg-Holm K, Reed D L, Roberts R C, Hebert R R, Hillman M C, Kutney R M. Three high molecular weight protease inhibitors of rat plasma. J Biol Chem. 1987; 262: 438-45.

Lowenfels A B, Maisonneuve P, Lankisch P G. (1999) Chronic pancreatitis and other risk factors for pancreatic cancer. Gastroenterol Clinics N America 28:673-685.

Lund A K, Knuckles T L, Akata C O, et al. Gasoline exhaust emissions induce vascular remodeling pathways involved in atherosclerosis. Toxicol Sci. 2007; 95:485-94.

Mackiewicz A, Kushner I, Baumann H. Acute Phase Proteins: Molecular Biology, Biochemistry & Clinical Application. CRC Press. 1993.

MathWorks, Inc. (2002) Matlab User's Guide, MathWorks, Inc.

Merrel K, Southwick K, Graves S W, Esplin M S, Lewis N E, Thulinab C D. (2004) Analysis of Low-Abundance, Low-Molecular-Weight Serum Proteins Using Mass Spectrometry. J Biomol Tech, 15: 238-248.

Nakae Y, Hayakawa T, Kondo T, et al. Diagnostic value of serum level of alpha 2-macroglobulin-trypsin complex in pancreatic diseases using a colorimetric assay with a synthetic chromogenic substrate. Nippon Shokakibyo Gakkai Zasshi. 1991; 88:2853-2860.

National Committee for Clinical Laboratory Standards. (2004) User evaluation of precision performance of clinical chemistry devices. NCCLS Tentative Guideline EP5-T.

Ornstein D K, Rayford W, Fusaro V A, et al. Serum proteomic profiling can discriminate prostate cancer from benign prostates in men with total prostate specific antigen levels between 2.5 and 15.0 ng/ml. J. Urol. 2004; 172:1302-1305.

Peters A, von Klot S, Heier M, et al. Cooperative health research in the region of Augsburg study group. Exposure to traffic and the onset of myocardial infarction. N Engl J. Med. 2004; 351:1721-30.

Pleil J D, Smith L B, Zelnick S D. Personal exposure to JP-8 jet fuel vapors and exhaust at air force bases. Environ Health Persp. 2000; 108:183-92.

Poli D. Carbognani P. Corradi M. Goldoni M. Acampa O. Balbi B. Bianchi L. Rusca M. Mutti A. (2005) Exhaled volatile organic compounds in patients with non-small cell lung cancer: cross sectional and nested short-term follow-up study. Respiratory Res 6:71, 2005.

Postier R G, Lerner M R, Lightfoot S A, et al. DNA ploidy and Markovian analysis of Neoplastic progression in experimental pancreatic cancer. J Histochem Cytochem. 2003; 51:303-309.

Postier R G. Past, present, and future of pancreatic surgery. Am J Surgery 2001; 182:547-551. Richter R, Schuz-Knappe P, Schrader M, et al. Composition of the peptide fraction in human blood plasma: database of circulating human peptides. J Chromatog B Biomed Sci Appl. 1999; 726:25-35.

Ritchie G D, Rossi 3rd J, Nordholm A F, et al. Effects of repeated exposure to JP-8 jet fuel vapor on learning of simple and difficult operant tasks by rats. J Toxicol Environ Health A. 2001b; 64:385-415.

Ritchie G D, Still K R, Alexander W K, et al. A review of the neurotoxicity risk of selected hydrocarbon fuels. J Toxicol Environ Health B Crit Rev. 2001a; 4:223-312.

Robledo R F, Young R S, Lantz R C, Witten M L. Short-term pulmonary response to inhaled JP-8 jet fuel aerosol in mice. Toxicol Pathol. 2000; 28:656-63.

Rosty C, Christa L, Kuzdzal S, Baldwin W M, Zahurak M L, Carnot F, Chan D W, Canto M, Lillemoe K D, Cameron J L, Yeo C J, Hruban R H, Goggins M. (2002) Identification of hepatocarcinoma-intestine-pancreas/pancreatitis-associated protein I as a biomarker for pancreatic ductal adenocarcinoma by protein biochip technology. Cancer Res 62:1868-1875.

Samso M, Palumbo M J, Radermacher M, et al. A Bayesian method for classification of images from electron micrographs. J Struct Biol. 2002; 138:157-170.

Schroder F H, Roobol M J, Damhuis R A, et al. Rotterdam randomized pilot studies of screening for prostate cancer—an overview after 10 years. J Natl Cancer Inst. 2005; 97:696. Cancer 1996; 78:57-62.

Semmes O J, Feng Z, Adam B L, Banez L L, Bigbee W L, Campos D, Cazares L H, Chan D W, Grizzle W E, Izbicka E, Kagan J, Malik G, McLerran D, Moul J W, Partin A, Prasanna P, Rosenzweig J, Sokoll L J, Srivastava S, Srivastava S, Thompson I, Welsh M J, White N, Winget M, Yasui Y, Zhang Z, Zhu L. (2005) Evaluation of serum protein profiling by surface-enhanced laser desorption/ionization time-of-flight mass spectrometry for the detection of prostate cancer: I. Assessment of platform reproducibility. Clin Chem 51, 102-112.

Semmes O J, Feng Z, Adam B L, et al. Evaluation of serum protein profiling by surface-enhanced laser desorption/ionization time-of-flight mass spectrometry for the detection of prostate cancer: I. Assessment of platform reproducibility. Clin Chem. 2005; 51:102-112.

Sorace J M, Zhan M. (2003) A data review and re-assessment of ovarian cancer serum proteomic profiling. BMC Bioinformatics 4: 24.

Spaulding H L, Saijo F, Turnage R H, Alexander J S, Aw T Y, Kalogeris T J. Apolipoprotein A-IV attenuates oxidant-induced apoptosis in mitotic competent, undifferentiated cells by modulating intracellular glutathione redox balance. Am J Physiol Cell Physiol. 2006; 290:C95-C103.

Steinmetz A, Barbaras R, Ghalim N, Clavey V, Fruchart J C, Ailhaud G. Human apolipoprotein A-IV binds to apolipoprotein A-I/A-II receptor sites and promotes cholesterol efflux from adipose cells. J Biol Chem. 1990; 265:7859-63.

Stoica B A, Boulares A H, Rosenthal D S, Iyer S, Hamilton I D, Smulson M E. Mechanisms of JP-8 jet fuel toxicity. I. Induction of apoptosis in rat lung epithelial cells. Toxicol Appl Pharmacol. 2001; 171:94-106.

Szalai A J, van Ginkel F W, Wang Y, et al. Complement-dependent acute-phase expression of C-reactive protein and serum amyloid P-component. J. Immunol. 2000; 165: 1030-1035.

Tan Z-J, Hu X-G, Cao G-S, et al. Analysis of gene expression profile of pancreatic carcinoma using cDNA mircroarray. World J. Gastroenterol. 2003; 9:818-823.

Teknos T N, Islam M, Arenberg D A, et al. The effect of tetrathiomolybdate on cytokine expression, angiogenesis, and tumor growth in squamous cell carcinoma of the head and neck. Arch Otolaryngol Head Neck Surg. 2005; 131: 204-211.

Thurman D, Alverson C, Dunn K, Guerrero J, Sniezek J. Traumatic brain injury in the United States: a public health perspective. Journal of Head Trauma Rehabilitation 1999; 14(6):602-15.

Trachte A L, Suthers S E, Lerner M E, et al. Increased expression of alpha-1-antitrypsin, Glutathione S-transferase, and vascular endothelial growth factor in human pancreatic andenocarcinoma. Amer J. Surg. 2002; 184:642-647.

Ullrich SE. Dermal application of JP-8 jet fuel induces immune suppression. Toxicol Sci. 1999; 52:61-7.

Ulrich A B, Schmied B M, Standop J, et al. Differences in the expression of glutathione S-transferases in normal pancreas, chronic pancreatitis, secondary chronic pancreatitis, and pancreatic cancer. Pancreas 2002; 24:291-297.

Valerio A, Basso D, Mazza S, et al. Serum protein profiles of patients with pancreatic cancer and chronic pancreatitis: searching for a diagnostic protein pattern. Rapid Commun Mass Spectrom. 2001; 15:2420-2425.

Verma M, Wright G L Jr, Hanash S M, et al. (2001) Proteomic approaches within the NCI early detection research network for the discovery and identification of cancer biomarkers. Ann N Y Acad Sci. 2001; 945:103-115.

Villanueva J, Shaffer D R, Philip J, Chaparro C A, Erdjument-Bromage H, Olshen A B, Fleisher M, Lilja H, Brogi E, Boyd J, Sanchez-Carbayo M, Holland E C, Cordon-Cardo C, Scher H I, Tempst P. (2006) Differential exoprotease activities confer tumor-specific serum peptidome patterns. J Clin Invest 116, 271-284.

Wang W, Abbruzzese J L, Evans D B, et al. The nuclear factor-kappa B Rel A transcription factor is constituitively activated in human pancreatic adenocarcinoma cells. Clin Cancer Res. 1999; 5:119-127.

Wang, T., T. Town, L. Alexopoulou, J. F. Anderson, E. Fikrig, and R. A. Flavell. 2004. Toll-like receptor 3 mediates West Nile virus entry into the brain causing lethal encephalitis. Nat Med 10:1366-1373.

www.medicine.uiowa.edu/path handbook/Appendix/Chem/PRED VALUE THEORY.html

Yang S Y, Xiao X Y, Zhang W G, Zhang L J, Zhang W, Zhou B, Chen G, He D C. (2005) Application of serum SELDI proteomic patterns in diagnosis of lung cancer. BMC Cancer 5:83.

Yu K H, Rustgi A K, Blair I A. (2005) Characterization of proteins in human pancreatic cancer serum using differential gel electrophoresis and tandem mass spectrometry. J Proteome Res 4: 1742-1751.

Yu Y, Chen S, Wang L S, et al. Prediction of pancreatic cancer by serum biomarkers using surface-enhanced laser desorption/ionization-based decision tree classification. Oncology 2005; 68:79-86.

Zharkikh A, Wen-Hsiung L. Statistical Properties of Bootstrap Estimation Phylogenetic Variability from Nucleotide Sequences. I. Four Taxa with a Molecular Clock. Mol Biol Evol. 1992; 9:1119-1147.

What is claimed is:

1. A method of identifying biomarkers in liquid biological samples from cancer patients, comprising the steps of:

(a) obtaining a plurality of first liquid biological samples, wherein the plurality of first liquid biological samples are obtained from patients having the same type of cancer;

(b) obtaining a plurality of second liquid biological samples, wherein the plurality of second liquid biological samples are obtained from normal, healthy patients;

(c) directly subjecting the plurality of first liquid biological samples and the plurality of second liquid biological samples to electrospray ionization mass spectrometry (ESI MS) to produce a mass spectrum profile for each liquid biological sample;

(d) constructing a first database comprising peaks present in the mass spectrum profiles of the plurality of first liquid biological samples;

(e) constructing a second database comprising peaks present in the mass spectrum profiles of the plurality of second liquid biological samples;

(f) comparing the second database to the first database to identify at least one series of statistically significant peaks that distinguish the plurality of liquid biological samples obtained from cancer patients from the plurality of liquid biological samples obtained from healthy patients; and (g) determining that the at least one series of statistically significant peaks identified in (f) comprise at least one biomarker related to the type of cancer.

2. The method of claim 1 wherein, in the step of comparing the second database to the first database to identify at least one series of statistically significant peaks, the at least one series of statistically significant peaks comprises at least one of:

(a) at least one statistically significant peak present in the plurality of liquid biological samples obtained from cancer patients that is not present in the plurality of liquid biological samples obtained from healthy patients;

(b) at least one statistically significant peak present in the plurality of liquid biological samples obtained from healthy patients that is not present in the plurality of liquid biological samples obtained from cancer patients;

(c) at least one statistically significant peak present in the plurality of liquid biological samples obtained from cancer patients that is present at an increased intensity and/or area when compared to the same peak in the plurality of liquid biological samples obtained from healthy patients; and (d) at least one statistically significant peak present in the plurality of liquid biological samples obtained from healthy patients that is present at an increased intensity and/or area when compared to the same peak in the plurality of liquid biological samples obtained from cancer patients.

3. The method of claim 1, wherein the step of obtaining a plurality of first liquid biological samples is further defined as obtaining a plurality of first liquid biological samples obtained from pancreatic cancer patients.

4. The method of claim 1, wherein the step of obtaining a plurality of first liquid biological samples is further defined as obtaining a plurality of first liquid biological samples obtained from lung cancer patients.

5. The method of claim 1 wherein, in the step of directly subjecting the plurality of first liquid biological samples and the plurality of second liquid biological samples to electrospray ionization mass spectrometry (ESI MS), the electrospray ionization mass spectrometry is further defined as electrospray ionization-time of flight mass spectrometry (ESI-TOF MS).

6. The method of claim 1, wherein step (g) is further defined as determining that the at least one series of statistically significant peaks identified in (f) comprises at least twenty biomarkers related to the type of cancer.

7. The method of claim 1, wherein the at least one biomarker identified in step (g) has a mass in the low mass region of between about 350 m/z and about 2000 m/z.

8. The method of claim 1, wherein the at least one biomarker identified in step (g) has a mass in the low mass region of between about 400 m/z and about 2000 m/z.

9. The method of claim 1, wherein the at least one biomarker identified in step (g) has a mass in the low mass region of between about 500 m/z and about 1200 m/z.

10. The method of claim 1, wherein the at least one biomarker identified in step (g) has a mass in the low mass region of between about 800 m/z and about 1500 m/z.

11. A method of identifying biomarkers in a liquid biological sample from a cancer patient, comprising the steps of:

(a) obtaining a plurality of first liquid biological samples, wherein the plurality of first liquid biological samples are obtained from patients having the same type and subtype or stage of cancer;

(b) obtaining a plurality of second liquid biological samples, wherein the plurality of second liquid biological samples are obtained from patients having the same type of cancer as the plurality of first liquid biological samples but a different subtype or stage of cancer;

(c) obtaining a plurality of third liquid biological samples, wherein the plurality of third liquid biological samples are obtained from normal, healthy patients;

(d) directly subjecting the plurality of first liquid biological samples, the plurality of second liquid biological samples and the plurality of third liquid biological samples to electrospray ionization mass spectrometry (ESI MS) to produce a mass spectrum profile for each liquid biological sample;

(e) constructing a first database comprising peaks present in the mass spectrum profiles of the plurality of first liquid biological samples;

(f) constructing a second database comprising peaks present in the mass spectrum profiles of the plurality of second liquid biological samples;

(g) constructing a third database comprising peaks present in the mass spectrum profiles of the plurality of third liquid biological samples;

(h) comparing the third database to the first and second databases to identify at least one series of statistically significant peaks that distinguish the plurality of liquid biological samples obtained from cancer patients from the plurality of liquid biological samples obtained from healthy patients;

(i) determining that the at least one series of statistically significant peaks identified in (h) comprises at least one biomarker related to the type of cancer, (j) comparing the first database to the second database to identify at least one series of statistically significant peaks present in the plurality of liquid biological samples obtained from patients having one cancer subtype or stage that is not present in the plurality of liquid biological samples obtained from patients having another cancer subtype or stage; and (k) determining that the at least one series of statistically significant peaks identified in (j) comprises at least one biomarker related to a specific subtype or stage of cancer.

12. The method of claim 11 wherein, in step (h), the at least one series of statistically significant peaks comprises at least one of:

(a) at least one statistically significant peak present in the plurality of liquid biological samples obtained from cancer patients that is not present in the plurality of liquid biological samples obtained from healthy patients;

(b) at least one statistically significant peak present in the plurality of liquid biological samples obtained from healthy patients that is not present in the plurality of liquid biological samples obtained from cancer patients;

(c) at least one statistically significant peak present in the plurality of liquid biological samples obtained from cancer patients that is present at an increased intensity and/or area when compared to the same peak in the plurality of liquid biological samples obtained from healthy patients; and (d) at least one statistically significant peak present in the plurality of liquid biological samples obtained from healthy patients that is present at an increased intensity and/or area when compared to the same peak in the plurality of liquid biological samples obtained from cancer patients.

13. The method of claim 11 wherein, in step (j), the at least one series of statistically significant peaks comprises at least one of:

(a) at least one statistically significant peak present in the plurality of liquid biological samples obtained from patients having one cancer subtype or stage that is not present in the plurality of liquid biological samples obtained from patients having another cancer subtype or stage; and (b) at least one statistically significant peak present in the plurality of liquid biological samples obtained from patients having one cancer subtype or stage that is present at an increased intensity and/or area when compared to the same peak in the plurality of liquid biological samples obtained from patients having another cancer subtype or stage.

14. The method of claim 11, wherein the steps of obtaining a plurality of first liquid biological samples and a plurality of second biological samples, the pluralities of first and second biological samples are further defined as being obtained from lung cancer patients.

15. The method of claim 11 wherein, in step (d), the electrospray ionization mass spectrometry is further defined as electrospray ionization-time of flight mass spectrometry (ESI-TOF MS).

16. The method of claim 11, wherein step (i) is further defined as determining that the at least one series of statistically significant peaks identified in (h) comprises at least twenty biomarkers related to the type of cancer.

17. The method of claim 11, wherein step (k) is further defined as determining that the at least one series of statistically significant peaks identified in (j) comprises at least twenty biomarkers related to a specific subtype or stage of cancer.

18. The method of claim 11, wherein the at least one biomarker identified in at least one of steps (i) and (k) has a mass in the low mass region of between about 350 m/z and about 2000 m/z.

19. The method of claim 11, wherein the at least one biomarker identified in at least one of steps (i) and (k) has a mass in the low mass region of between about 400 m/z and about 2000 m/z.

20. The method of claim 11, wherein the at least one biomarker identified in at least one of steps (i) and (k) has a mass in the low mass region of between about 500 m/z and about 1200 m/z.

21. The method of claim 11, wherein the at least one biomarker identified in at least one of steps (i) and (k) has a mass in the low mass region of between about 800 m/z and about 1500 m/z.

22. A method of identifying biomarkers in liquid biological samples from patients having a particular disease state, comprising the steps of:

(a) obtaining a plurality of first liquid biological samples, wherein the plurality of first liquid biological samples are obtained from patients having a particular disease state;

(b) obtaining a plurality of second liquid biological samples, wherein the plurality of second liquid biological samples are obtained from normal, healthy patients;

(c) directly subjecting the plurality of first liquid biological samples and the plurality of second liquid biological samples to electrospray ionization mass spectrometry (ESI MS) to produce a mass spectrum profile for each liquid biological sample;

(d) constructing a first database comprising peaks present in the mass spectrum profiles of the plurality of first liquid biological samples;

(e) constructing a second database comprising peaks present in the mass spectrum profiles of the plurality of second liquid biological samples;

(f) comparing the second database to the first database to identify at least one series of statistically significant peaks that distinguish the plurality of liquid biological samples obtained from patients having a particular disease state from the plurality of liquid biological samples obtained from healthy patients; and (g) determining that the at least one series of statistically significant peaks identified in (f) comprise at least one biomarker related to the type of particular disease state.

23. The method of claim 22 wherein, in the step of comparing the second database to the first database to identify at least one series of statistically significant peaks, the at least one series of statistically significant peaks comprises at least one of:

(a) at least one statistically significant peak present in the plurality of liquid biological samples obtained from patients having a particular disease state that is not present in the plurality of liquid biological samples obtained from healthy patients;

(b) at least one statistically significant peak present in the plurality of liquid biological samples obtained from healthy patients that is not present in the plurality of liquid biological samples obtained from patients having a particular disease state;

(c) at least one statistically significant peak present in the plurality of liquid biological samples obtained from patients having a particular disease state that is present at an increased intensity and/or area when compared to the same peak in the plurality of liquid biological samples obtained from healthy patients; and (d) at least one statistically significant peak present in the plurality of liquid biological samples obtained from healthy patients that is present at an increased intensity and/or area when compared to the same peak in the plurality of liquid biological samples obtained from patients having a particular disease state.

24. The method of claim 22 wherein, in the step of directly subjecting the plurality of first liquid biological samples and the plurality of second liquid biological samples to electrospray ionization mass spectrometry (ESI MS), the electrospray ionization mass spectrometry is further defined as electrospray ionization-time of flight mass spectrometry (ESI-TOF MS).

25. The method of claim 22, wherein step (g) is further defined as determining that the at least one series of statistically significant peaks identified in (f) comprises at least twenty biomarkers related to the type of particular disease state.

26. The method of claim 22, wherein the at least one biomarker identified in step (g) has a mass in the low mass region of between about 350 m/z and about 2000 m/z.

27. The method of claim 22, wherein the at least one biomarker identified in step (g) has a mass in the low mass region of between about 400 m/z and about 2000 m/z.

28. The method of claim 22, wherein the at least one biomarker identified in step (g) has a mass in the low mass region of between about 500 m/z and about 1200 m/z.

29. The method of claim 22, wherein the at least one biomarker identified in step (g) has a mass in the low mass region of between about 800 m/z and about 1500 m/z.

* * * * *

UNITED STATES PATENT AND TRADEMARK OFFICE

CERTIFICATE OF CORRECTION

PATENT NO. : 8,710,429 B2
APPLICATION NO. : 12/341252
DATED : April 29, 2014
INVENTOR(S) : Jay S. Hanas et al.

It is certified that error appears in the above-identified patent and that said Letters Patent is hereby corrected as shown below:

On the Title Page:

Under Item (73) Assignee: Delete “Normal,” and replace with -- Norman, --.

In the Specification:

Column 8, line 60: After “Heparin cofactor” delete “11” and replace with -- II --.

Column 8, line 62: After “protein” delete “1,” and replace with -- I, --.

Column 14, line 19: Delete “1V” and replace with -- IV --.

Column 16, line 45: Delete “(stage 1V)” and replace with -- (stage IV) --.

Column 30, line 22: Delete “pamps” and replace with -- μamps --.

In the References:

Column 42, line 28: After “Skovsted, and” delete “1.” and replace with -- I. --.

Column 43, line 33: Before “E. Karl.” delete “1.” and replace with -- I. --.

Signed and Sealed this
Twenty-second Day of July, 2014

Michelle K. Lee

Michelle K. Lee
*Deputy Director of the United States Patent and Trademark Office*